United States Patent [19]
Albright et al.

[11] Patent Number: 6,071,903
[45] Date of Patent: Jun. 6, 2000

[54] 2,3,4,5-TETRAHYDRO-1H-[1,4]-BENZODIAZEPINE-3-HYDROXYAMIC ACIDS

[75] Inventors: Jay D. Albright; Efren G. Delos Santos, both of Nanuet; Xuemei Du, Valley Cottage, all of N.Y.

[73] Assignee: American Cyanamid Company, Madison, N.J.

[21] Appl. No.: 09/318,919

[22] Filed: May 26, 1999

Related U.S. Application Data

[63] Continuation of application No. 09/237,058, Jan. 26, 1999, abandoned.
[60] Provisional application No. 60/093,057, Jan. 27, 1998.

[51] Int. Cl.[7] ..................... A61K 31/5513; C07D 243/14
[52] U.S. Cl. ............................................ 514/221; 540/570
[58] Field of Search .............................. 540/570; 514/221

[56] References Cited

U.S. PATENT DOCUMENTS

| | | | |
|---|---|---|---|
| 5,455,258 | 10/1995 | MacPherson et al. | 514/357 |
| 5,795,887 | 8/1998 | Aquino et al. | 514/221 |

FOREIGN PATENT DOCUMENTS

| | | | |
|---|---|---|---|
| WO 9718194 | 5/1997 | WIPO . | |
| WO 9720824 | 6/1997 | WIPO . | |
| WO 9730992 | 8/1997 | WIPO . | |

OTHER PUBLICATIONS

Yu, A. E. et al., *Drugs and Aging*, 11:229–244 (1997).
Beckett, R. P. et al., *Drug Discovery Today*, 1:16–26 (1996).
Beeley, N. R. A. et al., *Curr. Opin. Ther. Patents* 4(1):7–16 (1994).
Morphy, J. R. et al. *Curr. Medicinal Chem.* 2:743–762 (1995).
Davidsen, S. K., *Exp. Opin. Ther. Patents* 5(2):1087–1100 (1995).
Porter, J. R. et al., *Exp. Opin. Ther. Patents* 5(12):1287–1296 (1995).
Zask, A. et al., *Current Pharmaceutical Design*, 2(6):624–661 (1996).
Levy, D. E. et al., Emerging Drugs, 2:205–230 (1997).
McGeehan, G. M. et al., *Current Pharmaceutical Design*, 2:662–667 (1996).

*Primary Examiner*—Mukund J. Shah
*Assistant Examiner*—Bruck Kifle
*Attorney, Agent, or Firm*—Michael R. Nagy

[57] ABSTRACT

Compounds are provided having the following formula:

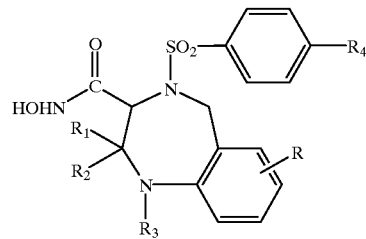

wherein R, $R_1$, $R_2$, $R_3$, and $R_4$ are defined in the specification, which have matrix metalloproteinase inhibiting activity.

85 Claims, No Drawings

2,3,4,5-TETRAHYDRO-1H-[1,4]-BENZODIAZEPINE-3-HYDROXYAMIC ACIDS

CROSS REFERENCE TO RELATED APPLICATIONS

This application is a continuation of application Ser. No. 09/237,058, filed Jan. 26, 1999, now abandoned, which claims the benefit of U.S. Provisional Application No. 60/093,057, which was converted from U.S. patent application Ser. No. 09/014,374, filed Jan. 27, 1998, pursuant to a petition filed under 37 C.F.R. 1.53(c)(2)(i) filed Jul. 30, 1998.

FIELD OF INVENTION

This invention relates to 4-(4-substituted-benzenesulfonyl)-2,3,4,5-tetrahydro-1H-[1,4] benzodiazepine-3-hydroxyamic acids which act as matrix metalloproteinase inhibitors. The compounds of the present invention are useful in disease conditions mediated by matrix metalloproteinases, such as tumor growth. osteoarthritis. rheumatoid arthritis and degenerative cartilage loss.

BACKGROUND OF THE INVENTION

Matrix metalloproteinases (MMPs) are a group of enzymes that have been implicated in the pathological destruction of connective tissue and basement membranes. These zinc-containing endopeptidases consist of several subsets of enzymes, including collagenases, stromelysins and gelatinases. Of these, the gelatinases have been shown to be the MMPs most intimately involved with the growth and spread of tumors.

For example, it is known that the level of expression of gelatinase is elevated in malignancies, and that gelatinase can degrade the basement membrane which leads to tumor metastasis. Angiogenesis, required for the growth of solid tumors, has also recently been shown to have a gelatinase component to its pathology as reported in "Matrix Metalloproteinases, Novel Targets for Directed Cancer Therapy", *Drugs and Aging,* 11:229–244 (1997).

Other conditions mediated by MMPs include restenosis, MMP-mediated osteopenias, inflammatory diseases of the central nervous system, skin aging, osteoarthritis, rheumatoid arthritis, septic arthritis, corneal ulceration, abnormal wound healing, bone disease, proteinuria. aneurysmal aortic disease, degenerative cartilage loss following traumatic joint injury. demyelinating diseases of the nervous system, cirrhosis of the liver, glomerular disease of the kidney, premature rupture of fetal membranes, inflammatory bowel disease, periodontal disease. age-related macular degeneration, diabetic retinopathy, proliferative vitreoretinopathy, retinopathy of prematurity, ocular inflammation, keratoconus, Sjogren's syndrome, myopia, ocular tumors, ocular angiogenesis/ neo-vascularization and corneal graft rejection. Studies relating to these conditions are set forth, e.g., in "Recent Advances in Matrix Metalloproteinase Inhibitor Research", R. P. Beckett et al., *Research Focus,* 1:16–26, (1996); *Curr. Opin. Ther. Patents,* 4(1): 7–16, (1994); *Curr. Medicinal Chem.,* 2: 743–762, (1995); *Exp. Opin. Ther. Patents,* 5(2): 1087–110, (1995); *Exp. Opin. Ther. Patents,* 5(12): 1287–1196, (1995); "Inhibition of Matrix Metallo-proteinases: Structure Based Design", *Current Pharmaceutical Design,* 2:524–661. (1996). "Matrix Metalloproteinase Inhibitor Drugs", *Emerging Drugs,* 2:205–230 (1997).

TNF-α converting enzyme (TACE) catalyzes the formation of TNF-α from membrane bound TNF-α precursor protein. TNF-α is a pro-inflammatory cytokine that is believed to have a role in rheumatoid arthritis, septic shock, graft rejection, cachexia, anorexia, inflammation, congestive heart failure, inflammatory disease of the central nervous system, inflammatory bowel disease, insulin resistance and HIV infection, in addition to its well-documented antitumor properties. Research with anti-TNF-α antibodies in transgenic animals has demonstrated that blocking the formation of TNF-α inhibits the progression of arthritis. This observation has recently been extended to humans as described in "TNF-α in Human Diseases", *Current Pharmaceutical Design,* 2:662–667 (1996).

It is expected that small molecule inhibitors of MMPs and TACE would have the potential for treating a variety of disease states. Although a variety of MMP and TACE inhibitors are known, many of these molecules are peptidic and peptide-like which demonstrate bioavailability and pharmacokinetic problems. Long acting, orally bioavailable non-peptide inhibitors of MMPs and/or TACE would thus be highly desirable for the treatment of the disease states discussed above.

U.S. Pat. No. 5,455,258 discloses 2-substituted-2-(arylsulfonylamino) hydroxyamic acids and their use as MMP inhibitors. WO 97/18194, discloses N-(arylsulfonyl) tetrahydroisoquinolone-hydroxyamic acids and related bicyclic derivatives thereof and their use as MMP inhibitors. WO 97/20824 discloses 1-(arylsulfonyl)-4-(substituted) piperazine-2-hydroxyamic acids, 4-(arylsulfonyl) morpholine-3-hydroxyamic acids, 4-(arylsulfonyl)-tetrahydro-2H,1,4-thiazine-3-hydroxyamic acids, 3-(substituted-1-(arylsulfonyl)hexahydro-2-hydroxyamic acids and related compounds as useful MMP inhibitors.

SUMMARY OF THE INVENTION

This invention relates to novel derivatives of substituted 2,3,4,5-tetrahydro-1H-[1,4]benzodiazepine-3-carboxylic acid hydroxyamide which exhibit inhibitory activity against MMPs. The compounds of the present invention are represented by the following formula 1

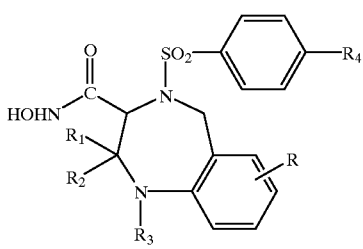

wherein

R is selected from hydrogen, $(C_1-C_3)$ alkyl, —CN, —OR', —SR', —CF$_3$, —OCF$_3$, Cl, F, NH$_2$, NH(C$_1$-C$_3$) alkyl, —N(R')CO(C$_1$-C$_3$)alkyl, —N(R')(R'), NO$_2$, —CONH$_2$, —SO$_2$NH$_2$, —SO$_2$N(R')(R'), or —N(R') COCH$_2$O-(C$_1$-C$_3$)alkyl, wherein R' is (C$_1$-C$_3$) alkyl or hydrogen:

$R_4$ is $(C_1-C_6)$alkyl-O—, $(C_1-C_6)$alkyl-S—,

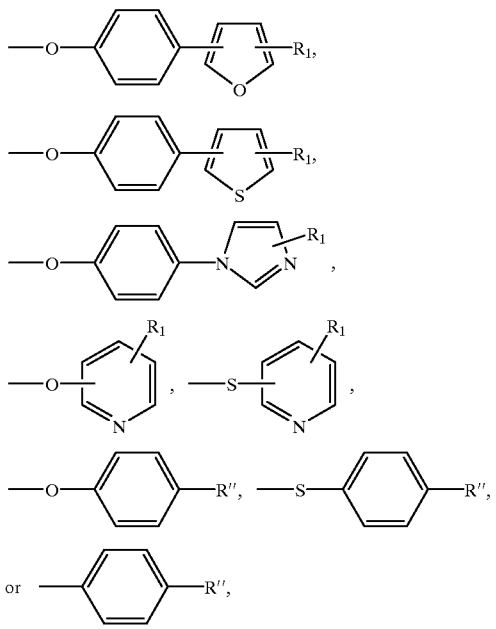

wherein R″ is hydrogen, halogen, cyano, methyl or —OCH$_3$;

$R_1$ and $R_2$ are each, independently, hydrogen or CH$_3$;

$R_3$ is $(C_1-C_8)$alkyl, NH$_2$CH$_2$CO—, $(C_1-C_6)$alkylNHCH$_2$CO—, HO(CH$_2$)$_m$CO—, HCO—, Aryl(CH$_2$)$_n$CO—, Heteroaryl(CH$_2$)$_n$CO—, $(C_1-C_3)$alkyl-O-(CH$_2$)$_n$CO—, $(C_1-C_3)$alkylCO—, $(C_1-C_3)$alkylCO—NHCH$_2$CO—, $(C_3-C_7)$cycloalkylCO—, $(C_1-C_3)$alkylSO$_2$—, Aryl(CH$_2$)$_n$SO$_2$—, Heteroaryl(CH$_2$)$_n$SO$_2$—, $(C_1-C_3)$alkyl-O-(CH$_2$)$_m$—SO$_2$—, $(C_1-C_3)$alkyl-O-(CH$_2$)$_m$, $(C_1-C_3)$alkyl-O-$(C_1-C_3)$alkyl-O-$(C_1-C_3)$alkyl, HO—$(C_1-C_3)$alkyl-O-$(C_1-C_3)$alkyl, Aryl-O—CH$_2$CO—, Heteroaryl-O—CH$_2$CO—, ArylCH═CHCO—, HeteroarylCH═CHCO—, $(C_1-C_3)$alkylCH═CHCO—,

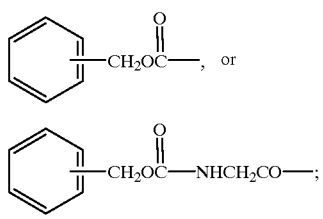, or

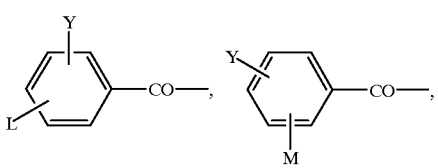

Aryl$(C_1-C_3)$alkyl, Heteroaryl$(C_1-C_3)$alkyl, ArylCH═CHCH$_2$—, HeteroarylCH═CHCH$_2$—, $(C_1-C_6)$alkylCH═CHCH$_2$—,

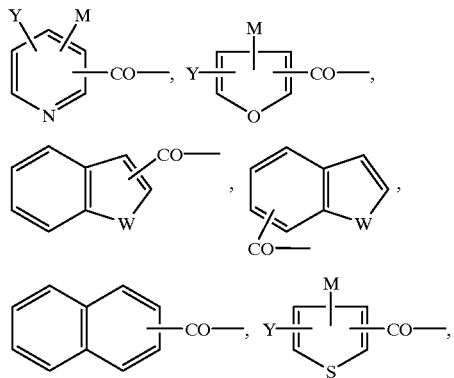

-continued

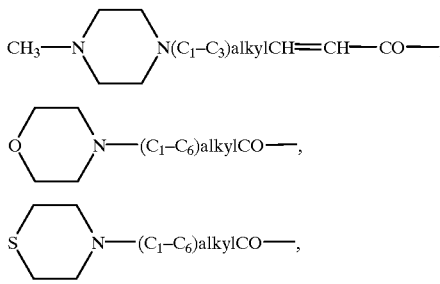

R'OCH$_2$ CH(OR')CO—, (R'OCH$_2$)$_2$C(R')CO—.

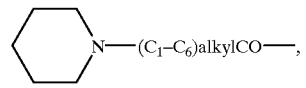

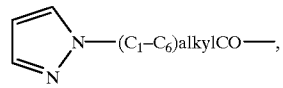

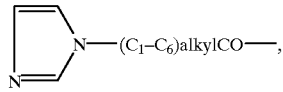

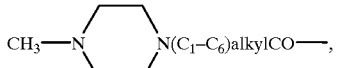

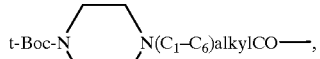

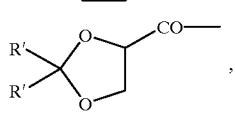

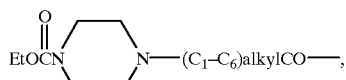

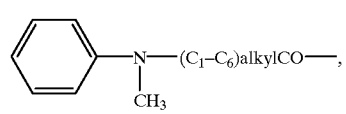

-continued

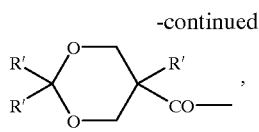

[(C₁-C₆)alkyl]₂—N—(C₁-C₆)alkyl CO—, or (C₁-C₆)alkyl-NH—(C₁-C₆)alkylCO—;

wherein m=1 to 3; n=0 to 3;

Aryl is

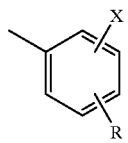

and

Heteroaryl is

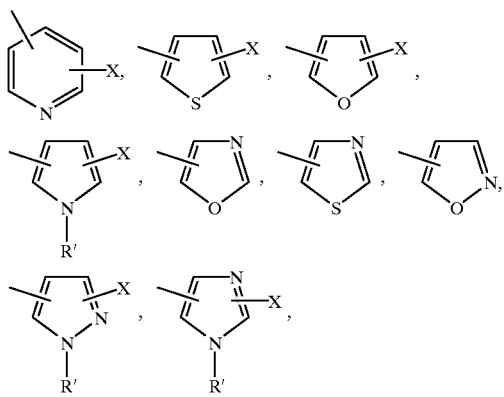

wherein X is hydrogen, halogen, (C₁-C₃)alkyl or —OCH₃ and R and R' are as defined above;

L is hydrogen, (C₁-C₃)alkyl, —CN, —OR', —SR', —CF₃, —OCF₃, Cl, F, NH₂, —NH—(C₁-C₃)alkyl, —N(R')CO(C₁-C₃)alkyl. N(R')(R'), —NO₂, —CONH₂, —SO₂NH₂, —SO₂N(R')(R'), —N(R')COCH₂O—(C₁-C₃)alkyl,

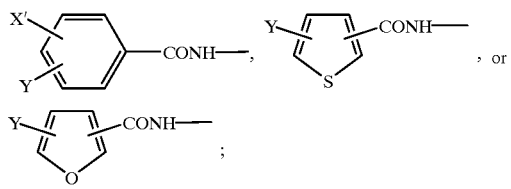

M is

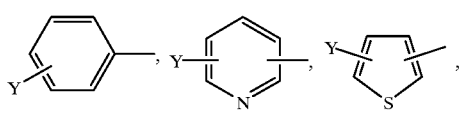

-continued

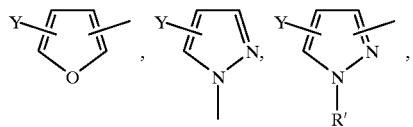

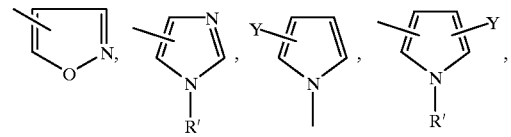

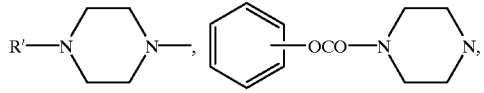

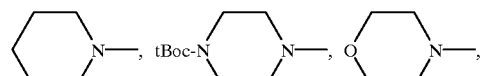

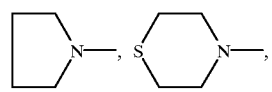

or N(R')(R') where R' is as defined above;

W is O, S, NH or N(C₁-C₃)alkyl;

Y is hydrogen, F, Cl, CF₃ or OCH₃; and X' is halogen, hydrogen, (C₁-C₃)alkyl, O-(C₁-C₃)alkyl, or —CH₂OH; and pharmaceutically acceptable salts thereof.

DETAILED DESCRIPTION OF THE INVENTION

Preferably, the compounds of the present invention are those of formula 1 wherein R is hydrogen, (C₁-C₃)alkyl, —CN, —OR', —SR', —CF₃, —OCF₃, Cl, F, NH₂, NH(C₁-C₃)alkyl, —N(R')CO(C₁-C₃)alkyl, —N(R')(R'), NO₂, —CONH₂, —SO₂NH₂, —SO₂N(R')(R'), or —N(R')COCH₂O-(C₁-C₃)alkyl, wherein R' is (C₁-C₃)alkyl or hydrogen;

R₄ is (C₁-C₆)alkyl-O—, (C₁-C₆)alkyl-S—,

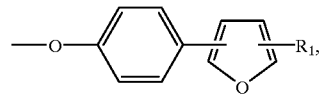

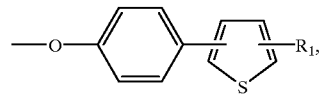

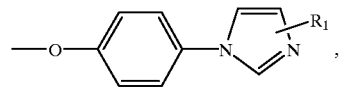

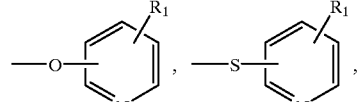

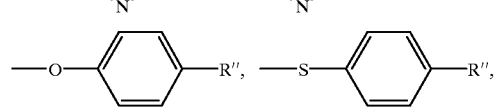

-continued

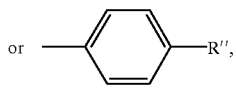

wherein R" is hydrogen, halogen, cyano, methyl or —OCH$_3$;

R$_1$ and R$_2$ are each, independently, hydrogen or CH$_3$;

R$_3$ is (C$_1$–C$_8$)alkyl, NH$_2$CH$_2$CO—, (C$_1$–C$_6$) alkylNHCH$_2$CO—, HO(CH$_2$)$_m$CO—, HCO—, Aryl(CH$_2$)$_n$CO—, Heteroaryl(CH$_2$)$_n$CO—, (C$_1$–C$_3$)alkyl-O-(CH$_2$)$_n$CO—, (C$_1$–C$_3$)alkylCO—, (C$_1$–C$_3$)alkylCO—NHCH$_2$CO—, (C$_3$–C$_7$)cycloalkylCO—, Aryl-O—CH$_2$CO—, HeteroarylOCH$_2$CO—, ArylCH=CHCO—, HeteroarylCH=CHCO—, (C$_1$–C$_3$)alkylCH=CHCO—,

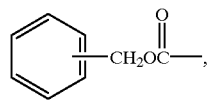

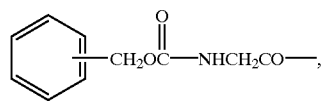

wherein
m=1 to 3; n=0 to 3;
Aryl is

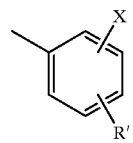

and
Heteroaryl is

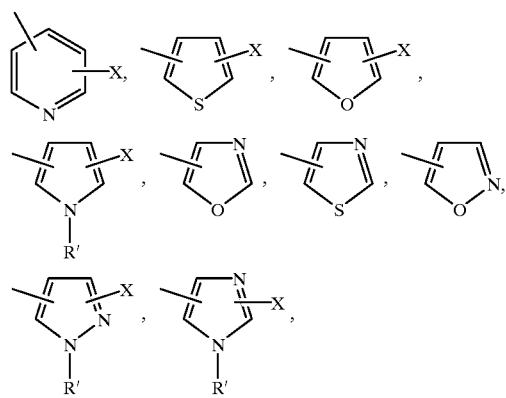

wherein X is hydrogen, halogen, (C$_1$–C$_3$)alkyl or —OCH$_3$ wherein R and R' are as defined above; and pharmaceutically acceptable salts thereof.

More preferably, the compounds of the present invention are those of formula 1 wherein R is hydrogen, (C$_1$–C$_3$)alkyl, —CN, —OR', —SR', —CF$_3$, —OCF$_3$, Cl, F, NH$_2$, NH(C$_1$–C$_3$)alkyl, —N(R')CO(C$_1$–C$_3$)alkyl, —N(R')(R'), NO$_2$, —CONH$_2$, —SO$_2$NH$_2$, —SO$_2$N(R')(R'), —N(R') COCH$_2$O-(C$_1$–C$_3$)alkyl, wherein R' is (C$_1$–C$_3$)alkyl or hydrogen;

R$_4$ is (C$_1$–C$_6$)alkyl-O—, (C$_1$–C$_6$)alkyl-S—,

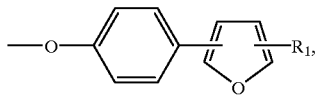

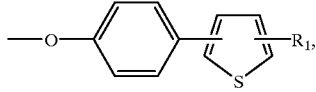

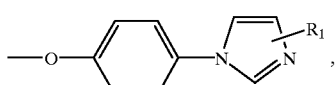

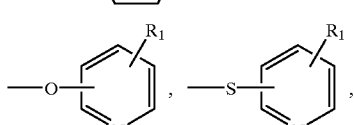

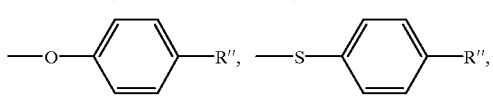

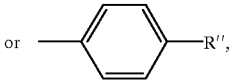

or

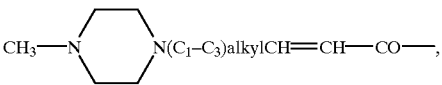

wherein R" is hydrogen, halogen, cyano, methyl or —OCH$_3$;

R$_1$ and R$_2$ are each, independently, hydrogen or CH$_3$;

R$_3$ is

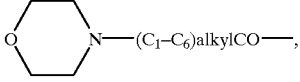

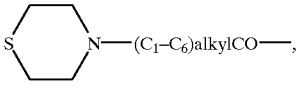

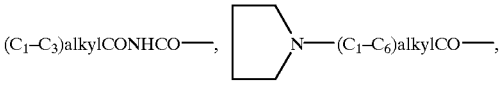

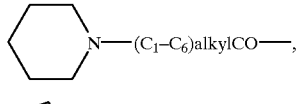

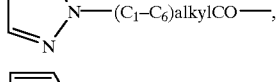

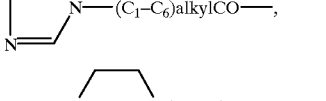

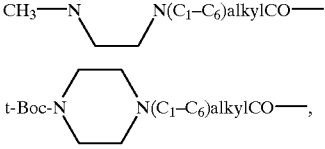

-continued

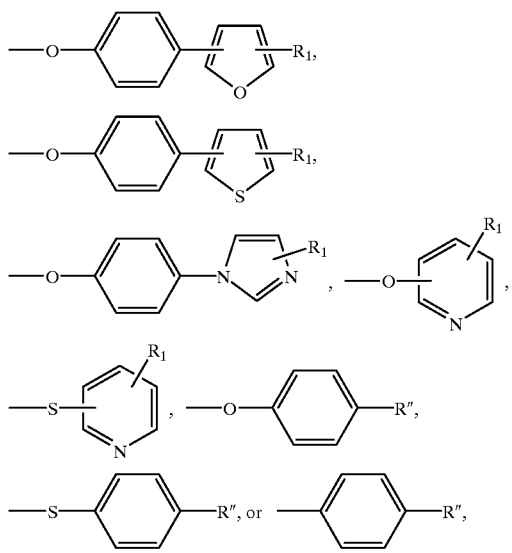

[(C$_1$-C$_6$)alkyl]$_2$—N—(C$_1$-C$_6$)alkyl CO—, or (C$_1$-C$_6$) alkyl-NH—(C$_1$-C$_6$)alkylCO—, wherein R' is as defined above; and pharmaceutically acceptable salts thereof.

It is more preferred that the compounds of the present invention include those of formula 1 wherein R is hydrogen, (C$_1$-C$_3$)alkyl, —CN, —OR', —SR', —CF$_3$, —OCF$_3$, Cl, F, NH$_2$, NH(C$_1$-C$_3$)alkyl. —N(R')CO(C$_1$-C$_3$)alkyl, —N(R')(R'), NO$_2$, —CONH$_2$, —SO$_2$NH$_2$, —SO$_2$N(R')(R'), or —N(R')COCH$_2$O-(C$_1$-C$_3$)alkyl, wherein R' is (C$_1$-C$_3$)alkyl or hydrogen;

R$_4$ is (C$_1$-C$_6$)alkyl-O—, (C$_1$-C$_6$)alkyl-S—,

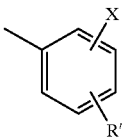

wherein R" is hydrogen, halogen, cyano, methyl or —OCH$_3$;

R$_1$ and R$_2$ are each, independently hydrogen or CH$_3$;

R$_3$ is (C$_1$-C$_3$)alkylSO$_2$—, Aryl(CH$_2$)$_n$SO$_2$—, Heteroaryl (CH$_2$)$_n$SO$_2$—, or (C$_1$-C$_3$)alkyl-O-(CH$_2$)$_m$—SO$_2$, wherein m=1 to 3; n=0 to 3;

Aryl is

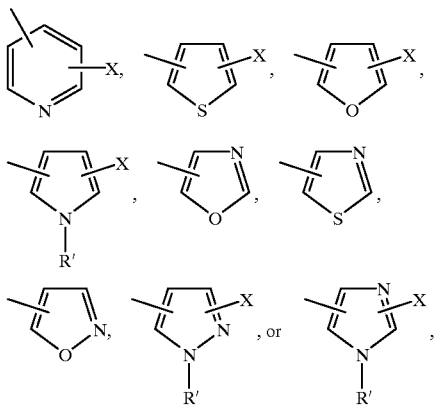

and
Heteroaryl is

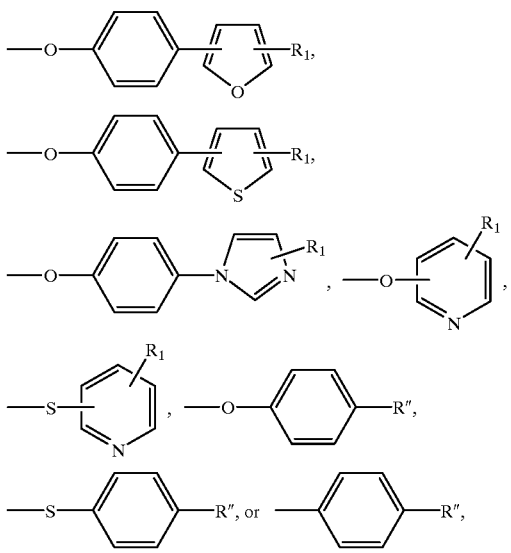

wherein X is hydrogen, halogen, (C$_1$-C$_3$)alkyl or —OCH$_3$ and R and R' are as defined above, and pharmaceutically acceptable salts thereof.

A further, more preferred embodiment of the present invention includes compounds represented by formula 1 wherein R is selected from hydrogen, (C$_1$-C$_3$)alkyl, —CN, —OR', —SR', —CF$_3$, —OCF$_3$, Cl, F, NH$_2$, NH(C$_1$-C$_3$)alkyl, —N(R')CO(C$_1$-C$_3$)alkyl, —N(R')(R'), NO$_2$, —CONH$_2$, —SO$_2$NH$_2$, —SO$_2$N(R')(R'), or —N(R')COCH$_2$O-(C$_1$-C$_3$) alkyl, wherein R' is (C$_1$-C$_3$)alkyl or hydrogen;

R$_4$ is (C$_1$-C$_6$)alkyl-O—, (C$_1$-C$_6$)alkyl-S—, wherein R" is hydrogen, halogen, cyano, methyl or —OCH$_3$;

R$_1$ and R$_2$ are each, independently hydrogen or CH$_3$;

$R_3$ is $(C_1-C_8)$alkyl, Aryl$(C_1-C_3)$alkyl, Heteroaryl$(C_1-C_3)$alkyl, ArylCH=CHCH$_2$, HeteroarylCH=CHCH$_2$—, or $(C_1-C_6)$alkylCH=CHCH$_2$—, wherein Aryl is

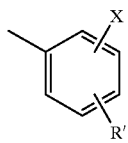

and

Heteroaryl is

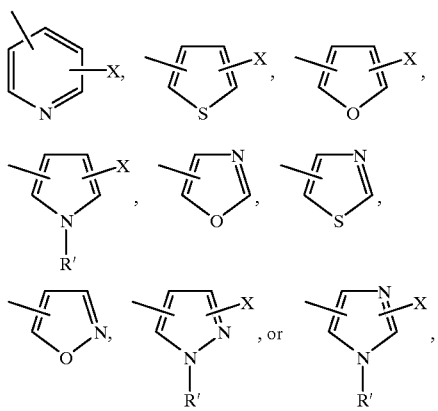

wherein X is hydrogen, halogen, $(C_1-C_3)$alkyl or —OCH$_3$ and R and R' are as defined above; and pharmaceutically acceptable salts thereof.

Additionally preferred compounds of the present invention include those of formula 1 wherein R is hydrogen, $(C_1-C_3)$alkyl, —CN, —OR', —SR', —CF$_3$, —OCF$_3$, Cl, F, NH$_2$, NH$(C_1-C_3)$alkyl, —N(R')CO$(C_1-C_3)$alkyl, —N(R')(R'), NO$_2$, —CONH$_2$, —SO$_2$NH$_2$, —SO$_2$N(R')(R'), or —N(R')COCH$_2$O-$(C_1-C_3)$alkyl, wherein R' is $(C_1-C_3)$ alkyl or hydrogen, $R_4$ is $(C_1-C_6)$alkyl-O—, $(C_1-C_6)$alkyl-S—.

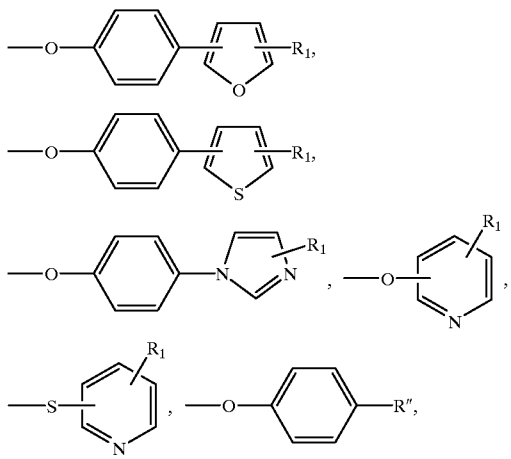

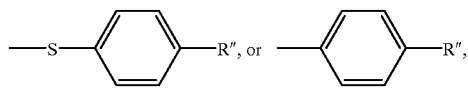

wherein R" is hydrogen, halogen, cyano, methyl or —OCH$_3$;

$R_1$ and $R_2$ are each. independently hydrogen or CH$_3$, $R_3$ is

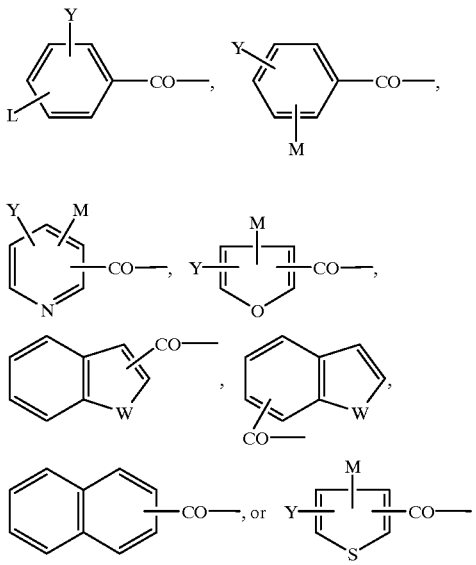

wherein m=1 to 3; n=0 to 3;

L is hydrogen, $(C_1-C_3)$alkyl, —CN, —OR', —SR', —CF$_3$, —OCF$_3$, Cl, F, NH$_2$, —NH—$(C_1-C_3)$alkyl, —N(R')CO$(C_1-C_3)$alkyl, N(R')(R'), —NO$_2$, —CONH$_2$, —SO$_2$NH$_2$, —SO$_2$N(R')(R'), —N(R')COCH$_2$O-$(C_1-C_3)$alkyl,

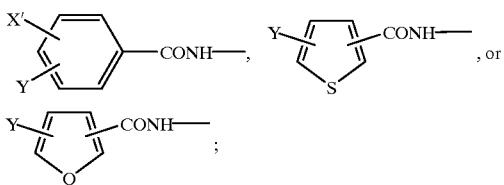

M is

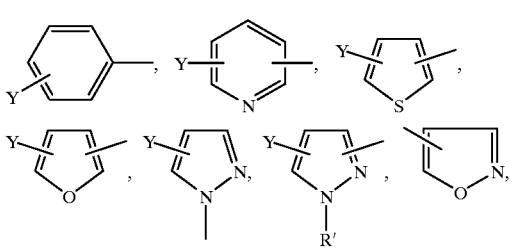

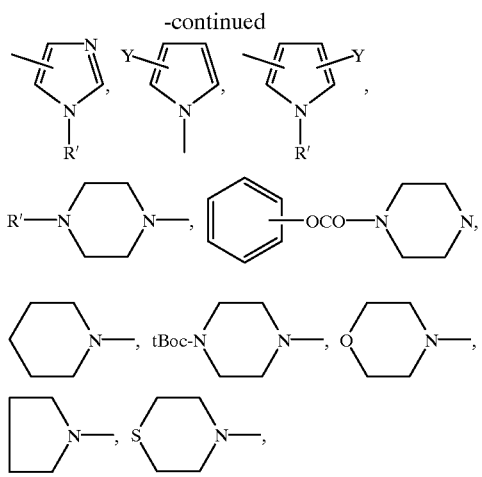

or N(R')(R') where R' is as defined above;

W is O, S, NH or N(C$_1$–C$_3$)alkyl;

Y is hydrogen, F, Cl, CF$_3$ or OCH$_3$; and X' is halogen, hydrogen, (C$_1$–C$_3$)alkyl, O-(C$_1$–C$_3$)alkyl, or —CH$_2$OH; and pharmaceutically acceptable salts thereof.

The compounds of formula 1 may be advantageously prepared according to Reaction Schemes 1 to 7. Variations in these schemes may be made to improve productivity without negatively impacting the amount and nature of the product, by means that will be recognized by those skilled in the art. For example, reactive groups may be blocked with suitable blocking moieties which may then be deblocked under standard conditions (for instance, hydroxy groups may be protected with trimethylsilyl or t-butyl-dimethylsilyl moieties which are then removed in a later reaction step).

In general, the compounds of Formula 1 are synthesized from an alkyl ester (such as methyl, ethyl, t-butyl and the like) of serine, threonine, or 3,3-dimethyl-3-hydroxypropionic acids. One reaction pathway is shown in Reaction Scheme 1. It is noted that methyl esters are shown in all of the Reaction Schemes, however, it is to be understood that the use of methyl esters is for purposes of illustration only, and other suitable alkyl esters or benzyl esters may similarly be used.

In Reaction Scheme 1, serine, threonine, beta-hydroxyvaline and related derivatives are converted to the corresponding N-(4-substituted-benzenesulfonyl) derivatives 3 and alkylated with suitable substituted or unsubstituted 2-nitrobenzyl bromides or 2-nitrobenzyl chlorides to provide the corresponding nitro derivatives 5. Reduction under conventional reducing conditions, such as catalytic hydrogeneration (with Pd/C) or chemical reduction (e.g., with SnCl$_2$ or FeCl$_3$) results in amino derivatives 6. Reaction of the N-(2-aminobenzyl) derivatives 6 with alkanoyl chlorides, alkylsulfonyl chlorides, aroyl chlorides, heteroaroyl chlorides, aryl sulfonyl chlorides, heteroarylsulfonyl chlorides and the like, in the presence of trialkylamines or pyridene, provides the dihydroalanine derivatives 7. Ring closure to the [1,4]benzodiazepine compounds 9 is carried out by reaction with a mild base such as sodium or potassium bicarbonate in an alcohol solvent such as methanol or ethanol. Standard conditions which involve hydrolysis of the ester (NaOH), acid chloride formation and reaction of the acid chloride with hydroxylamine are then used to convert the ester derivatives 8 to the hydroxamic acids 9. Ester derivatives 8 (where the ester function is a t-butyl ester) are converted to the acid with trifluoroacetic acid under standard conditions.

As illustrated in Reaction Scheme 2, derivatives 10, which contain a blocked hydroxyl group, are alkylated with 2-nitro or 2-amino benzyl alcohol derivatives 11 by application of the Mitsunobu reaction to give intermediates 12. Reduction of the 2-nitro group and removal of the hydroxy blocking group with derivatives 12, where the R$_4$ group is a protected amino moiety with simultaneous deblocking of the amino and hydroxyl functions, gives intermediate compounds 13. The intermediate 13 may then be reacted with benzyloxycarbonyl chloride to give the closed ring [1,4] benzodiazepine 14. Reaction of this compound with acyl chlorides, aroyl chlorides, heteroaroyl chlorides, alkysulfonyl chlorides, arylsulfonyl chlorides and heteroarylsulfonyl chlorides and the like results in the intermediates 15.

Scheme 1

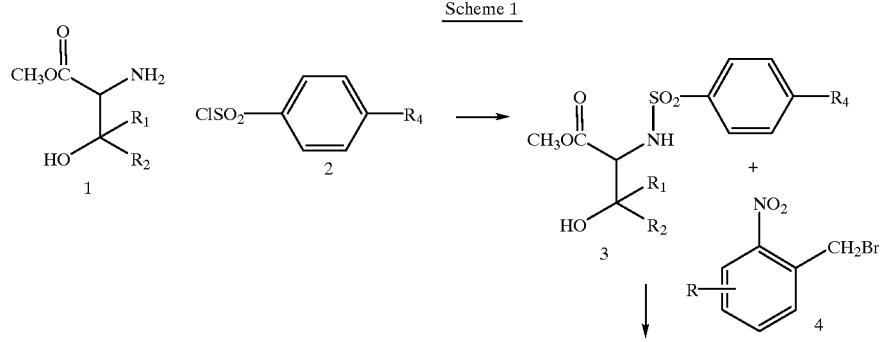

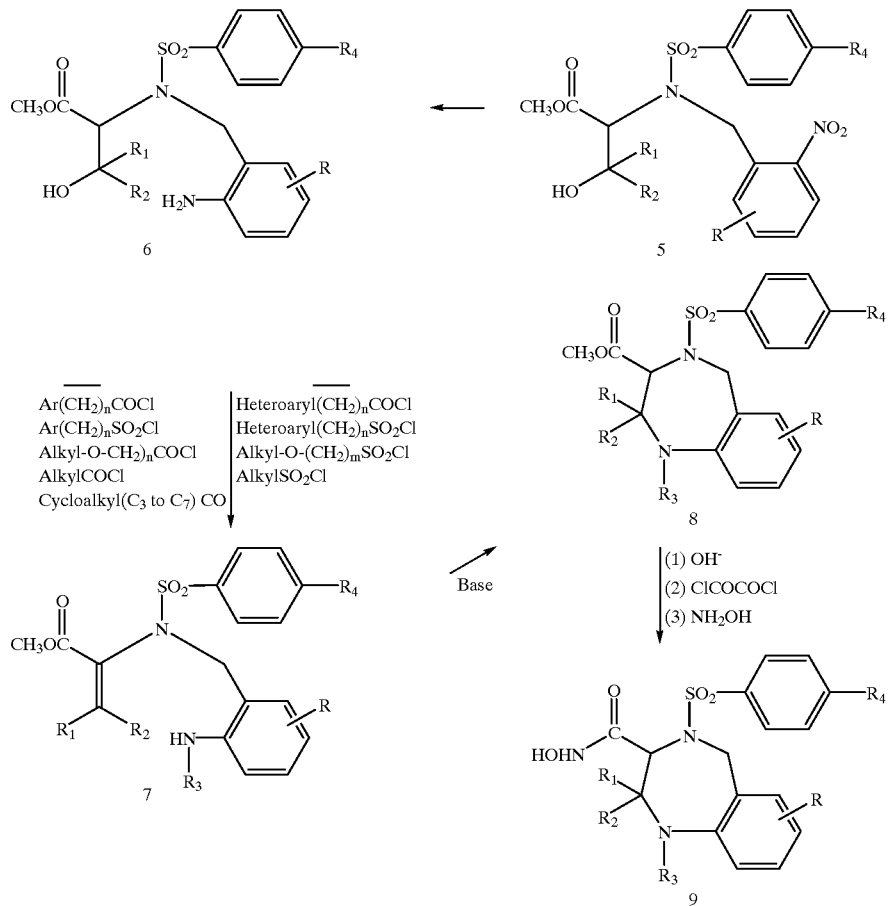

wherein
  n=0 to 3;
  m=1 to 3;
  $R_1$=($C_1$–$C_3$)alkyl; R=Hydrogen; halogen; $OCH_3$; $NO_2$; $NH_2$; $CF_3$; $NHCOCH_3$; $NHCOCH_2OCH_3$; $CONH_2$; —N(R')(R'), —N(R')CO($C_1$–$C_3$)alkyl; ($C_1$–$C_3$)alkyl; $R_3$=Ar($CH_2$)$_n$CO—; Heteroaryl($CH_2$)$_n$CO—, Ar($CH_2$)$_n$$SO_2$—; Heteroaryl($CH_2$)$_n$$SO_2$—; Alkyl-O—($CH_2$)$_n$CO—; Alkyl-O-($CH_2$)$_m$$SO_2$—; AlkylCO—; AlkylSO$_2$—; AlkylCO—NHCH$_2$CO—; and cycloalkyl($C_3$–$C_7$)CO—; and $R_4$ is as defined herein.

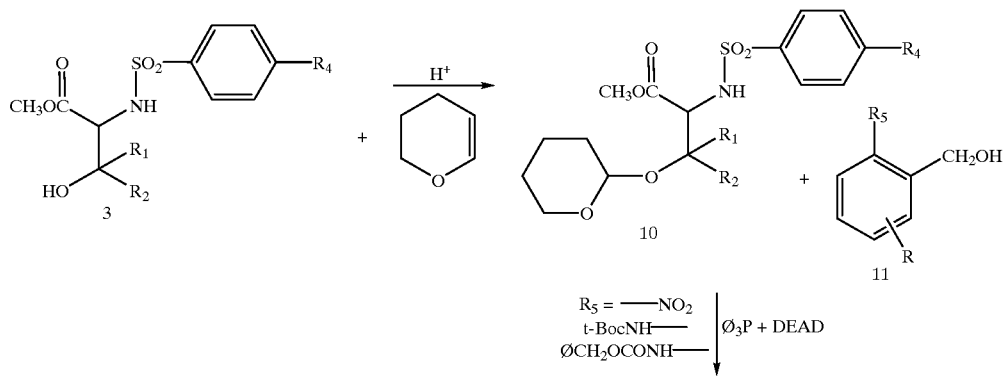

Scheme 2

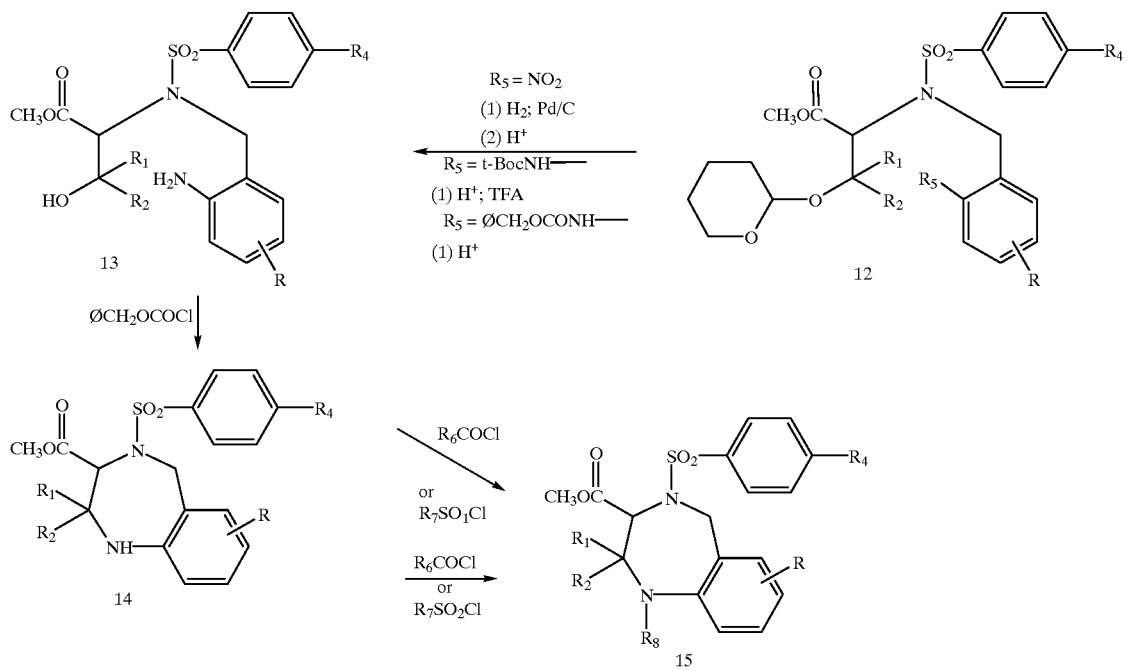

wherein
n=0 to 3;
m=1 to 3;
Ø=phenyl;
DEAD=diethylazodicarboxylate;
$R_6$=Ar$(CH_2)_n$—; Alkyl-; Heteroaryl$(CH_2)_n$—; Alkyl-O-$(CH_2)_n$—; Cycloalkyl$(C_3-C_7)$;
$R_7$=Ar$(CH_2)_n$—; Alkyl-; Heteroaryl$(CH_2)_n$—; Alkyl-O-$(CH_2)_m$—;
$R_8$=Ar$(CH_2)_n$CO—; Ar$(CH_2)_n$SO$_2$—; AlkylCO—; AlkylSO$_2$—; Heteroaryl$(CH_2)_n$CO—; Heteroaryl$(CH_2)_n$SO$_2$—; Alkyl-O-$(CH_2)_n$CO—; Alkyl-O-$(CH_2)_m$SO$_2$—.

1-substituted arylmethyl-2,3,4,5-tetrahydro-1H [1,4]-benzodiazepines may be prepared in the manner illustrated in Reaction Schemes 3 and 4. In Reaction Scheme 3, the methyl 3-hydroxy-2-[4-methoxybenzenesulfonyl]-(2-aminobenzyl)amino]-propionates 6 are subjected to reductive alkylation with arylcarboxaldehydes and heteroarylcarboxaldehydes to provide intermediates 17. Standard reaction conditions such as reactions with triphenylphosphine and diethyl azodicarboxylate (DEAD) or triplenylphosphine with either carbon tetrachloride or carbon tetrabromide, results in the "dehydroalanine" derivatives 18 which are then ring closed to the [1,4]benzodiazepines 20.

In an alternative route to the 3-hydroxamic acid derivatives 21(Scheme 4), N-aroyl derivatives 22 are reduced with reducing agents such as borane or lithium aluminum hydride to reduce both the ester and amide functions. The 3-(hydroxymethyl)-1-(arylmethyl)-2,3,4,5-tetrahydro-1H-[1,4]benzodiazepine 23 are oxidized with stardard reagents known to convert a hydroxymethyl group to a carboxylic acid:reagents such as NaIO$_4$ with catalyst RuO$_2$ (e.g., see *J. Org. Chem.*, 46:3936 (1981); Synlett, p. 143, (1996)). Coupling the acids (via the acid chlorides) to hydroxylamine then gives products 21. Certain intermediates as exemplified by formula 25 may be reduced with borane under mild conditions to give derivatives 25a in which the amide carbonyl is selectively reduced. These intermediates 25a are then converted to hydroxamic acid derivatives via hydrolysis of the ester to the acid and coupling the acid chloride with hydroxylamine.

Scheme 3
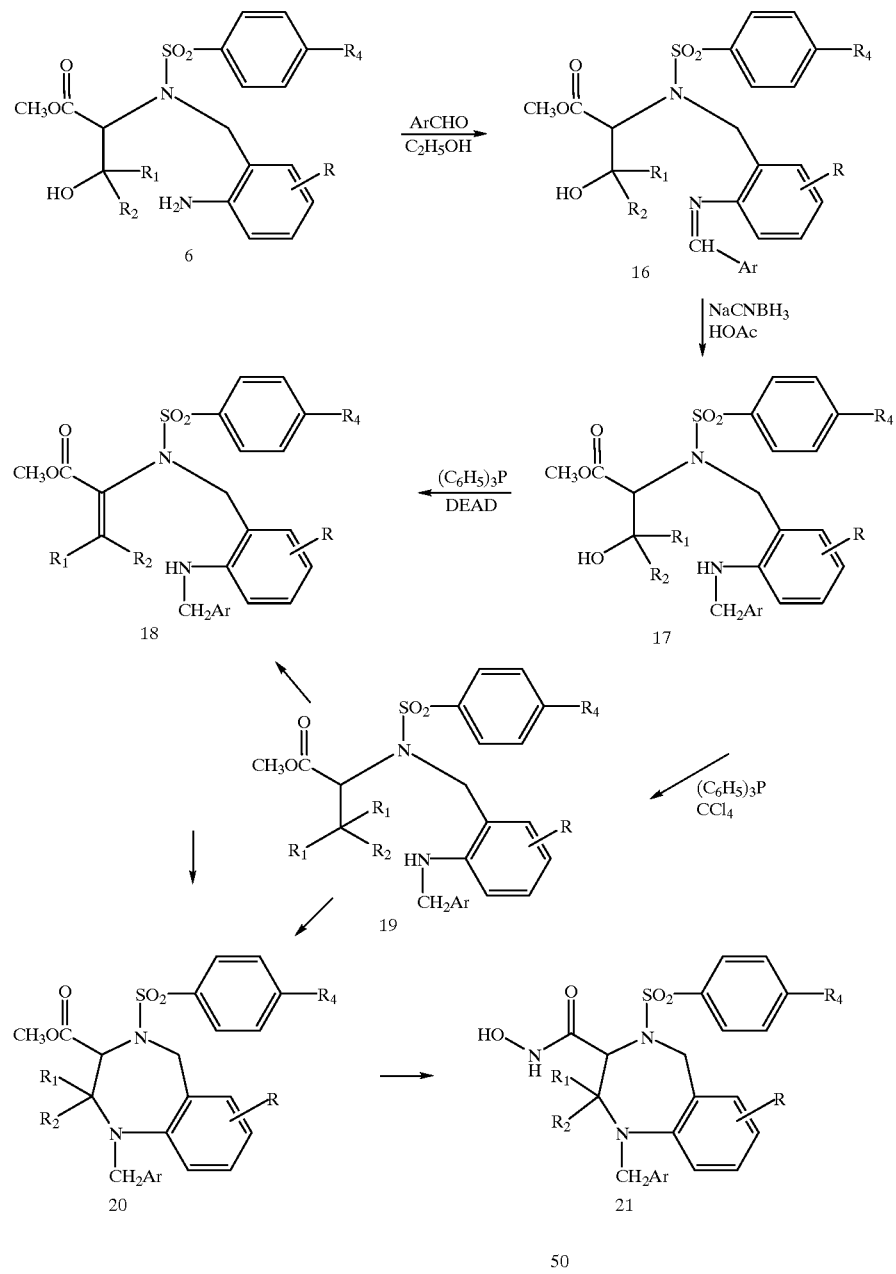
wherein
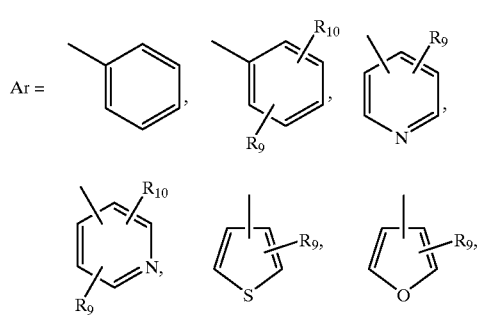
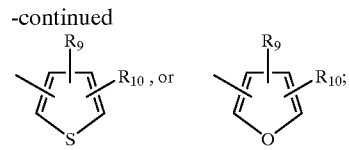
and $R_9$ and $R_{10}$ are: Cl, Br, F, $OCH_3$, OEt, $SCH_3$,
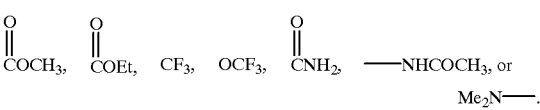

Scheme 4

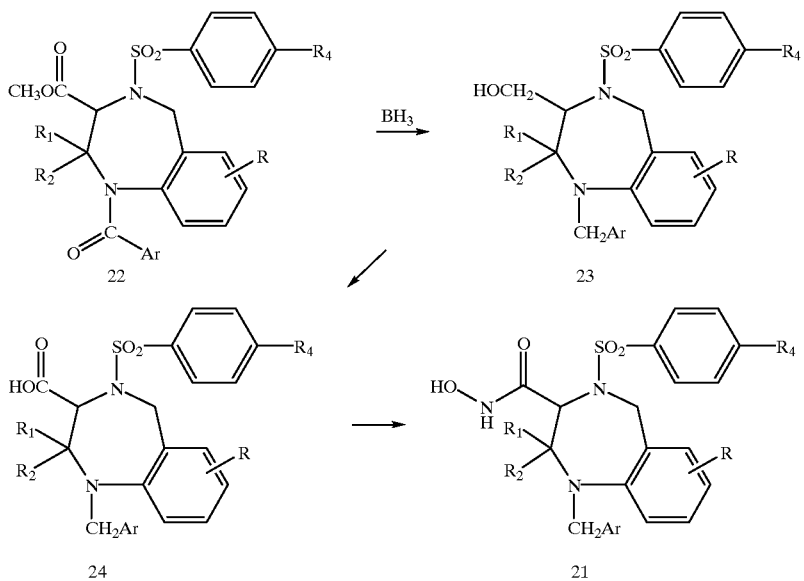

wherein

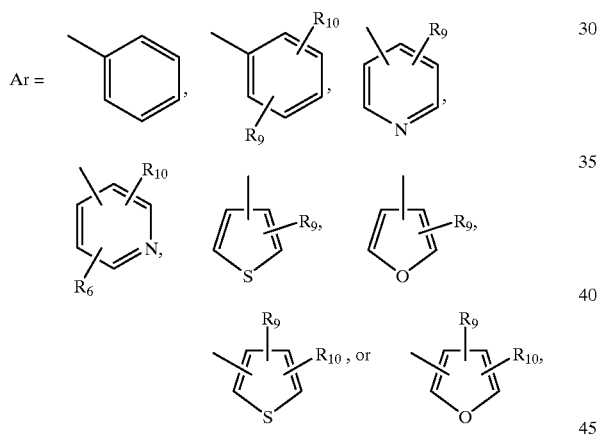

and $R_9$ and $R_{10}$ are hydrogen, Cl, Br, F, $OCH_3$, OEt, $SCH_3$,

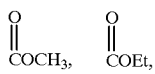

$CF_3$, $OCF_3$, or $Me_2N-$.

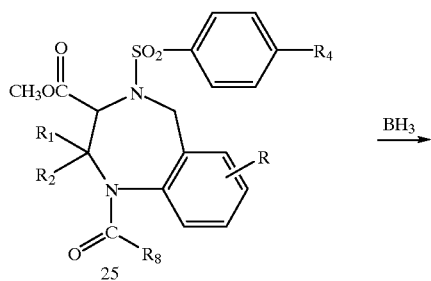

-continued

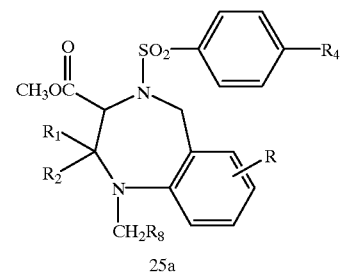

wherein $R_8$=alkyl, arylalkyl, aryloxyalkyl, heterocyclicalkyl, or alkyloxyalkyloxyalkyl.

Other, preferred compounds of the present invention are those with basic moieties in the 1-(substituted carbonyl) group which may be prepared in the manner shown in Reaction Scheme 5. Reaction of the 2,3,4,5-tetrahydro-1H-[1,4]-benzodiazepines 14 (without a substituent at the 1-position) with carbonyl chloride derivatives in the manner depicted in Reaction Scheme 5, results in intermediates 25 which are then converted to acid 26 and hydroxamic acids 27. The intermediates 25 may also be synthesized by reaction of methyl 2-[(2-aminobenzyl)-(4-methoxybenzenesulfonyl)amino]-3-hydroxypropionates 6 with acid chlorides to live "dehydroalanine" derivatives 28. As previously described, mild bases such as $NaHCO_3$ can be reacted with these derivatives to cause ring closure via a 1,4-addition to the double bond in intermediate 28 to provide the 7-membered 2,3,4,5-tetrahydro-1H-[1,4]diazepines 25.

Scheme 5
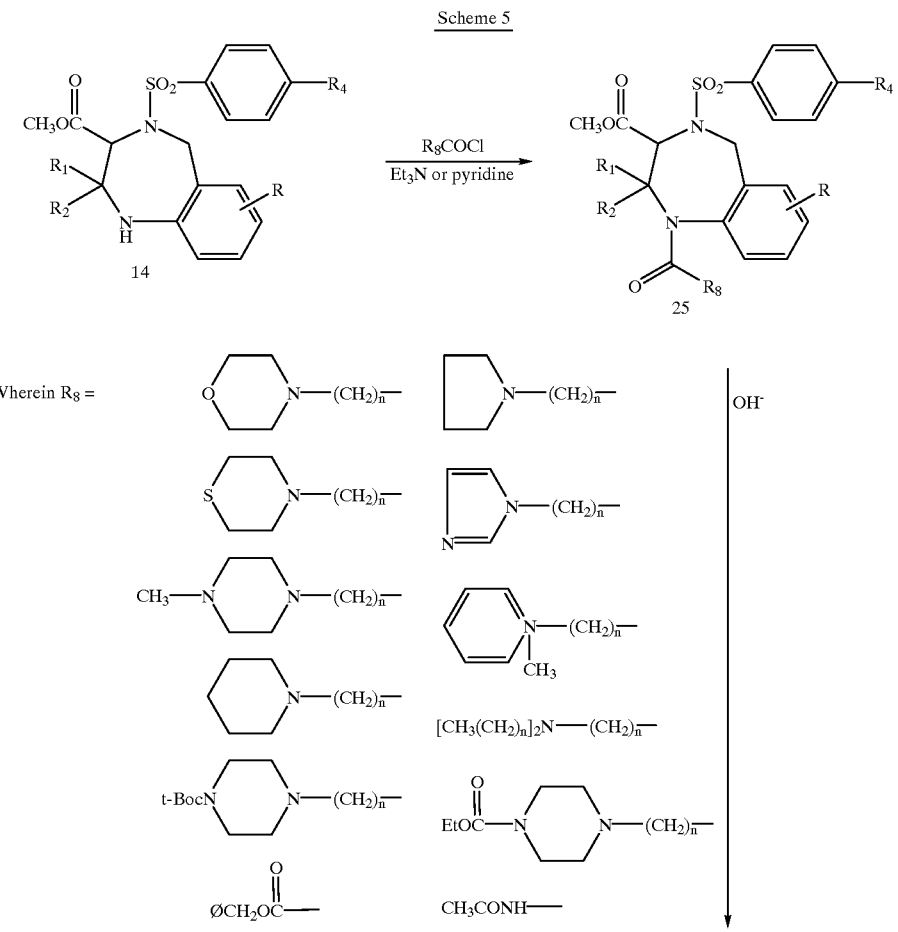
Wherein R$_8$ = 
and n = 0 to 3
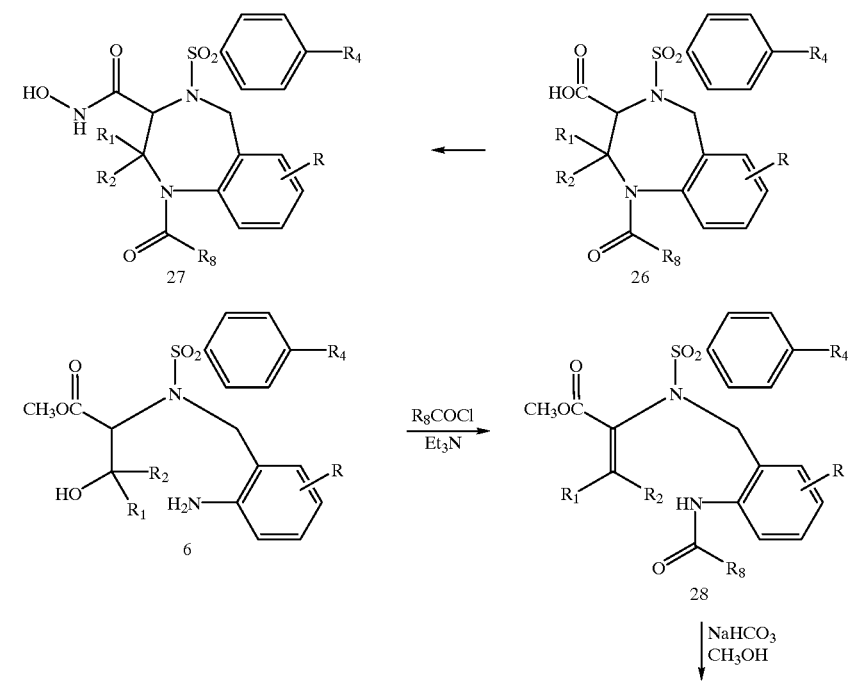

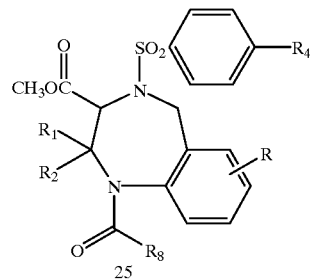

As illustrated in Reaction Scheme 6, aryl-arylcarbonyl, heteroaryl-arylcarbonyl, aryl-heteroarylcarbonyl, heteroaryl-heteroarylcarbonyl derivatives 30 may be synthesized by standard palladium catalysed coupling of bromoaroyl or bromheteroaroyl derivatives 29 with appropriate arylstannanes, heteroarylstannanes, arylboronic acids, heteroarylboronic acids, aryl triflates, heteroaryl triflates and the like, under known conditions. For example, see *Synthesis*, 563–566 (1997); *J. Org. Chem.*, 62:3405–3406, (1997); *Tetrahedron Lett.*, 36:5247–5250, (1995); *Heterocycles*, 45:467, (1997); *Tetrahedron Lett.*, 38:1118–1182, (1997); *Heterocycles*, 42:189–194, (1996); *Tetrahedron Lett.*, 5005–5006, (1993); *Synthesis*, 843, (1987); *Heterocycles*, 2711–2716, (1987); and *Tetrahedron Lett.*, 4407–4410, (1986).

By coupling with such palladium catalysts, aryl-aryl, heteroaryl-aryl, aryl-heteroaryl and heteroaryl-heteroaryl carboxylic ester derivatives can be prepared and these derivatives converted to carboxylic acid intermediates. The acids are then converted to acid chlorides which are reacted with esters of 2-[(2-aminobenzyl)-(4-substituted-benzenesulfonyl)amino]-3-hydroxypropionate as illustrated for conversion of derivatives 6 to intermediates 31. The following references describe procedures for the synthesis of methyl 3-arylpyrrole-4-carboxylates as in *J. Org. Chem.*, 62:2649–2651, (1997); methyl (2-methylphenyl)benzoates as in *J. Org. Chem.*, 62:3405–3406, (1997); and methyl benzoates substitued with heterocyclic moieties such as furanyl, thienyl or pyridinyl groups as in *Tetrahedron Lett.*, 27:4407–4410, (1986).

Scheme 6

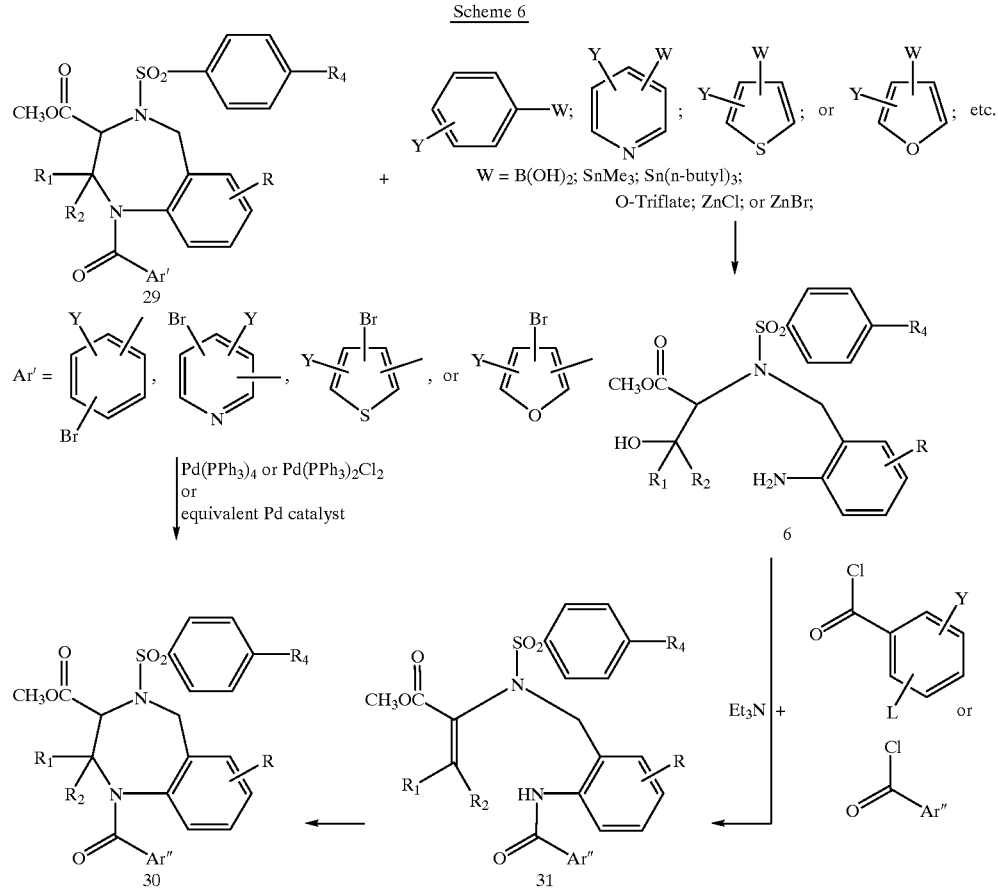

where

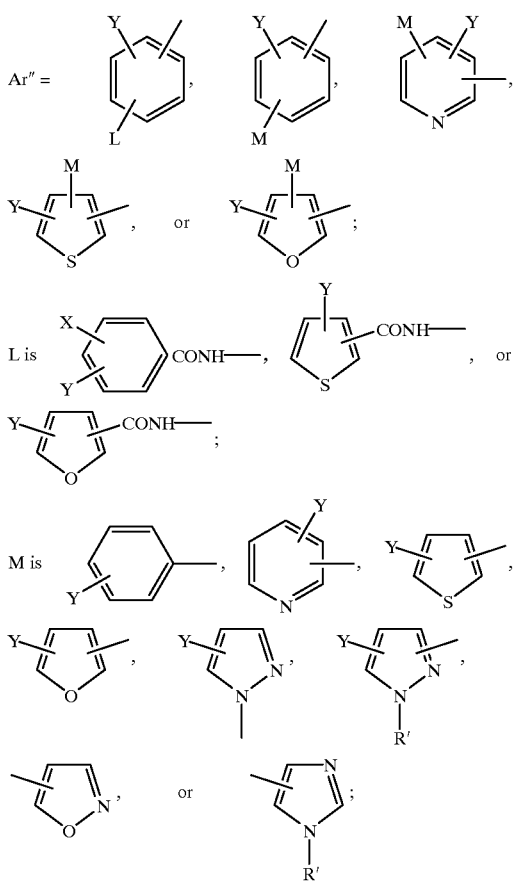

Y is H, F, Cl, $CF_3$, $CH_3$, or $OCH_3$;

X is halogen, hydrogen, or $(C_1-C_3)$alkyl;

R and R' are as defined herein; and $R_4$ is as defined herein.

The intermediates 2,4,5,6-tetrahydro-1H-[1,4] benzodiazepines 39 and 38 may be prepared from glycine esters in the manner exemplified in Reaction Scheme 7. In this synthetic route, N-(4-substituted-benzenesulfonyl) derivatives of glycine ethyl ester, glycine t-butyl ester or glycine methyl ester 33 are alkylated with a substituted (R) or unsubstituted (R=H) 2-nitrobenzyl bromide in N,N-dimethylformamide or 1-methyl-2-pyrrolidinone in the presence of potassium carbonate to give intermediates 34. Alternatively, the esters of N-(4-substituted-benzenesulfonyl) glycines, such as the methyl ester 33. are first reacted with sodium hydride in N,N-dimethylformamide or 1-methyl-2-pyrrolidinone and the resulting anion reacted with substituted or unsubstituted 2-nitrobenzylbromides to provide compounds 34. Reaction of derivates 34 with N,N-dimethyl(methylene)ammonium chloride or the iodide salts under standard reaction conditions (e.g., as set forth in *Fieser and Fieser*, 10:160–161; 8:194 affords the dimethylaminomethyl (Mannich type) compounds as intermediates for elimination to the "dehydroalanine" derivatives 37 or direct ring closure of 36 to 39 via an elimination-addition reaction. Ring closure of compounds 37 provides intermediates 38 for conversion to hydroxamic acids. Variations of the reactions conditions for conversion of 36 to 39 involve heating in the presence of Lewis acids, such as $BF_3$ or heating an acid salt of 36 to effect the elimination-addition reaction.

Scheme 7

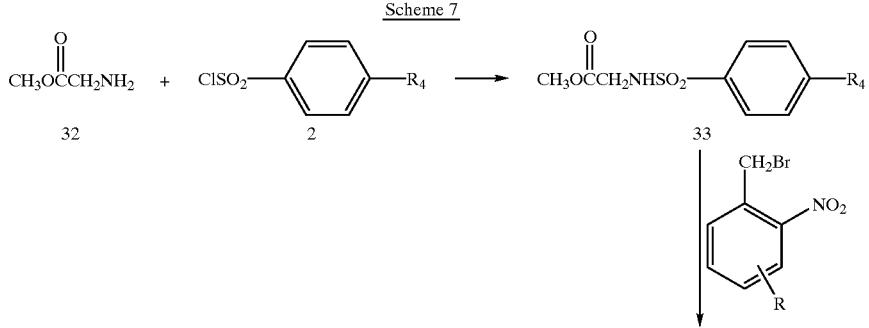

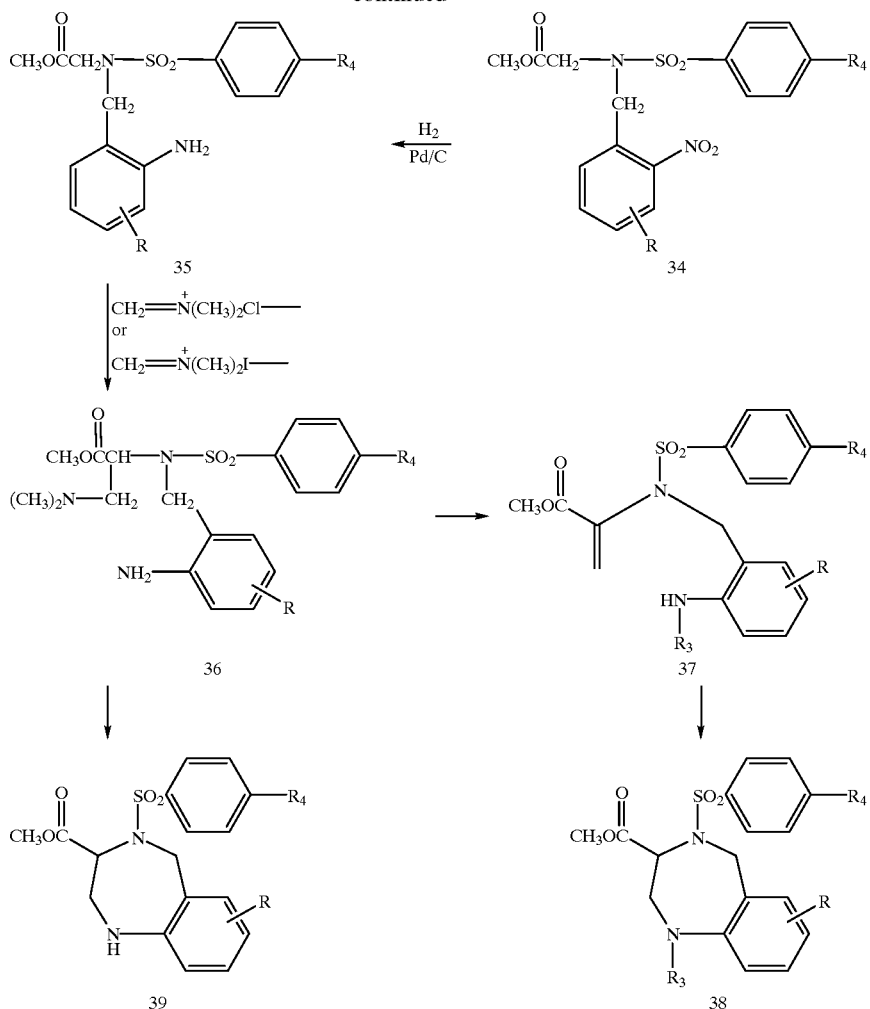

The intermediate carboxylic acids for conversion to the tetrahydro[1,4]benzodiazepine-3-carboxylic acid, hydroxyamides may be synthesized via different routes as shown in Schemes 1–8. For the synthesis of some of the desired products of Formula 1, alternate routes may be preferred as shown in Scheme 8. Under these conditions, intermediate carboxylate esters of Intermediate 41 or acids of Intermediate 44 wherein the $R_4$ substituent is an OH group are prepared. Intermediates with $R_4$ an OH group may be prepared from derivatives wherein the OH group is protected by a croup which can be selectively removed. Derivatives 40 wherein $R_4$ is an $OCH_3$ moiety are suitable precursors to the desired phenolic compounds 41 and 44 through cleavage of the oxygen methyl bond. As shown in Scheme 8, the anion of the phenolic OH group may be prepared in situ and then alkylated. Suitable bases are alkaline metal carbonates, hydrides, alkoxides and organic bases. Reaction with an alkylating moiety represented by the Formula $(C_1–C_6)$alkyl-X wherein X is a reactive leaving group such as a chloride, bromide, iodide, O-mesylate of an O-tosylate gives the derivatives 42 and 45.

The alkylation reaction may be carried out with caboxylate esters such as 41 or with the carboxylic acids such as 44. Alternatively, the phenolic compounds 41 and 44 may be reacted under Mitsunobe Reaction conditions to afford the O-alkylated derivatives 42 and 45. Standard Mitsunobe Reaction conditions, such as those described in the following literature references, may be used in the coupling reactions: *J. Heterocyclic Chem.* 34:349 (1997); *Tetrahedron Lett.* 37:6439 (1996); *J. Org. Chem.,* 56:7173 (1991); *Tetrahedron Lett.* 5709 (1989); *Synthesis* 1:28 (1981).

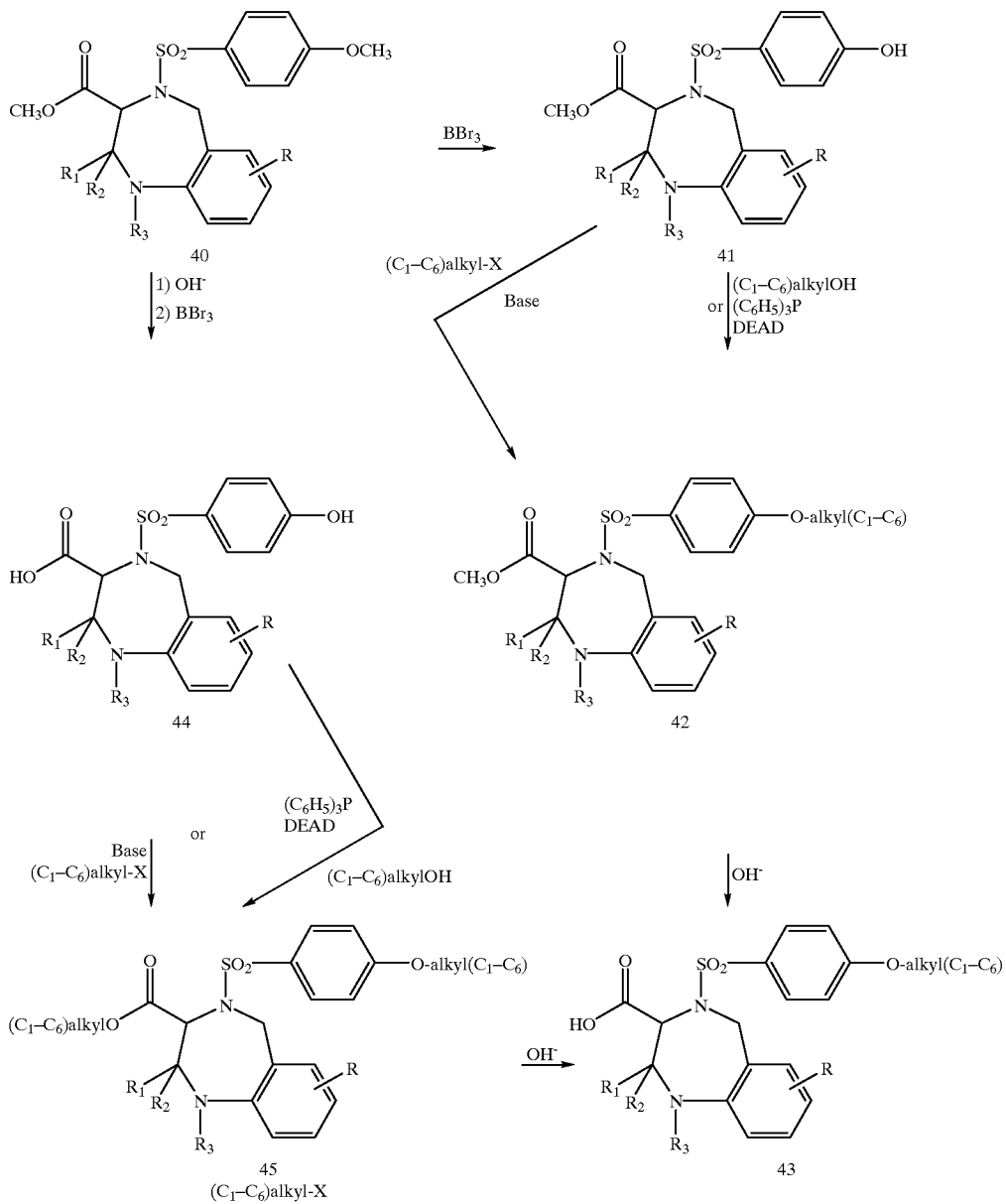

Scheme 8

The compounds of the present invention which have a basic moiety may be used in the form of salts derived from pharmaceutically or physiologically acceptable acids. These salts include, but are not limited to, salts with inorganic acids (such as hydrochloric acid, sulfuric acid, nitric acid, phosphoric acid) or organic acids (such as acetic acid, oxalic acid, succinic acid, and maleic acid). Other salts of compounds with an acidic moiety include those with alkali metals or alkaline earth metals (such as sodium, potassium, calcium, and magnesium) or organic bases.

When the present compounds are utilized in pharmaceutical compositions, they may be combined with one or more pharmaceutically acceptable carriers, e.g., solvents, diluents and the like. Such compositions containing the present compounds may be administered orally, in the form of tablets, capsules, dispersible powders, granules, suspensions, syrups or elixirs; parentally, in the form of a sterile injectable solution or suspension; or topically, in the form of creams, lotions, ointments, etc. Such pharmaceutical compositions may contain from about 1 to about 100 mg of active ingredient in combination with the carrier.

The effective dosage of the present compounds utilized to treat a specific condition will vary depending upon the particular compound employed, the mode of administration and the type and severity of the condition being treated. However, in general, satisfactory results are obtained when the present compounds are administered at a dosage of about 0.001 to 1000 mg/kg of body weight.

As noted above, the compounds of the present invention may be administered orally, as well as by intravenous. intramuscular, subcutaneous or topical routes. Solid carriers useful for preparing tablets, capsules, etc., include starch, lactose, dicalcium phosphate, microcrystalline cellulose, sucrose and kaolin. Liquid carriers useful for preparing compositions of the present compounds include sterile water, polyethylene, glycols, non-ionic surfactants, and edible oils such as corn, sesame, and peanut oils. Adjuvants conventionally used in the preparation of pharmaceutical compositions may also be included, such as flavoring agents, coloring agents, preservatives and antioxidants.

The compounds of the present invention were tested for biological activity according to the following procedures.

In Vitro Gelatinase Assay

The assay is based on the cleavage of the thiopeptide substrate ((Ac-Pro-Leu-Gly(2-mercapto-4-methylpentanoyl)-Leu-Gly-OEt), available from Bachem Bioscience) by the enzyme gelatinase, releasing the substrate product which reacts calorimetrically with DTNB ((5,5'-dithio-bis(2-nitro-benzoic acid)). This assay is disclosed in Weingarten et al., "Spectrophotometric Assay for Vertebrate Collegenase", *Anal. Biochem.*, 147:437–440, (1985). The enzyme activity is measured by the rate of the color increase.

The thiopeptide substrate was made up fresh as a 20 mM stock in 100% DMSO and the DTNB was dissolved in 100% DMSO as a 100 mM stock and stored in the dark at room temperature. The substrate and the DTNB were diluted together to 1 mM with substrate buffer (50 mM HEPES, pH 7.5, 5 mM $CaCl_2$) before use. The stock of human neutrophil gelatinase B was diluted with assay buffer (50 mM HEPES, pH 7.5, 5 mM $CaCl_2$, 0.02% Brij) to a final concentration of 0.15 nM.

The assay buffer, enzyme. DTNB/substrate (500 μM final concentration) and vehicle or inhibitor were added to a 96 well plate (total reaction volume of 200 μl) and the increase in color was monitored spectrophotometrically for 5 minutes at 405 nm on a plate reader.

The increase in $OD_{405}$ was plotted and the slope of the line was calculated. The slope represents the reaction rate. The linearity of the reaction rate was confirmed ($r^2>0.85$) and the mean (x±sem) of the control rate was calculated and compared for statistical significance (p<0.05) with drug-treated rates using Dunnett's multiple comparison test. Dose-response relationships were generated using multiple doses of drug and $IC_{50}$ values with 95% CI were estimated using linear regression (IPRED, HTB).

In Vitro Collagenase Assay

This assay was based on the cleavage of a peptide substrate ((Dnp-Pro-Cha-Gly-Cys(Me)-His-Ala-Lys(NMa)-$NH_2$), available from Peptide International, Inc.) by collagenase releasing the fluorescent NMa group which was quantitated on the fluorometer as disclosed in Bickett et al., "A High Throughput Fluorogenic Substrate for Interstitial Collagenase (MMP-1) and Gelatinase (MMP-9)", *Anal. Biochem.*, 212:58–64, (1993). Dnp quenches the NMa fluorescence in the intact substrate.

The assay was run in HCBC assay buffer (50 mM HEPES, pH 7.0, 5 mM $Ca^{+2}$, 0.02% Brij, 0.5% Cysteine), with human recombinant fibroblast collagenase (truncated, mw=18,828. from Wyeth-Ayerst Research, Radnor, Pa.). The substrate was dissolved in methanol and stored frozen in 1 mM aliquots. Collagenase was stored frozen in buffer in 25 μM aliquots. In conducting the assay, the substrate was dissolved in HCBC buffer to a final concentration of 10 μM and collagenase to a final concentration of 5 nM. The compounds being examined were dissolved in methanol, DMSO, or HCBC. The methanol and DMSO were diluted in HCBC to <1.0%. The compounds were added to a 96 well plate containing enzyme and the reaction was started by the addition of substrate.

The reaction was read (excitation 340 nm, emission 444 nm) for 10 min. and the increase in fluorescence over time was plotted as a linear line. The slope of the line was calculated representing the reaction rate. The linearity of the reaction rate was confirmed ($r^2>0.85$). The mean (x±sem) of the control rate was calculated and compared for statistical significance (p<0.05) with drug-treated rates using Dunnett's multiple comparison test. Dose-response relationships were generated using multiple doses of drug and $IC_{50}$ values with 95% CI were estimated using linear regression.

Procedure for Measuring TACE Inhibition

In a 96-well black microtiter plate, each well received a solution composed of 10 μL TACE (available from Immunex) at a final concentration of 1 μg/mL, 70 μL Tris buffer, have a pH of 7.4 and containing 10% glycerol (final concentration 10 mM), and 10 μL of test compound solution in DMSO (final concentration 1 μM, DMSO concentration<1%). The plates were incubated for 10 minutes at room temperature. The reaction was initiated by addition of a fluorescent peptidyl substrate (final concentration 100 μM) to each well with shaking on a shaker for 5 sec.

The reaction was read (excitation 340 nm, emission 420 nm) for 10 min. and the increase in fluorescence over time was plotted as a linear line. The slope of the line was calculated and this represents the reaction rate. The linearity of the reaction rate was confirmed ($r^2>0.85$). The mean (x±sem) of the control rate was calculated and compared for statistical significance (p<0.05) with drug-treated rates using Dunnett's multiple comparison test. Dose-response relationships were generated using multiple doses of drug and $IC_{50}$ values with 95% CI were estimated using linear regression.

The results obtained following these standard experimental test procedures are presented in Table 1.

TABLE 1

[Structure: benzodiazepine core with HOHN-CO- attached to position bearing R1, R2; N-SO2-phenyl-R4; N-R3; ring R substituent]

| R3 | Compound of Example | R | R1 | R2 | R4 | MMP-1 | MMP-9 | MMP-13 | TACE |
|---|---|---|---|---|---|---|---|---|---|
| —SO2—C6H4—CH3 (p-tolylsulfonyl) | 2 | H | H | H | —OCH3 | — | 14.1 | 5.1 | 391 ± 12 |
| —SO2CH3 | 3 | H | H | H | —OCH3 | 156.5 | 7.9 | 3.0 | 104 ± 8 |
| —SO2CH2CH2CH3 | 10 | H | H | H | —OCH3 | 183 | 7.0 | 2.8 | 91 ± 10 |
| —SO2—C6H4—OCH3 | 4 | H | H | H | —OCH3 | 224.1 | 12.2 | 4.3 | 101 ± 3 |
| —COCH3 | 6 | H | H | H | —OCH3 | 18.4 | 1.4 | 1.0 | 103 ± 7 |
| —CO—C6H5 | 5 | H | H | H | —OCH3 | 15.8 (23) | 0.56 (1.7) | 0.4 (1.1) | 95 ± 10 |
| —CO-(3-pyridyl) | 7 | H | H | H | —OCH3 | 20.4 (34) | 0.6 (1.9) | 0.4 (1.3) | 77.7 ± 7 |
| —CO-(2-thienyl) | 8 | H | H | H | —OCH3 | 19.7 | 1.1 | 1.1 | 12.8 ± 1.2 |
| —CO-(4-pyridyl) | 13 | H | H | H | —OCH3 | 54.9 | 9.8 | 2.0 | 154 ± 27 |
| COCH2OCH3 | 9 | H | H | H | —OCH3 | 34.1 | 1.34 | 1.19 | 95.2 ± 14.8 |
| —CO(CH2)2—C6H5 | 12 | H | H | H | —OCH3 | 523 | 17.9 | 25.7 | 207 ± 21 |
| —CO—C6H4—CF3 (3-CF3) | 1 | H | H | H | —OCH3 | 96.2 | 5.1 | 3.7 | 352 ± 34 |
| —CO—C6H3(CH3)(F) (2-CH3, 4-F) | 11 | H | H | H | —OCH3 | 55.4 | 3.9 | 2.3 | 271 ± 20 |

TABLE 1-continued

[Structure: benzodiazepine core with HOHN-CO- group, R1, R2, R3 substituents on nitrogens, SO2-phenyl-R4 group, and R substituent on benzene ring]

| R3 | Compound of Example | R | R1 | R2 | R4 | MMP-1 | MMP-9 | MMP-13 | TACE |
|---|---|---|---|---|---|---|---|---|---|
| —CO—(4-biphenyl) | 15 | H | H | H | —OCH₃ | 52.7 | 0.7 | 0.4 | 199 ± 19 |
| —CO—(2-biphenyl) | 14 | H | H | H | —OCH₃ | 542 | 12.6 | 3.7 | 45% (1 uM) |
| —CO—(cyclopropyl) | 55 | H | H | H | —OCH₃ | 171 | 4.0 | 3.3 | 68.5 ± 7.2 |
| —CO—(cyclohexyl) | 57 | H | H | H | —OCH₃ | 465 | 12.7 | 7.2 | 318 ± 27 |
| —CO—(2,4-dichlorophenyl) | 31 | H | H | H | —OCH₃ | 75.5 | 3.0 | 2.6 | 36% (1 uM) |
| —CO—(2-furyl) | 40 | H | H | H | —OCH₃ | 16.6 | 1.4 | 1.2 | 28.5 ± 6.6 |
| —COCH₂O—phenyl | 58 | H | H | H | —OCH₃ | 65.5 | 4.4 | 2.9 | 154 ± 20 |
| —COCH₂OCH₃ | 59 | 7-CH₃ | H | H | —OCH₃ | 105 | 2.6 | 1.8 | 125 ± 6 |
| —CO—phenyl | 60 | 7-CH₃ | H | H | —OCH₃ | 22.7 | 1.4 | 1.3 | 143 ± 4 |
| —CO—(4-OCF₃-phenyl) | 61 | 8-Cl | H | H | —OCH₃ | 239 (265) | 1.3 (3.9) | 0.4 (4.3) | 1248 ± 69 |
| —CH₂CH₂OCH₃ | 62 | H | H | H | —OCH₃ | 1000 | 100 | 100 | 51 (1 μM) |

TABLE 1-continued

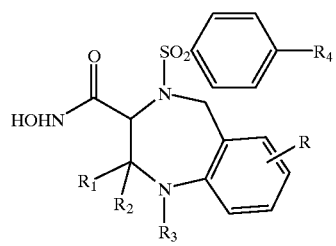

| R₃ | Compound of Example | R | R₁ | R₂ | R₄ | MMP-1 | MMP-9 | MMP-13 | TACE |
|---|---|---|---|---|---|---|---|---|---|
| (2-(1H-pyrazol-1-yl)phenyl)carbonyl | 63 | 7-CH₃ | H | H | —OCH₃ | 130 | 5.6 | 3.1 | 446 ± 48 |
| (2-morpholinophenyl)carbonyl | 64 | 8-Cl | H | H | —OCH₃ | 157 | 6.1 | 3.4 | 384 ± 8 |
| (4-ethoxyphenyl)carbonyl | 65 | H | H | H | —OCH₃ | 23.5 | 1.5 | 1.5 | 157 ± 13 |
| (3-chloro-4-(3-methylpyrazol-1-yl)phenyl)carbonyl | 66 | H | H | H | —OCH₃ | 83.4 | 3.4 | 2.6 | 148 ± 14 |
| —CH₂—phenyl | 67 | H | H | H | —OCH₃ | 1323 | 50.8 | 73.9 | 551 ± 29 |
| (2,4-dimethoxyphenyl)carbonyl | 71 | H | H | H | —OCH₃ | 41.3 | 2.4 | 1.3 | 136 ± 15 |
| —CO—CH₂—N(4-methylpiperazinyl) | 72 | H | H | H | —OCH₃ | 4982 | 187 | 317 | 808 ± 90 |

IC₅₀ (nM) column group header spans MMP-1, MMP-9, MMP-13, TACE.

The present invention will now be illustrated with reference to the following, non-limiting examples.

REFERENCE EXAMPLE 1

(L) N-(Benzyloxycarbonyl)-O-benzylserine, t-butyl ester

Into a solution of 25 g (0.076 mol) of N-(benzyloxycarbonyl)-O-benzylserine in 600 ml of $CH_2Cl_2$ cooled to −6° C. in an ice-salt bath was bubbled isobutylene, while 4.1 ml of concentrated sulfuric acid was added dropwise thereto. The mixture was stirred for 4 hours and worked up as described in *Synthetic Commun.*, 26:2723 (1996) to give 29.24 g of product as a yellow oil.

REFERENCE EXAMPLE 2

L-Serine, t-butyl ester

A mixture of 29.24 g (0.076 mol) of (L) N-(benzyloxycarbonyl)-O-benzylserine, t-butyl ester from Reference Example 1, 24.1 g (0.38 mol) of ammonium formate and 38.3 g of 10% palladium on carbon in 600 ml of methanol was heated at 65° C. for 20 hours and stirred at room temperature overnight. The mixture was filtered through diatomaceous earth and the filter pad was washed with methanol. The filtrate was concentrated to give 12.18 g (99.6%) of product as described in *Synthetic Commun.*, 26:2723 (1996).

REFERENCE EXAMPLE 3

N-(4-Methoxybenzenesulfonyl)-L-serine, t-butyl ester (3-hydroxy-2-(4-methoxybenzenesulfonylamino)propionic acid, tert-butyl ester)

To a solution of 12.18 g (0.0756 mol) of L-serine, t-butyl ester, 26.52 ml of triethylamine in 160 ml of $CH_2Cl_2$ (cooled in an ice bath) was added, in small portions, 16.1 g (0.0771 mol) of 4-methoxybenzene-sulfonyl chloride. The mixture was stirred at 0° C. for 0.5 hours and at room temperature overnight. The mixture was washed with $H_2O$, 2N citric acid, brine and dried with $Na_2SO_4$. The solvent was removed under vacuum to give 25.34 g of solid which was triturated with hexane. The solid was recrystallized from 120 ml of toluene to give 12.18 g (48.7%) of product as a white solid. The filtrate was concentrated and the residue chromatographed on silica gel with hexane-ethyl acetate (7:3) as eluent to give 5.71 g (22.8%) of white solid. m.p. 70–75° C. Anal. for $C_{14}H_{21}NO_6S$: Calc'd: C. 50.7; H,6.4; N,4.2; Found: C, 50.4; H,6.3; N,4.4.

REFERENCE EXAMPLE 4

3-Hydroxy-2-[(4-methoxybenzenesulfonyl)-(2-nitrobenzyl)amino]propionic acid, tert-butyl ester To 6.16 g (18.6 mmol) of 3-hydroxy-2-(4-methoxybenzenesulfonylamino)-propionic acid tert-butyl ester in 50 ml of N,N-dimethylformamide, cooled in an ice bath, was added 0.781 g (19.5 mmol) of sodium hydride. After gas evolution ceased, a solution of 4.02 g (18.6 mmol) of 2-nitrobenzylbromide in 18 ml of N,N-dimethylformamide was added dropwise. The mixture was stirred under nitrogen at room temperature for 4 hours and 1.0 g of 2-nitrobenzyl bromide was added. The mixture was stirred at room temperature overnight and the solvent removed under vacuum. The residue was diluted with water and extracted with $CH_2Cl_2$. The organic extract was washed with $H_2O$, brine and dried with $Na_2SO_4$. The solvent was removed to give 11.2 g of solid which was chromatographed on silica gel with hexane-ethyl acetate (1:1) as eluent followed by hexane-ethyl acetate (35:65) as eluent. The fractions containing product were combined and the solvent was then removed to gave 7.7 g (89%) of solid. A sample from a 3 mmol run gave a gum. Anal. for $C_{21}H_{26}N_2O_8S$: Calc'd: C,54.1; H,5.6; N,6.0; Found: C,54.0; H,5.7; N,6.0.

REFERENCE EXAMPLE 5

2-[(2-Aminobenzyl)-(4-methoxybenzenesulfonyl)amino]-3-hydroxypropionic acid, tert-butyl ester A mixture of 0.60 g (1.28 mmol) of 3-hydroxy-2-[(4-methoxybenzenesulfonyl)-(2-nitrobenzyl)amino]propionic acid, tert-butyl ester and 1.45 g (6.45 mmol) of $SnCl_2.2H_2O$ in 20 ml of methanol was heated in an oil bath at 90° C. for 2 hours. The solvent was removed under vacuum and ethyl acetate added to the residue. The mixture was neutralized with saturated sodium bicarbonate solution and filtered through diatomaceous earth. The ethyl acetate layer was separated and washed with $H_2O$, brine and dried with $Na_2SO_4$. The solvent was removed under vacuum to give 0.30 g (53%) of a gum. Anal. for $C_{21}H_{28}N_2O_6S$: Calc'd: C, 57.8; H,6.5; N,6.4; Found: C, 57.8; H,7.0; N,6.2.

REFERENCE EXAMPLE 6

2-[(2-Aminobenzyl)-(4-methoxybenzenesulfonyl)amino]-3-hydroxypropionic acid

A solution of 0.75 g (1.72 mmol) of 2-[(2-aminobenzyl)-(4-methoxybenzenesulfonyl)amino]-3-hydroxypropionic acid, tert-butyl ester and 6 ml of trifluoroacetic acid in 6 ml of $CH_2Cl_2$ was stirred at room temperature for 3 hours and then concentrated to dryness under vacuum. To the residue was added $H_2O$, $CH_2Cl_2$ and 1N NaOH until the aqueous layer reached pH 8. The aqueous layer was then separated, acidified with 2 N citric acid and extracted with ethyl acetate. The extract was washed with $H_2O$, brine and dried $Na_2SO_4$. The solvent was removed under vacuum to give 0.35 g (54%) of a solid. Anal. for $C_{17}H_{20}N_2O_6S$: Calc'd: C, 53.7; H,5.3; N,7.4; Found: C, 53.0; H,5.3; N,6.9.

REFERENCE EXAMPLE 7

2-{(2-[3-(Trifluoromethylbenzoyl)aminobenzyl]-(4-methoxybenzenesulfonyl)amino}acrylic acid, tert-butyl ester A mixture of 0.431 g (1 mmol) of 2-[(2-amino-benzyl)-(4-methoxybenzenesulfonyl)amino]-3-hydroxy-propionic acid, tert-butyl ester, 0.474 g (2.2 mmol) of 3-(trifluoromethyl)benzoyl chloride and 1 ml of pyridine in 2 ml of $CH_2Cl_2$ was stirred at room temperature for 3.5 hours. The mixture was poured into $H_2O$ and extracted with $CH_2Cl_2$. The extract was washed with $H_2O$, 2 N citric acid, $H_2O$, 1 N $NaHCO_3$, brine and dried with $Na_2SO_4$. The solvent was removed to give 0.72 g of solid. The solid was dissolved in 2 ml of tetrahydrofuran and 1.5 ml of triethylamine was added thereto. The solution was heated at 65° C. overnight and concentrated to dryness under vacuum. The residue was extracted with $CH_2Cl_2$ and the extract washed with $H_2O$ and dried with $Na_2SO_4$. The solvent was removed under vacuum to give 0.55 g of product as a solid. From a similar run the product was chromatographed on silica gel with hexane-ethyl acetate to give a solid, m.p. 65–72° C.

Anal. for $C_{29}H_{29}F_3N_2O_6S$: Calc'd: C, 59.0; H,5.0; N,4.7; Found: C, 59.2; H,5.2, N,4.4.

REFERENCE EXAMPLE 8

4-(4-Methoxybenzenesulfonyl)-1-(3-trifluoromethylbenzoyl)-2,3,4,5-tetrahydro-1H-[1,4]benzodiazepine-3-carboxylic acid, tert-butyl ester A mixture of 0.55 g (0.932 mmol) of 2-{(2-[3-(trifluoromethyl)benzoyl]-aminobenzoyl]-(4-methoxybenzenesulfonyl)amino}acrylic acid, tert-butyl ester and 0.102 g (1.21 mmol) of $NaHCO_3$ in 4 ml of methanol was stirred at room temperature overnight and the solvent removed. The residue was extracted with $CH_2Cl_2$ and the extract washed with $H_2O$, brine and dried with $Na_2SO_4$. The solvent was removed to give 0.57 g of solid. The solid was chromatographed on thick layer silica gel plates with hexane-ethyl acetate (1:1) as solvent to give 0.30 g of a light yellow solid, m.p. 57–60° C. Anal. for $C_{29}H_{29}F_3N_2O_6S$: Calc'd: C,59.0; H,5.0; N,4.7; Found: C,58.8; N,5.0; N,4.6.

REFERENCE EXAMPLE 9

4-(4-Methoxybenzenesulfonyl)-1-(3-trifluoromethylbenzoyl)-2,3,4,5-tetrahydro-1H-[1,4]benzodiazepine-3-carboxylic acid A mixture of 0.36 g (0.61 mmol) of 4-(4-methoxybenzenesulfonyl)-1-(3-trifluoromethylbenzoyl)-2,3,4,5-tetrahydro-1H-[1,4]benzodiazepine-3-carboxylic acid, tert-butyl ester and 3 ml of trifluoroacetic acid in 3 ml of $CH_2Cl_2$ was stirred at room temperature for 3 hours. The mixture was concentrated to dryness under vacuum and the residue extracted with $CH_2Cl_2$. The $CH_2Cl_2$ was washed with 1 N $NaHCO_3$ and the aqueous layer (pH 8) was acidified with 2 N citric acid and extracted with ethyl acetate. The extract was dried ($Na_2SO_4$). The original $CH_2Cl_2$ extract was washed with 2 N citric acid, $H_2O$, brine and dried with $Na_2SO_4$. The $CH_2Cl_2$ extract and the ethyl acetate extract were combined and the solvent removed under vacuum to give 0.31 g of solid, m.p. 105–110° C. Anal. for $C_{25}H_{21}F_3N_2O_6S$: Calc'd: C,56.2; H,4.0; N,5.2; Found: C,55.1; H,3.7; N,5.0.

REFERENCE EXAMPLE 10

Methyl 1-([1,1'-Biphenyl]-2-carbonyl)-4-(4-methoxybenzenesulfonyl)-2,3,4,5-tetrahydro-1H-[1,4]benzodiazepine-3-carboxylate To a mixture of 1.5 g (3.8 mmol) of methyl 2-[(2-aminobenzyl)-(4-methoxybenzenesulfonyl)amino]-3-hydroxypropionate and 2.65 ml of triethylamine in 12 ml of $CH_2Cl_2$ chilled at 0° C. was added a solution of [1,1'-biphenyl]-2-carbonyl chloride in 6 ml of $CH_2Cl_2$. The mixture was stirred at room temperature overnight and diluted with $CH_2Cl_2$ and $H_2O$. The organic layer was separated and washed with 2 N citric acid, brine and dried-with $Na_2SO_4$. The solvent was removed under vacuum to give 2.2 g of a white foam. Anal. for $C_{31}H_{28}N_2O_6S$: Calc'd: C,66.9; H,5.1; N,5.0; Found: C,67.3; H,5.2; N,4.7.

REFERENCE EXAMPLE 11

Methyl 4-(4-Methoxybenzenesulfonyl)-1-(2-methyl-5-fluorobenzoyl)-2,3,4,5-tetrahydro-1H-[1,4]benzodiazepine-3-carboxylate To a mixture of 1.5 g (3.80 mmol) of methyl 2-[(2-aminobenzyl)-(4-methoxybenzenesulfonyl)amino]-3-hydroxypropionate and 2.64 ml (18.97 mmol) of triethylamine in 15 ml of $CH_2Cl_2$, chilled to 0° C., was added 1.36 g (11.4 mmol) of 2-methyl-5-fluorobenzoyl chloride. The mixture was stirred at room temperature overnight. The solution was then diluted with $CH_2Cl_2$ and water and the organic layer separated. The organic layer was washed with 2 N citric acid, brine and dried with $Na_2SO_4$. The solvent was removed under vacuum to give 2.2 g of a white foam. Anal. for $C_{26}H_{25}FN_2O_6S$: Calc'd: C,60.9; H,4.9; N,5.5; Found: C,60.9; H,5.0; N,5.0; Mass spectrum (ES) 513.4 (M+H).

REFERENCE EXAMPLE 12

Methyl 4-(4-Methoxybenzenesulfonyl)-2,3,4,5-tetrahydro-1H-[1,4]benzodiazepine-3-carboxylate To a mixture of 5.0 g (12.68 mmol) of methyl 2-[(2-aminobenzyl)-(4-methoxybenzenesulfonyl)amino]-3-hydroxypropionate and 17.7 ml (26.8 mmol) of triethylamine in 50 ml of $CH_2Cl_2$ chilled to 0° C. was added 9.05 ml (63.4 mmol) of benzyl chloroformate. The mixture was stirred overnight and then cooled to 0° C. and 0.8 ml of triethylamine and 9.05 ml (63.4 mmol) of benzyl chloroformate were added thereto. The mixture was stirred overnight and then washed with $H_2O$, 2 N citric acid, brine and dried with $Na_2SO_4$. The solvent was removed under vacuum to give 6.95 g of solid. The solid was chromatographed on silica gel with hexane-ethyl acetate (1:1) to give 2.7 g of product as a viscous yellow oil. From a similar 0.5 g run, there was obtained 0.178 g of an oil. Anal. for $C_{18}H_{20}N_2O_5S$: Calc'd: C,57.4; H,5.4; N,7.4; S,8.5; Found: C,57.9; H,5.4; N,6.7; S,7.9; Mass spectrum (ES) 377.2 (M+H).

REFERENCE EXAMPLE 13

Methyl 3-Hydroxy-2-(4-methoxybenzenesulfonylamino)propionate

To a mixture of 5.0 g (32.14 mmol) of D,L-serine, methyl ester and 15.7 ml (0.012 mol) of triethylamine in 100 ml of $CH_2Cl_2$, cooled to 0° C., was added portionwise 6.64 g (32.14 mmol) of 4-methoxybenzenesulfonyl chloride. The mixture was then stirred under argon at room temperature for 2 days. The mixture was diluted with 100 ml of $CH_2Cl_2$ and then washed with 60 ml each of $H_2O$, 2 N citric acid, brine and dried with $Na_2SO_4$. The solvent was removed under vacuum to give a solid. Crystallization from ethyl acetate gave 5.0 g (54%) of white crystals, m.p. 92–94° C. Anal. for $C_{11}H_{15}NO_6S$: Calc'd: C,45.7; H,5.2; N,4.8; S,11.1; Found: C,45.6; H,5.2; N,4.8; S,1.11.

REFERENCE EXAMPLE 14

Methyl 3-Hydroxy-2-[(4-methoxybenzenesulfonyl)-(2-nitrobenzyl) amino]propionate To a solution of 15.0 g (51.85 mmol) of methyl 3-hydroxy-2-(4-methoxybenzenesulfonylamino)propionate in 125 ml of N,N-dimethylformamide, cooled in an ice bath, was added portionwise 2.29 g (57.03 mmol) of NaH (60% in oil). The mixture was stirred at 0° C. for 20 minutes and then a solution of 12.32 g (57.03 mmol) of 2-nitrobenzyl bromide in 25 ml of dry N,N-dimethylformamide was added dropwise. The solution was stirred at room temperature for 48 hours and diluted with 500 ml of ethyl acetate and water. The organic layer was separated and the aqueous layer extracted with 250 ml of ethyl acetate. The combined organic layer and extract was washed with 200 ml each of $H_2O$, 1 N $NaHCO_3$, brine and dried with $Na_2SO_4$. The solvent was removed and the residual solid was triturated with ethyl acetate, cooled and filtered to give 13.5 g (61%) of white crystals, having a m.p. 127–129° C. From a small scale run (3.0 g) there was obtained 2.32 g of white crystals, having a m.p. 127–129° C. Anal. for $C_{18}H_{20}N_2O_8S$: Calc'd: C.50.9; H,4.8; N,6.6; Found: C,50.9; H,4.8; N,6.5.

REFERENCE EXAMPLE 15

Methyl 2-[(2-Aminobenzyl)-(4-methoxybenzenesulfonyl)amino]-3-hydroxypropionate To a mixture under nitrogen of 1.5 g (3.53 mmol) of methyl 3-hydroxy-2-[(4-methoxybenzenesulfonyl)-(2-nitrobenzyl)amino]propionate in 5 ml of dry ethanol was added 1.12 g (17.69 mmol) of ammonium formate followed by the addition of 0.50 g of 10% palladium on carbon. The mixture was stirred overnight at room temperature and heated at 80° C. for 2 hours. The mixture was filtered through diatomaceous earth and the filtrate concentrated to dryness under vacuum to give a semisolid. Trituration with ethyl acetate gave 0.65 g (47%) of white crystals, m.p. 138–140° C.; Anal. for $C_{18}H_{22}N_2O_6S$: Calc'd: C,54.8; H,5.6; N,7.1; Found: C,53.0; H,5.6; N,6.8.

REFERENCE EXAMPLE 16

Methyl 3-Hydroxy-2-{(4-methoxybenzenesulfonyl)-[2-(2,2,2-trifluoroacetylamino)benzyl]amino}propionate To a solution of 0.50 g (1.27 mmol) of methyl 2-[(2-aminobenzyl)-(4-methoxybenzenesulfonyl)amino]-3-hydroxypropionate in 5 ml of $CH_2Cl_2$ was added 1.8 ml (12.7 mmol) of trifluoroacetic anhydride. The solution was stirred for 1 hour and concentrated to dryness under vacuum. Methanol was added to the residue and the solvent was removed under vacuum. The addition of methanol and concentration to dryness was repeated twice. The residue was chromatographed on silica gel thick layer plates with hexane-ethyl acetate (1:1) to give 0.50 g of a colorless glass. Anal. for $C_{20}H_{21}F_3N_2O_7S$: Calc'd: C,49.0; H,4.3; N,5.7; Found: C.49.0; H,4.5; N,5.4.

REFERENCE EXAMPLE 17

Methyl 2-[(4-Methoxybenzenesulfonyl)-(2-nitrobenzyl)amino]acrylate

To a solution of 1.0 g (2.356 mmol) of methyl 3-hydroxy-2-[(4-methoxybenzenesulfonyl)-(2-nitrobenzyl)amino]propionate in 2 ml of pyridine, cooled to –10° C. was added 0.539 g (2.83 mmol) of 4-methylbenzeuesulfonyl chloride. The solution was chilled overnight and 4 ml of pyridine and 0.539 g (2.83 mmol) of 4-methylbenzene-sulfonyl chloride were added. The mixture was stirred and chilled at –10° C. for 24 hours and diluted with $H_2O$. The mixture was extracted with ethyl acetate and the extract washed with $H_2O$, 2 N citric acid, and brine and then dried ($Na_2SO_4$). The solvent was removed under vacuum to give 1.2 g of an oil. The oil was dissolved in 6 ml of pyridine and 1.08 g of 4-methylbenzenesulfonyl chloride was added thereto. The mixture was stirred at room temperature overnight and diluted with $H_2O$. The mixture was extracted with ethyl acetate and the extract was washed with $H_2O$, 2 N citric acid, and brine and then dried with $Na_2SO_4$. The solvent was removed to give 1.0 g of brown oil. The oil was crystallized from ethanol to give white crystals, m.p. 65–67° C. Anal. for $C_{18}H_{18}N_2O_7S$: Calc'd: C,53.2; H,4.5; N,6.9; Found: C,53.7; H,4.5; N,7.2.

REFERENCE EXAMPLE 18

Methyl 2-{(4-Methoxybenzenesulfonyl)-[2-(4-pyridinylcarbonyl) aminobenzyl]amino}acrylate To a mixture of 1.5 g (3.80 mmol) of methyl 2-[(2-aminobenzyl)-(4-methoxybenzenesulfonyl)amino]-3-hydroxypropionate and 3.0 ml (21.6 mmol) of triethylamine in 15 ml of $CH_2Cl_2$ cooled to 0° C. was added 1.7 g (9.5 mmol) ml of 4-pyridinecarbonyl chloride (isonicotinoyl chloride). The mixture was stirred at room temperature overnight and diluted with $CH_2Cl_2$. The mixture was washed with $H_2O$, 2 N citric acid, and brine and then dried with $Na_2SO_4$. The solvent was removed to give 1.8 g of a light tan solid; Anal. for $C_{24}H_{23}N_3O_6S$: Calc'd: C,59.9; H,4.8; N,8.7; S,6.6; Found: C,59.0; H,4.8; N,8.5; S,6.9; Mass spectrum (ES) 482.6(M+H).

Utilizing the procedure described in Reference Example 18. the following intermediate compounds can be prepared from the appropriately unsubstituted methyl 2-[(2-aminobenzyl)-(4-methoxybenzenesulfonyl)amino]-3-hydroxypropionate or the appropriately substituted methyl 2-[(substituted-2-aminobenzyl)-(4-methoxybenzenesulfonyl)amino]-3-hydroxypropionate.

REFERENCE EXAMPLE 19

Methyl 2-{(4-Methoxybenzenesulfonyl)-[2-(2,2,2-trifluoroacetylamino)benzyl]amino}acrylate white crystals, m.p. 120–121° C. Anal. for $C_{20}H_{19}F_3N_2O_6S$: Calc'd: C.50.9; H,4.1; N,5.9; Found: C,50.8; H,4.2; N,5.6.

REFERENCE EXAMPLE 20

Methyl 2-[(2-Benzoylaminobenzyl)-(4-methoxybenzenesulfonyl) amino]acrylate yellow oil. Anal. for $C_{25}H_{24}N_2O_6S$: Calc'd: C,62.5; H,5.0; N,5.8; Found: C,62.7; H,5.3; N,5.0.

REFERENCE EXAMPLE 21

Methyl 2-[(2-Acetylaminobenzyl)-(4-methoxybenzenesulfonyl) amino]acrylate

REFERENCE EXAMPLE 22

Methyl 2-((4-Methoxybenzenesulfonyl)-{2-[(3-pyridinylcarbonyl)amino]benzyl}amino)acrylate off-white solid. Anal. for $C_{24}H_{23}N_3O_6S$: Calc'd: C,59.9; H,4.8; N,8.7; S,6.6; Found: C,58.9; H,4.8; N,8.4; S,6.4; Mass spectrum (ES) 482.8(M+H).

EXAMPLE 23

Methyl 2-((4-Methoxybenzenesulfonyl)-{[(2-thienylcarbonyl)amino]benzyl}amino)acrylate tan solid. Anal. for $C_{23}H_{22}N_2O_6S_2$: Calc'd: C.56.8; H,4.6; N,5.8; Found: C,55.7; H,4.4; N,4.9.

REFERENCE EXAMPLE 24

Methyl 2-{[2-(-Methoxyacetylamino)benzyl]-(4-methoxybenzenesulfonyl)amino}acrylate yellow oil. Anal. for $C_{21}H_{24}N_2O_7S$: Calc'd: C,56.2; H,5.4; N,6.3; Found: C,55.3; H,5.6; N,5.8.

REFERENCE EXAMPLE 25

Methyl 2-{(4-Methoxybenzenesulfonyl)-[2-(n-propylsulfonylamino)benzyl]amino}acrylate light brown oil. Anal. for $C_{21}H_{26}N_2O_7S_2$: Calc'd: C,52.3; H,5.4; N,5.8; Found: C,51.9; H,5.4; N,5.7.

REFERENCE EXAMPLE 26

Methyl 2-{[2-(3-Phenylpropionyl)aminobenzyl]-(4-methoxybenzenesulfonyl)amino}acrylate light brown oil. Anal. for $C_{27}H_{28}N_2O_6S$: Calc'd: C,63.8; H,5.6; N,5.5; Found: C,66.7; H,5.8; N,4.1.

REFERENCE EXAMPLE 27 tert-Butyl 2-{[2-(3-Trifluoromethylbenzoyl)aminobenzyl]-(4-methoxybenzenesulfonyl)amino}acrylate yellow solid; m.p. 65–72° C.

REFERENCE EXAMPLE 28

Methyl 2-{[2-(4-Biphenylcarbonyl)aminobenzyl]-(4-methoxybenzenesulfonyl)amino}acrylate white solid. Anal for $C_{31}H_{28}N_2O_6S$: Calc'd: C,66.9; H,5.1; N,5.0; Found: C,66.1; H,5.0; N,5.1.

REFERENCE EXAMPLE 29

Methyl 2-{[2-(Cyclopropylcarbonyl)aminobenzyl]-(4-methoxybenzenesulfonyl)amino}acrylate yellow oil. Anal. for $C_{22}H_{24}N_2O_6S$: Calc'd: C,59.5; H,5.4; N,6.3; Found: C,60.0; H,5.7; N,6.0; Mass spectrum (ES) 445.5 (M+H).

REFERENCE EXAMPLE 30

Methyl 2-{[2-(Cyclohexylcarbonyl)aminobenzyl]-(4-methoxybenzenesulfonyl)amino}acrylate white foam. Anal. for $C_{25}H_{30}N_2O_6S$: Calc'd: C,61.7; H,6.2; N,5.8; Found: C,59.1; H,6.0; N,5.4; Mass spectrum (ES) 487.5 (M+H).

REFERENCE EXAMPLE 31

Methyl 2-{[2-(3-Fluorobenzoyl)aminobenzyl]-(4-methoxybenzenesulfonyl)amino}acrylate

REFERENCE EXAMPLE 32

Methyl 2-{[2-(3-Chlorobenzoyl)aminobenzyl]-(4-methoxybenzenesulfonyl)amino}acrylate

REFERENCE EXAMPLE 33

Methyl 2-{[2-(2,4-Dichlorobenzoyl)aminobenzyl]-(4-methoxybenzenesulfonyl)amino}acrylate

REFERENCE EXAMPLE 34

Methyl 2-{[2-(2,3-Difluorobenzoyl)aminobenzyl]-(4-methoxybenzenesulfonyl)amino}acrylate

REFERENCE EXAMPLE 35

Methyl 2-{[2-(2-Chloro-4-fluorobenzoyl)aminobenzyl]-(4-methoxybenzenesulfonyl)amino}acrylate

REFERENCE EXAMPLE 36

Methyl 2-{[2-(2-Furanylcarbonyl)aminobenzyl]-(4-methoxybenzenesulfonyl)amino}acrylate off-white solid. Anal. for $C_{23}H_{22}N_2O_7S$. Calc'd: C,58.7; H,4.7; N,6.0; Found: Ca58.0; H,4.1; N,3.8; Mass Spectrum (ES) 470.9 (M+H).

REFERENCE EXAMPLE 37

Methyl 2-((4-Methoxybenzenesulfonyl)-{2-[(3-thienylcarbonyl)amino]benzyl}amino)acrylate

REFERENCE EXAMPLE 38

Methyl 2-{[2-(2-Acetylaminoacetyl)aminobenzyl]-(4-methoxybenzenesulfonyl)amino}acrylate

REFERENCE EXAMPLE 39

Methyl 2-{[2-(2-Dimethylacetyl)aminobenzyl]-(4-methoxybenzenesulfonyl)amino}acrylate

REFERENCE EXAMPLE 40

Methyl 2-{[2-(Cyclobutylcarbonyl)aminobenzyl]-(4-methoxybenzenesulfonyl)amino}acrylate

REFERENCE EXAMPLE 41

Methyl 1-Methoxyacetyl-4-(4-methoxybenzenesulfonyl)-2,3,4,5-tetrahydro-1H-[1,4]benzodiazepine-3-carboxylate To a mixture of 0.449 g (1 mmol) of methyl 2-[[2-(2-methoxyacetamido)benzyl]-(4-methoxybenzene-sulfonyl)amino]acrylate in 5 ml of anhydrous methanol was added 0.109 g (1.3 mmol) of anhydrous sodium bicarbonate. The mixture was stirred at room temperature overnight and the solvent removed under vacuum. To the residue was added ethyl acetate and water. The organic layer was separated and washed with $H_2O$ and brine and then dried with $Na_2SO_4$. The solvent was removed to give 0.41 g of solid. The solid was crystallized from ethyl acetate to give 0.28 g of white crystals, m.p. 160–163° C. Anal. for $C_{21}H_{24}N_2O_7S$: Calc'd: C,56.2; H,5.4; N,6.3; Found: C,56.1; H,5.3; N,6.3; S,6.9; Mass spectrum (ES) 449.1 (M+H).

Utilizing the procedure in Reference Example 41, the following intermediate compounds can be prepared from the appropriate methyl 2-{(4-methoxybenzenesulfonyl)-[2-(substituted amino)benzyl]amino}acrylates.

REFERENCE EXAMPLE 42

Methyl 4-(4-Methoxybenzenesulfonyl)-1-(4-methylphenylsulfonyl)-2,3,4,5-tetrahydro-1H-[1,4]benzodiazepine-3-carboxylate white foam. Anal. for $C_{25}H_{26}N_2O_7S_2$: Calc'd: C,56.6; H,4.9; N,5.3 Found: C,56.2; H,5.2; N,5.2.

REFERENCE EXAMPLE 43

Methyl 1,4-Bis-(4-methoxybenzenesulfonyl)-2,3,4,5-tetrahydro-1H-[1,4]benzodiazepine-3-carboxylate white solid. Anal. for $C_{25}H_{26}N_2O_8S_2$: Calc'd: C,54.9; H,4.8; N,5.1; Found: C,54.8; H,4.9; N,5.1.

REFERENCE EXAMPLE 44

Methyl 1-Methanesulfonyl-4-(4-methoxybenzeuesulfonyl)-2,3,4,5-tetrahydro-1H-[1,4]benzodiazepine-3-carboxylate white crystals, m.p. 136–137° C. Anal. for $C_{19}H_{22}N_2O_7S_2$: Calc'd: C,50.2; H,4.9; N,6.2; Found: C,50.1; H,4.9; N,6.4.

REFERENCE EXAMPLE 45

Methyl 1-Benzoyl-4-(4-methoxybenzenesulfonyl)-2,3,4,5-tetrahydro-1H-[1,4]benzodiazepine-3-carboxylate tan solid. Anal. for $C_{25}H_{24}N_2O_2S$: Calc'd: C,62.2; H,5.4; N,5.8; Found: C,62.3; H,5.2; N,5.6.

REFERENCE EXAMPLE 46

Methyl 1-Acetyl-4-(4-methoxybenzenesulfonyl)-2,3,4,5-tetrahydro-1H-[1,4]benzodiazepine-3-carboxylate white crystals, m.p. 150–155° C. Anal. for $C_{20}H_{22}N_2O_6S$: Calc'd: C,57.4; H,5.3; N,6.7; Found: C,56.6; H, 5.2; N,6.5.

REFERENCE EXAMPLE 47

Methyl 4-(4-Methoxybenzenesulfonyl)-1-(3-pyridinylcarbonyl)-2,3,4,5-tetrahydro-1H-[1,4]benzodiazepine-3-carboxylate off-white solid; Anal. for $C_{24}H_{23}N_3O_6S$: Calc'd: C,59.9; H,4.8; N,8.7; Found: C,59.2; H,4.8; N,8.3; Mass spectrum (ES) 482.2 (M+H).

REFERENCE EXAMPLE 48

Methyl 4-(4-Methoxybenzenesulfonyl)-1-(2-thienylcarbonyl)-2,3,4,5-tetrahydro-1H-[1,4]benzodiazepine-3-carboxylate off-white solid. Anal. for $C_{23}H_{22}N_2O_6S_2$: Calc'd: C,56.8; H,4.6; N,5.8; Found: C,56.0; H,4.6; N,5.2.

REFERENCE EXAMPLE 49

Methyl 4-(4-Methoxybenzenesulfonyl)-1-(4-pyridinylcarbonyl)-2,3,4,5-tetrahydro-1H-[1,4]benzodiazepine-3-carboxylate off-white crystals, m.p. 162–164° C. Anal. for $C_{24}H_{23}N_3O_6S$: Calc'd: C.59.9; H,4.8; N,8.7; Found: C,59.9; H,4.8; N,8.7.

REFERENCE EXAMPLE 50

Methyl 1-(4-Biphenylcarbonyl)-4-(4-methoxybenzenesulfonyl)-2,3,4,5-tetrahydro-1H-[1,4]benzodiazepine-3-carboxylate white solid; Anal. for $C_{31}H_{28}N_2O_6S$: Calcd: C,66.9; H,5.1; N,5.0; Found: C,65.8; H,5.2; N,5.0; Mass spectrum (ES) 557.6 (M+H).

REFERENCE EXAMPLE 51

Methyl 4-(4-Methoxybenzenesulfonyl)-1-(propane-1-sulfonyl)-2,3,4,5-tetrahydro-1H-[1,4]benzodiazepine-3-carboxylate yellow oil. Anal. for $C_{21}H_{26}N_2O_7S_2$: Calc'd: C,52.3; H,5.4; N,5.8; Found: C.51.8; H,5.4; N,5.6.

REFERENCE EXAMPLE 52

Methyl 1-([1,1'-Biphenyl]-2-carbonyl)-4-(4-methoxybenzenesulfonyl)-2,3,4,5-tetrahydro-1H-[1,4]benzodiazepine-3-carboxylate white foam. Anal. for $C_{31}H_{28}N_2O_6S$: Calc'd: C,66.9; H,5.1; N,5.0; Found: C,67.3; H,5.2; N,4.7; Mass spectrum (ES) 557.6 (M+H).

REFERENCE EXAMPLE 53

Methyl 1-(3-Fluorobenzoyl)-4-(4-methoxybenzenesulfonyl)-2,3,4,5-tetrahydro-1H-[1,4]benzodiazepine-3-carboxylate

REFERENCE EXAMPLE 54

Methyl 4-(4-Methoxybenzenesulfonyl)-1-(2-methyl-5-fluorobenzoyl)-2,3,4,5-tetrahydro-1H-[1,4]benzodiazepine-3-carboxylate white solid; Anal. for $C_{26}H_{25}FN_2O_6S$: Calc'd: C,60.9; H,4.9; N,5.5; Found: C,60.9; H,5.0; N,5.0.

REFERENCE EXAMPLE 55

Methyl 4-(4-Methoxybenzenesulfonyl)-1-(2-methyl-3-fluorobenzoyl)-2,3,4,5-tetrahydro-1H-[1,4]benzodiazepine-3-carboxylate

REFERENCE EXAMPLE 56

Methyl 4-(4-Methoxybenzenesulfonyl)-1-(3-phenylpropionyl)-2,3,4,5-tetrahydro-1H-[1,4]benzodiazepine-3-carboxylate white solid; Anal. for $C_{27}H_{28}N_2O_6S$: Calc'd: C,63.8; H,5.6; N,5.5; Found: C,64.0; H,5.7; N,5.3; S,6.5.

REFERENCE EXAMPLE 57

Methyl 4-(4-Methoxybenzenesulfonyl)-1-(2-trifluoromethylbenzoyl)-2,3,4,5-tetrahydro-1H-[1,4]benzodiazepine-3-carboxylate

REFERENCE EXAMPLE 58

Methyl 1-(2-Chloro-6-trifluoromethylbenzoyl)-4(4-methoxybenzenesulfonyl)-2,3,4,5-tetrahydro-1H-[1,4]benzodiazepine-3-carboxylate

REFERENCE EXAMPLE 59

Methyl 1-(4-Fluoro-2-trifluoromethylbenzoyl)-4-(4-methoxybenzenesulfonyl)-2,3,4,5-tetrahydro-1H-[1,4]benzodiazepine-3-carboxylate

REFERENCE EXAMPLE 60

Methyl 1-(2-Fluoro-6-trifluoromethylbenzoyl)-4-(4-methoxybenzenesulfonyl)-2,3,4,5-tetrahydro-1H-[1,4]benzodiazepine-3-carboxylate

REFERENCE EXAMPLE 61

Methyl 4-(4-Methoxybenzenesulfonyl)-1-(2-methylbenzoyl)-2,3,4,5-tetrahydro-1H-[1,4]benzodiazepine-3-carboxylate

REFERENCE EXAMPLE 62

Methyl 4-(4-Methoxybenzenesulfonyl)-1-(2-methyl-6-chlorobenzoyl)-2,3,4,5-tetrahydro-1H-[1,4]benzodiazepine-3-carboxylate

REFERENCE EXAMPLE 63

Methyl 1-(2,4-Dimethylbenzoyl)-4-(4-methoxybenzenesulfonyl)-2,3,4,5-tetrahydro-1H-[1,4]benzodiazepine-3-carboxylate

REFERENCE EXAMPLE 64

Methyl 1-(2,5-Dimethylbenzoyl)-4-(4-methoxybenzenesulfonyl)-2,3,4,5-tetrahydro-1H-[1,4]benzodiazepine-3-carboxylate

REFERENCE EXAMPLE 65

Methyl 1-(2-Chloro-4-fluorobenzoyl)-4-(4-methoxybenzenesulfonyl)-2,3,4,5-tetrahydro-1H-[1,4]benzodiazepine-3-carboxylate

REFERENCE EXAMPLE 66

Methyl 1-(2-Chlorobenzoyl)-4-(4-methoxybenzenesulfonyl)-2,3,4,5-tetrahydro-1H-[1,4]benzodiazepine-3-carboxylate

REFERENCE EXAMPLE 67

Methyl 1-(2-Fluorobenzoyl)-4-(4-methoxybenzenesulfonyl)-2,3,4,5-tetrahydro-1H-[1,4]benzodiazepine-3-carboxylate

REFERENCE EXAMPLE 68

Methyl 1-(2-Chloro-6-fluorobenzoyl)-4-(4-methoxybenzenesulfonyl)-2,3,4,5-tetrahydro-1H-[1,4]benzodiazepine-3-carboxylate

REFERENCE EXAMPLE 69

Methyl 1-(2,3-Difluorobenzoyl)-4-(4-methoxybenzenesulfonyl)-2,3,4,5-tetrahydro-1H-[1,4]benzodiazepine-3-carboxylate

REFERENCE EXAMPLE 70

Methyl 1-(2,4-Dichlorobenzoyl)-4-(4-methoxybenzenesulfonyl)-2,3,4,5-tetrahydro-1H-[1,4]benzodiazepine-3-carboxylate Prepared according to the procedure set forth in Reference Example 10; white solid. Anal. for $C_{25}H_{22}Cl_2N_2O_6S$: Calc'd: C,54.7; H,4.0; N,5.1; Found: C,54.4; H,3.8; N,4.9; Mass spectrum (548.9) (M+H); 550.9 (M+H).

REFERENCE EXAMPLE 71

Methyl 1-(2,3-Dichlorobenzoyl)-4-(4-methoxybenzenesulfonyl)-2,3,4,5-tetrahydro-1H-[1,4]benzodiazepine-3-carboxylate

REFERENCE EXAMPLE 72

Methyl 1-(2,5-Dichlorobenzoyl)-4-(4-methoxybenzenesulfonyl)-2,3,4,5-tetrahydro-1H-[1,4]benzodiazepine-3-carboxylate

REFERENCE EXAMPLE 73

Methyl 1-(2-Methoxybenzoyl)-4-(4-methoxybenzenesulfonyl)-2,3,4,5-tetrahydro-1H-[1,4]benzodiazepine-3-carboxylate

REFERENCE EXAMPLE 74

Methyl 1-(4-Chloro-2-methoxybenzoyl)-4-(4-methoxybenzenesulfonyl)-2,3,4,5-tetrahydro-1H-[1,4]benzodiazepine-3-carboxylate

REFERENCE EXAMPLE 75

Methyl 4-(4-Methoxybenzenesulfonyl)-1-(2-methylthiobenzoyl)-2,3,4,5-tetrahydro-1H-[1,4]benzodiazepine-3-carboxylate

REFERENCE EXAMPLE 76

Methyl 4-(4-Methoxybenzenesulfonyl)-1-(3-methyl-2-thienylcarbonyl)-2,3,4,5-tetrahydro-1H-[1.4]benzodiazepine-3-carboxylate

REFERENCE EXAMPLE 77

Methyl 4-(4-Methoxybenzenesulfonyl)-1-(4-methyl-2-thienylcarbonyl)-2,3,4,5-tetrahydro-1H-[1,4]benzodiazepine-3-carboxylate

REFERENCE EXAMPLE 78

Methyl 1-(3-Chloro-2-thienylcarbonyl)-4-(4-methoxybenzenesulfonyl)-2,3,4,5-tetrahydro-1H-[1,4]benzodiazepine-3-carboxylate

REFERENCE EXAMPLE 79

Methyl 1-(2-Furanylcarbonyl)-4-(4-methoxybenzenesulfonyl)-2,3,4,5-tetrahydro-1H-[1,4]benzodiazepine-3-carboxylate off-white solid, m.p. 165–167° C. Anal. for $C_{23}H_{22}N_2O_7S$: Calc'd: C,58.7; H,4.7; N,6.0; Found: C,58.4; H,4.6; N,5.7; Mass spectrum (ES) 470.9 (M+H).

REFERENCE EXAMPLE 80

Methyl 4-(4-Methoxybenzenesulfonyl)-1-(3-methyl-2-furanylcarbonyl)-2,3,4,5-tetrahydro-1H-[1,4]benzodiazepine-3-carboxylate

REFERENCE EXAMPLE 81

Methyl 4-(4-Methoxybenzenesulfonyl)-1-(4-methyl-2-furanylcarbonyl)-2,3,4,5-tetrahydro-1H-[1,4]benzodiazepine-3-carboxylate

REFERENCE EXAMPLE 82

Methyl 1-(5-Chloro-2-furanylcarbonyl)-4-(4-methoxybenzenesulfonyl)-2,3,4,5-tetrahydro-1H-[1,4]benzodiazepine-3-carboxylate

REFERENCE EXAMPLE 83

Methyl 1-(5-Chloro-2-thienylcarbonyl)-4-(4-methoxybenzenesulfonyl)-2,3,4,5-tetrahydro-1H-[1,4]benzodiazepine-3-carboxylate

REFERENCE EXAMPLE 84

Methyl 1-Propionyl-4-(4-methoxybenzenesulfonyl)-2,3,4,5-tetrahydro-1H-[1,4]benzodiazepine-3-carboxylate

REFERENCE EXAMPLE 85

Methyl 1-Hexanoyl-4-(4-methoxybenzenesulfonyl)-2,3,4,5-tetrahydro-1H-[1,4]benzodiazepine-3-carboxylate

REFERENCE EXAMPLE 86

Methyl 1-(3-Methoxypropionyl)-4-(4-methoxybenzenesulfonyl)-2,3,4,5-tetrahydro-1H-[1,4]benzodiazepine-3-carboxylate

REFERENCE EXAMPLE 87

Methyl 4-(4-Methoxybenzenesulfonyl)-1-(3-thienylcarbonyl)-2,3,4,5-tetrahydro-1H-[1,4]benzodiazepine-3-carboxylate

REFERENCE EXAMPLE 88

Methyl 1-(3-Furanylcarbonyl)-4-(4-methoxybenzenesulfonyl)-2,3,4,5-tetrahydro-1H-[1,4]benzodiazepine-3-carboxylate

REFERENCE EXAMPLE 89

Methyl 1-(trans-Crotonyl)-4-(4-methoxybenzenesulfonyl)-2,3,4,5-tetrahydro-1H-[1,4]benzodiazepine-3-carboxylate

REFERENCE EXAMPLE 90

Methyl 1-(Methacryloyl)-4-(4-methoxybenzenesulfonyl)-2,3,4,5-tetrahydro-1H-[1,4]benzodiazepine-3-carboxylate

REFERENCE EXAMPLE 91

Methyl 1-(Chloroacetyl)-4-(4-methoxybenzenesulfonyl)-2,3,4,5-tetrahydro-1H-[1,4]benzodiazepine-3-carboxylate Following the method described for Reference Example 18. 3.0 g (7.61 mmol) of methyl 2-[2-aminobenzyl]-(4-methoxy-benzenesulfonyl)-amino]-3-hydroxypropionate was reacted with 1.82 ml (22.8 mmol) of chloroacetylchloride to give 4.0 g of solid. Chromatography on silica gel with ethyl acetate-hexane (1:1) as a solvent gave 1.5 g of methyl 2-[(2-chloroacetylaminobenzyl)-(4-methoxybenzenesulfonyl)-amino]acrylate. A 1.3 g sample of the preceding compound was reacted with 0.312 g of anhydrous $NaHCO_3$ in 10 ml of anhydrous methanol at room temperature overnight and the mixture was then heated at 80° C. for 5 hours. The solvent was removed and the residue partitioned between $H_2O$ and ethyl acetate. The ethyl acetate extract was washed with brine, dried with $Na_2SO_4$ and the solvent removed. The residue was triturated with hexane-ethyl acetate, chilled and filtered to give the product; Mass spectrum (ES) 453.1 (M+H).

REFERENCE EXAMPLE 92

Methyl 1-(Acetylaminoacetyl)-4-(4-methoxybenzenesulfonyl)-2,3,4,5-tetrahydro-1H-[1,4]benzodiazepine-3-carboxylate

REFERENCE EXAMPLE 93

Methyl 1-(N,N-Dimethylaminoacetyl)-4-(4-methoxybenzenesulfonyl)-2,3,4,5-tetrahydro-1H-[1,4]benzodiazepine-3-carboxylate

REFERENCE EXAMPLE 94

Methyl 1-(Cyclopropylcarbonyl)-4-(4-methoxybenzenesulfonyl)-2,3,4,5-tetrahydro-1H-[1,4]benzodiazepine-3-carboxylate white crystals, m.p. 98–100° C. Anal. for $C_{22}H_{24}N_2O_6S$: Calc'd: C,59.5; H,5.4; N,6.3; Found: C,59.3; H,5 6; N,6.2; Mass spectrum (ES) 445.1 (M+H).

REFERENCE EXAMPLE 95

Methyl 1-(Cyclobutylcarbonyl)-4-(4-methoxybenzenesulfonyl)-2,3,4,5-tetrahydro-1H-[1,4]benzodiazepine-3-carboxylate

REFERENCE EXAMPLE 96

Methyl 4-(4-Methoxybenzenesulfonyl)-1-(trifluoroacetyl)-2,3,4,5-tetrahydro-1H-[1,4]benzodiazepine-3-carboxylate To a solution of 1.0 g (2.54 mmol) of methyl 3-hydroxy-2-{(4-methoxybenzenesulfonyl)-[2-(2,2,2-trifluoroacetylamino)benzyl]amino}propionate in 10 ml of $CH_2Cl_2$ was added 1.8 ml (12.7 mmol) of trifluoroacetic anhydride. After 1 hour at room temperature, the solvent was removed. Dichloromethane was added several times and the solvent removed under vacuum after each addition. Methanol was then added 2 times and the solvent removed under vacuum to give methyl 2-{(4-methoxybenzenesulfonyl)-[2-(2,2,2-trifluoroacetylamino)benzyl]-amino}acrylate as a glass. The glass was dissolved in methanol and 0.213 g of anhydrous $NaHCO_3$ was added. The mixture was stirred at room temperature overnight and concentrated under vacuum to dryness. To the residue was added ethyl acetate and water. The organic layer was separated, washed with $H_2O$, brine and dried with $Na_2SO_4$. The solvent was removed and the residue (1.0 g) was chromatographed on silica gel thick layer plates with hexane-ethyl acetate (1:1) as solvent to give 0.365 g of product as a glass. Anal. for $C_{20}H_{19}F_3N_2O_6S$:

Calc'd: C,50.9; H,4.1; N,5.9; F,12.1; S,6.7; Found: C,50.8; H,4.4; N,5.5; F,11.7; S,6.7; Mass spectrum (ES) 473.1 (M+H).

REFERENCE EXAMPLE 97

Methyl 4-(4-Methoxybenzenesulfonyl)-1-(4-methylphenylsulfonyl)-2,3,4,5-tetrahydro-1H-[1,4] benzodiazepine-3-carboxylate To 0.50 g (1.26 mmol) of 2-[(2-aminobenzyl)-(4-methoxybenzenesulfonyl)amino]-3-hydroxypropionate in 5 ml of pyridine cooled to 0° C. was added 0.284 g (2.59 mmol) of tosyl chloride. The mixture was stirred at 0° C. for 2 hours and then concentrated to remove the solvent. To the residue was added 8 ml of anhydrous ethanol and the mixture refluxed for 2 days. The mixture was concentrated to dryness and ethyl acetate added. The mixture was washed with $H_2O$, 2 N citric acid, brine and dried with $Na_2SO_4$. The filtrate was filtered through a thin pad of hydrous magnesium silicate and the filter pad washed with ethyl acetate. The filtrate was concentrated to dryness to give 0.60 g of a foam. Anal. for $C_{25}H_{26}N_2O_7S_2$: Calc'd: C,56.6; H,4.9; N,5.3; S,12.1; Found: C,56.2; H,5.2; N,5.2; S,11.4; Mass spectrum (ES) 531.6 (M+H).

REFERENCE EXAMPLE 98

Methyl 2-[(4-Methoxybenzenesulfonyl)-(2-methylsulfonylaminobenzyl)amino]acrylate To a solution of 1.0 g (2.54 mmol) of methyl [(2-aminobenzyl)-(4-methoxybenzenesulfonyl)amino]-3-hydroxypropionate in 10 ml of pyridine cooled to –5° C. was added 0.432 ml (5.58 mmol) of methanesulfonyl chloride. The mixture was stirred at 0° C. for 48 hours. To the mixture was added ice and $H_2O$ and the mixture was extracted with ethyl acetate. The extract was washed with $H_2O$, 2 N citric acid, brine and dried with $Na_2SO_4$. The solvent was removed under vacuum and the residue triturated with ethyl acetate-hexane to give 0.90 g of a solid, 128–142° C. Anal. for $C_{19}H_{22}N_2O_7S_2$: Calc'd: C,50.2; H,4.9; N,6.2; S,14.1; Found: C,49.6; H,5.0; N,6.9; S,14.0; Mass spectrum (ES) 455.5 (M+H).

REFERENCE EXAMPLE 99

Methyl 1,4-Bis-(4-Methoxybenzenesulfonyl)-2,3,4, 5-tetrahydro-1H-[1,4]benzodiazepine-3-carboxylate To a solution of 1.0 g (2.34 mmol) of methyl 2-[(2-aminobenzyl)-(4-methoxybenzenesulfonyl)amino]-3-hydroxypropionate in 6 ml of pyridine cooled to 0° C. to –5° C. was added 1.07 (5.18 mmol) of 4-methoxybenzenesulfonyl chloride. After 2 hours, the mixture was concentrated to dryness under vacuum. To the residue was added 12 ml of ethanol and the mixture refluxed overnight. The solvent was removed under vacuum and the residue chromatographed on silica gel thick layer plates with ethyl acetate-hexane (1:1) as solvent to give 0.83 g (60%) of product as a white foam; Anal. calc'd for $C_{25}H_{26}N_2O_8S_2$: C,54.9; H,4.8; N,5.1; S,11.7. Found: C,54.8; H,4.9; N,5.0; S, 11.5; Mass spectrum (ES) 547.1 (M+H); and a second component (0.38 g) methyl 2-{[2-(4-methoxybenzenesulfonyl)aminobenzyl]-(4-methoxybenzenesulfonyl)amino}-3-hydroxypropionate. Anal. for $C_{25}H_{28}N_2O_9S_2$: Calc'd: C,53.2; H,5.0; N,5.0; S,11.4; Found: C.51.8; H,5.1; N,4.7; S,11.3; Mass spectrum (ES) 565.2 (M+H).

REFERENCE EXAMPLE 100

Methyl 1-Acetyl-4-(4-methoxybenzenesulfonyl)-2,3, 4,5-tetrahydro-1H-[1,4]benzodiazepine-3-carboxylate To a solution of 0.70 g (1.52 mmol) of methyl 2-[(2-diacetylaminobenzyl)-(4-methoxybenzenesulfonyl)amino] acrylate in 5 ml of anhydrous methanol was added 0.332 g (3.95 mmol) of anhydrous sodium bicarbonate. The mixture was stirred at room temperature overnight and the solvent removed under vacuum. To the residue was added ethyl acetate and $H_2O$. The organic layer was separated, washed with brine and dried with $Na_2SO_4$. The solvent was removed and the residue dried under vacuum to give 0.59 g of white crystals, m.p. 150–155° C. Anal. for $C_{20}H_{22}N_2O_6S$: Calc'd: C,57.4; H,5.3; N,6.7; S,7.7; Found: C,56.6; H,5.2; N,6.5; S,7.5; Mass spectrum (ES) 419.9 (M+H).

REFERENCE EXAMPLE 101

Methyl 3-Acetoxy-2-[(2-diacetylaminobenzyl)-(4-methoxybenzenesulfonyl)amino]propionate A mixture of 1.0 g (2.54 mmol) of methyl 2-[(2-aminobenzyl)-(4-ethoxybenzenesulfonyl)amino]-3-hydroxypropionate and 1.3 ml of acetic anhydride in 8 ml of toluene was heated at 100° C. for 2 hours. The mixture was concentrated and 3 ml of acetic anhydride added thereto. The mixture was heated at 100° C. overnight and concentrated to dryness under high vacuum to give an oil. The oil was dried at 75° C. under vacuum for 48 hours to give 1.2 g of a yellow oil. Anal. for $C_{24}H_{28}N_2O_9S$: Calc'd: C,54.5; H,5.2; N,5.5; S,6.2; Found: C,54.6; H,5.1; N,5.4; S,6.4; Mass spectrum (ES) 520.8 (M+H).

REFERENCE EXAMPLE 102

Methyl 2-[(2-Diacetylaminobenzyl)-(4-methoxybenzenesulfonyl)amino]acrylate

A mixture of 1.0 g (1.97 mmol) of methyl 3-acetoxy-2-[(2-diacetylaminobenzyl)-(4-methoxybenzenesulfonyl) amino]propionate and 0.826 ml (5.92 mmol) of triethylamine in 5 ml of $CH_2Cl_2$ was stirred at room temperature overnight. The solution was diluted with 30 ml of $CH_2Cl_2$ and washed with 20 ml each of $H_2O$, 2 N citric acid, brine and dried with $Na_2SO_4$. The solvent was removed under vacuum to give a brown oil. Anal. for $C_{22}H_{24}N_2O_7S$: Calc'd: C,57.4; H,5.3; N,6.1; S,7.0; Found: C,56.2; H,5.5; N,5.6; S,7.2.

REFERENCE EXAMPLE 103

Methyl 2-{(4-Methoxybenzenesulfonyl)-[2-(2,2,2-trifluoroacetylamino)benzyl]amino}acrylate To a suspension of 1.0 g (2.54 mmol) of methyl 2-[(2-aminobenzyl)-(4-methoxybenzenesulfonyl)amino]-3-hydroxypropionate in 10 ml of toluene was added 1.8 ml (12.7 mmol) of trifluoroacetic anhydride (solid dissolves). The solution was stirred for 2 hours at room temperature and heated at 100° C. overnight. The mixture was then concentrated to dryness under vacuum. To the residue was added 0.9 ml of trifluoroacetic anhydride and the solution stirred at room temperature for 1.5 hours and concentrated to dryness. To the residue was added 10 ml of toluene and the mixture refluxed for 2 hours. The solution was cooled to room temperature and 2.5 ml of triethylamine added and the mixture stirred at room temperature overnight. The solution was concentrated to dryness and the residue dissolved in ethyl acetate. The ethyl acetate was washed with H$_2$O, brine and dried (Na$_2$SO$_4$). The solvent was removed under vacuum to give 1.0 g of colorless oil. Crystallization from ethyl acetate-hexane gave 0.625 g of colorless crystals, m.p. 120–121° C. Anal. for C$_{20}$H$_{19}$F$_3$N$_2$O$_6$S: Calc'd: C,50.9; H,4.1; N,5.9; S,6.7; F,12.1; Found: C,50.8; H,4.2; N,5.6; S,6.8; F,11.9; Mass spectrum (ES) 473.1 (M+H).

REFERENCE EXAMPLE 104

4-(4-Methoxybenzenesulfonyl)-1-(2-methyl-5-fluorobenzoyl)-2,3,4,5-tetrahydro-1H-[1,4]benzodiazepine-3-carboxylic Acid To a mixture of 1.9 g (3.71 mmol) of methyl 4-(4-methoxybenzenesulfonyl)-1-(2-methyl-5-fluorobenzoyl)-2,3,4,5-tetrahydro-1H-[1,4]benzodiazepine-3-carboxylate in 10 ml of tetrahydrofuran was added 5 ml (4.82 mmol) of 1 N NaOH. The mixture was stirred at room temperature for 1.5 hours and the solvent removed under vacuum. To the residue was added ethyl acetate and the mixture neutralized with 1 N HCl. The organic layer was separated, washed with brine and dried with Na$_2$SO$_4$. The solvent was removed under vacuum to give 1.41 g of white solid. Anal. for C$_{25}$H$_{23}$FN$_2$O$_6$S: Calc'd: C,60.2; H,4.7; N,5.6; Found: C,60.2; H,4.8; N,5.4 S,6.4; F,3.6; Mass spectrum (ES) 497.5 (M–H).

Utilizing the method described in Reference Example 104, the following benzodiazepine-3-carboxylic acids can be prepared.

REFERENCE EXAMPLE 105

4-(4-Methoxybenzenesulfonyl)-1-(4-methylphenylsulfonyl)-2,3,4,5-tetrahydro-1H-[1,4]benzodiazepine-3-carboxylic acid white foam. Anal. for C$_{24}$H$_{24}$N$_2$O$_7$S$_2$: Calc'd: C,55.8; H,4.7; N,5.4; Found: C,53.9; H,5.1; N,4.8; Mass spectrum (ES) 512.2 (M+H).

REFERENCE EXAMPLE 106

1,4-Bis-(4-methoxybenzenesulfonyl)-2,3,4,5-tetrahydro-1H-[1,4]benzodiazepine-3-carboxylic acid off-white solid. Anal. for C$_{24}$H$_{24}$N$_2$O$_8$S$_2$: Calc'd: C,54.1; H,4.5; N,5.3; Found: C,52.4; H,4.8; N,4.7; Mass spectrum (ES) 533.1 (M+H).

REFERENCE EXAMPLE 107

1-Methanesulfonyl-4-(4-methoxybenzenesulfonyl)-2,3,4,5-tetrahydro-1H-[1,4]benzodiazepine-3-carboxylic acid white solid. Anal. for C$_{18}$H$_{20}$N$_2$O$_7$S$_2$: Calc'd: C,49.1; H,4.6; N,6.3; Found: C,47.5; H,5.0; N,5.5; Mass spectrum (ES) 441.1 (M+H).

REFERENCE EXAMPLE 108

1-Benzoyl-4-(4-methoxybenzenesulfonyl)-2,3,4,5-tetrahydro-1H-[1,4]benzodiazepine-3-carboxylic acid white foam. Anal. for C$_{24}$H$_{22}$N$_2$O$_6$S: Calc'd C,61.5; H,5.2; N,6.0; Found: C,60.8; H,5.2; N,5.7; Mass spectrum (ES) 467.9 (M+H).

REFERENCE EXAMPLE 109

1-Acetyl-4-(4-methoxybenzenesulfonyl)-2,3,4,5-tetrahydro-1H-[1,4]benzodiazepine-3-carboxylic acid white solid; Anal. for C$_{19}$H$_{22}$N$_2$O$_6$S: Calc'd: C,56.4; H,5.0; N,6.9; Found: C,55.2; H,4.9; N,6.6; S,7.8; Mass spectrum (ES) 404.9 (M+H).

REFERENCE EXAMPLE 110

4-(4-Methoxybenzenesulfonyl)-1-(3-pyridinylcarbonyl)-2,3,4,5-tetrahydro-1H-[1,4]benzodiazepine-3-carboxylic acid white solid; m.p. 250–255. Anal. for C$_{23}$H$_{21}$N$_3$O$_6$S: Calc'd: C,59.1; H,4.5; N,9.0; Found: C,58.3; H,4.7; N,8.3; Mass spectrum (ES): 468.2 (M+H).

REFERENCE EXAMPLE 111

4-(4-Methoxybenzenesulfonyl)-1-(2-thienylcarbonyl)-2,3,4,5-tetrahydro-1H-[1,4]benzodiazepine-3-carboxylic acid white solid; Anal. for C$_{22}$H$_{20}$N$_2$O$_6$S$_2$: Calc'd: C,55.9; H,4.3; N,5.9; Found: C,54.9; H,4.4; N,5.4; Mass spectrum (ES) 473.1 (M+H).

REFERENCE EXAMPLE 112

1-Methoxyacetyl-4-(4-methoxybenzenesulfonyl)-2,3,4,5-tetrahydro-1H-[1,4]benzodiazepine-3-carboxylic acid white crystals, m.p. 193–194° C. Anal. for C$_{20}$H$_{22}$N$_2$O$_7$S: Calc'd: C,55.3; H,5.1; N,6.5; Found: C,55.1; H,4.9; N,6.2; Mass spectrum (ES) 433.1 (M–H).

REFERENCE EXAMPLE 113

4-(4-Methoxybenzenesulfonyl)-1-(4-pyridinylcarbonyl)-2,3,4,5-tetrahydro-1H-[1,4]benzodiazepine-3-carboxylic acid white crystals, m.p. 258–261° C. Anal. for C$_{23}$H$_{21}$N$_3$O$_6$S: Calc'd: C,59.1; H,4.5; N,9.0; Found: C,58.8; H,4.5; N,8.8; Mass spectrum (ES) 483.3 (M+H).

REFERENCE EXAMPLE 114

1-(4-Biphenylcarbonyl)-4-(4-methoxybenzenesulfonyl)-2,3,4,5-tetrahydro-1H-[1,4]benzodiazepine-3-carboxylic acid white foam. Anal. for C$_{30}$H$_{26}$N$_2$O$_6$S: Calc'd: C,66.4; H,4.8; N,5.2; Found: C,64.7; H,5.2; N,4.8; Mass spectrum (ES) 543.6 (M+H).

REFERENCE EXAMPLE 115

4-(4-Methoxybenzenesulfonyl)-1-(propane-1-sulfonyl)-2,3,4,5-tetrahydro-1H-[1,4]benzodiazepine-3-carboxylic acid white foam. Anal. for C$_{20}$H$_{24}$N$_2$O$_7$S$_2$: Calc'd: C,51.3; H,5.2; N,6.0; Found: C,50.3; H,5.3; N,5.7; Mass spectrum (ES) 467.3 (M–H).

REFERENCE EXAMPLE 116

1-([1,1'-Biphenyl]-2-carbonyl)-4-(4-methoxybenzenesulfonyl)-2,3,4,5-tetrahydro-1H-[1,4]benzodiazepine-3-carboxylic acid white foam; m.p. 106–145° C. Anal. for C$_{30}$H$_{26}$N$_2$O$_6$S: Calc'd: C,66.4; H,4.8; N,5.2; Found: C,65.7; H,5.0; N,4.8; Mass spectrum (ES) 541.1 (M–H).

REFERENCE EXAMPLE 117

1-(3-Fluorobenzoyl)-4-(4-methoxybenzenesulfonyl)-2,3,4,5-tetrahydro-1H-[1,4]benzodiazepine-3-carboxylic acid

REFERENCE EXAMPLE 118

4-(4-Methoxybenzenesulfonyl)-1-(2-methyl-3-fluorobenzoyl)-2,3,4,5-tetrahydro-1H-[1,4]benzodiazepine-3-carboxylic acid

REFERENCE EXAMPLE 119

4-(4-Methoxybenzenesulfonyl)-1-(3-phenylpropionyl)-2,3,4,5-tetrahydro-1H-[1,4]benzodiazepine-3-carboxylic acid white solid. Anal. for $C_{26}H_{26}N_2O_6S$: Calc'd: C,63.1; H,5.3; N,5.7; Found: C,61.5; H,5.4; N,5.2; Mass spectrum (ES) 493.2 (M–H).

REFERENCE EXAMPLE 120

4-(4-Methoxybenzenesulfonyl)-1-(2-trifluoromethylbenzoyl)-2,3,4,5-tetrahydro-1H-[1,4]benzodiazepine-3-carboxylic acid

REFERENCE EXAMPLE 121

1-(2-Chloro-6-trifluoromethylbenzoyl)-4-(4-methoxybenzenesulfonyl)-2,3,4,5-tetrahydro-1H-[1,4]benzodiazepine-3-carboxylic acid

REFERENCE EXAMPLE 122

1-(4-Fluoro-2-trifluoromethylbenzoyl)-4-(4-methoxybenzenesulfonyl)-2,3,4,5-tetrahydro-1H-[1,4]benzodiazepine-3-carboxylic acid

REFERENCE EXAMPLE 123

1-(2-Fluoro-6-trifluoromethylbenzoyl)-4-(4-methoxybenzenesulfonyl)-2,3,4,5-tetrahydro-1H-[1,4]benzodiazepine-3-carboxylic acid

REFERENCE EXAMPLE 124

4-(4-Methoxybenzenesulfonyl)-1-(2-methylbenzoyl)-2,3,4,5-tetrahydro-1H-[1,4]benzodiazepine-3-carboxylic acid

REFERENCE EXAMPLE 125

4-(4-Methoxybenzenesulfonyl)-1-(2-methyl-6-chlorobenzoyl)-2,3,4,5-tetrahydro-1H-[1,4]benzodiazepine-3-carboxylic acid

REFERENCE EXAMPLE 126

1-(2,4-Dimethylbenzoyl)-4-(4-methoxybenzenesulfonyl)-2,3,4,5-tetrahydro-1H-[1,4]benzodiazepine-3-carboxylic acid

REFERENCE EXAMPLE 127

1-(2,5-Dimethylbenzoyl)-4-(4-methoxybenzenesulfonyl)-2,3,4,5-tetrahydro-1H-[1,4]benzodiazepine-3-carboxylic acid

REFERENCE EXAMPLE 128

1-(2-Chloro-4-fluorobenzoyl)-4-(4-methoxybenzenesulfonyl)-2,3,4,5-tetrahydro-1H-[1,4]benzodiazepine-3-carboxylic acid

REFERENCE EXAMPLE 129

1-(2-Chlorobenzoyl)-4-(4-methoxybenzenesulfonyl)-2,3,4,5-tetrahydro-1H-[1,4]benzodiazepine-3-carboxylic acid

REFERENCE EXAMPLE 130

1-(2-Fluorobenzoyl)-4-(4-methoxybenzenesulfonyl)-2,3,4,5-tetrahydro-1H-[1,4]benzodiazepine-3-carboxylic acid

REFERENCE EXAMPLE 131

1-(2-Chloro-6-fluorobenzoyl)-4-(4-methoxybenzenesulfonyl)-2,3,4,5-tetrahydro-1H-[1,4]benzodiazepine-3-carboxylic acid

REFERENCE EXAMPLE 132

1-(2,3-Difluorobenzoyl)-4-(4-methoxybenzenesulfonyl)-2,3,4,5-tetrahydro-1H-[1,4]benzodiazepine-3-carboxylic acid

REFERENCE EXAMPLE 133

1-(2,4-Dichlorobenzoyl)-4-(4-methoxybenzenesulfonyl)-2,3,4,5-tetrahydro-1H-[1,4]benzodiazepine-3-carboxylic acid white solid. Anal. for $C_{24}H_{20}Cl_2N_2O_6S$: Calc'd: C,53.8; H,3.8; N,5.2; Found: C,52.8; H,3.9; N,4.9; Mass spectrum (ES) 533 (M–H).

REFERENCE EXAMPLE 134

1-(2,3-Dichlorobenzoyl)-4-(4-methoxybenzenesulfonyl)-2,3,4,5-tetrahydro-1H-[1,4]benzodiazepine-3-carboxylic acid

REFERENCE EXAMPLE 135

1-(2,5-Dichlorobenzoyl)-4-(4-methoxybenzenesulfonyl)-2,3,4,5-tetrahydro-1H-[1,4]benzodiazepine-3-carboxylic acid

REFERENCE EXAMPLE 136

1-(2-Methoxybenzoyl)-4-(4-methoxybenzenesulfonyl)-2,3,4,5-tetrahydro-1H-[1,4]benzodiazepine-3-carboxylic acid

REFERENCE EXAMPLE 137

1-(4-Chloro-2-methoxybenzoyl)-4-(4-methoxybenzenesulfonyl)-2,3,4,5-tetrahydro-1H-[1,4]benzodiazepine-3-carboxylic acid

REFERENCE EXAMPLE 138

4-(4-Methoxybenzenesulfonyl)-1-(2-methylthiobenzoyl)-2,3,4,5-tetrahydro-1H-[1,4]benzodiazepine-3-carboxylic acid

REFERENCE EXAMPLE 139

4-(4-Methoxybenzenesulfonyl)-1-(3-methyl-2-thienylcarbonyl)-2,3,4,5-tetrahydro-1H-[1,4]benzodiazepine-3-carboxylic acid

REFERENCE EXAMPLE 140

4-(4-Methoxybenzenesulfonyl)-1-(4-methyl-2-thienylcarbonyl)-2,3,4,5-tetrahydro-1H-[1,4]benzodiazepine-3-carboxylic acid

REFERENCE EXAMPLE 141

1-(3-Chloro-2-thienylcarbonyl)-4-(4-methoxybenzenesulfonyl)-2,3,4,5-tetrahydro-1H-[1,4]benzodiazepine-3-carboxylic acid

REFERENCE EXAMPLE 142

1-(2-Furanylcarbonyl)-4-(4-methoxybenzenesulfonyl)-2,3,4,5-tetrahydro-1H-[1,4]benzodiazepine-3-carboxylic acid white solid. Anal. for $C_{22}H_{20}N_2O_7S$: Calc'd: C, 57.9; H, 4.4; N, 6.1; Found: C, 56.5; H, 4.5; N, 5.7; Mass spectrum (ES) 455.1 (M–H).

REFERENCE EXAMPLE 143

4-(4-Methoxybenzenesulfonyl)-1-(3-methyl-2-furanylcarbonyl)-2,3,4,5-tetrahydro-1H-[1,4]benzodiazepine-3-carboxylic acid

REFERENCE EXAMPLE 144

4-(4-Methoxybenzenesulfonyl)-1-(4-methyl-2-furanylcarbonyl)-2,3,4,5-tetrahydro-1H-[1,4]benzodiazepine-3-carboxylic acid

REFERENCE EXAMPLE 145

1-(5-Chloro-2-furanylcarbonyl)-4-(4-methoxybenzenesulfonyl)-2,3,4,5-tetrahydro-1H-[1,4]benzodiazepine-3-carboxylic acid

REFERENCE EXAMPLE 146

1-(5-Chloro-2-thienylcarbonyl)-4-(4-methoxybenzenesulfonyl)-2,3,4,5-tetrahydro-1H-[1,4]benzodiazepine-3-carboxylic acid

REFERENCE EXAMPLE 147

1-Propionyl-4-(4-methoxybenzenesulfonyl)-2,3,4,5-tetrahydro-1H-[1,4]benzodiazepine-3-carboxylic acid

REFERENCE EXAMPLE 148

1-Hexanoyl-4-(4-methoxybenzenesulfonyl)-2,3,4,5-tetrahydro-1H-[1,4]benzodiazepine-3-carboxylic acid

REFERENCE EXAMPLE 149

1-(3-Methoxypropionyl)-4-(4-methoxybenzenesulfonyl)-2,3,4,5-tetrahydro-1H-[1,4]benzodiazepine-3-carboxylic acid

REFERENCE EXAMPLE 150

4-(4-Methoxybenzenesulfonyl)-1-(3-thienylcarbonyl)-2,3,4,5-tetrahydro-1H-[1,4]benzodiazepine-3-carboxylic acid

REFERENCE EXAMPLE 151

4-(3-Furanylcarbonyl)-4-(4-methoxybenzenesulfonyl)-2,3,4,5-tetrahydro-1H-[1,4]benzodiazepine-3-carboxylic acid

REFERENCE EXAMPLE 152

1-(trans-Crotonyl)-4-(4-methoxybenzenesulfonyl)-2,3,4,5-tetrahydro-1H-[1,4]benzodiazepine-3-carboxylic acid

REFERENCE EXAMPLE 153

1-(Methacryloyl)-4-(4-methoxybenzenesulfonyl)-2,3,4,5-tetrahydro-1H-[1,4]benzodiazepine-3-carboxylic acid

REFERENCE EXAMPLE 154

1-(Pyrrolidinoacetyl)-4-(4-methoxybenzenesulfonyl)-2,3,4,5-tetrahydro-1H-[1,4]benzodiazepine-3-carboxylic acid

REFERENCE EXAMPLE 155

1-(Acetylaminoacetyl)-4-(4-methoxybenzenesulfonyl)-2,3,4,5-tetrahydro-1H-[1,4]benzodiazepine-3-carboxylic acid

REFERENCE EXAMPLE 156

1-(Cyclopropylcarbonyl)-4-(4-methoxybenzenesulfonyl)-2,3,4,5-tetrahydro-1H-[1,4]benzodiazepine-3-carboxylic acid white crystals, m.p. 131–135° C. Anal. for $C_{21}H_{22}N_2O_6S$: Calc'd: C,58.6; H,5.2; N,6.5; Found: C,58.1; H,5.5; N,5.8; Mass spectrum (ES) 431.5 (M+H).

REFERENCE EXAMPLE 157

1-(Cyclobutylcarbonyl)-4-(4-methoxybenzenesulfonyl)-2,3,4,5-tetrahydro-1H-[1,4]benzodiazepine-3-carboxylic acid

REFERENCE EXAMPLE 158

1-(Cyclohexylcarbonyl)-4-(4-methoxybenzenesulfonyl)-2,3,4,5-tetrahydro-1H-[1,4]benzodiazepine-3-carboxylic acid white solid. Anal. for $C_{24}H_{28}N_2O_6S$: Calc'd: C,61.0; H,6.0; N,5.9; Found: C,57.0; H,5.7; N,5.4; Mass spectrum (ES) 471.5 (M–H).

REFERENCE EXAMPLE 159

(D,L)N-(4-Methoxybenzenesulfonyl)-O-(2-tetrahydropyranyl)serine, Methyl ester

A mixture of 1.44 g (5 mmol) of N-(4-methoxybenzenesulfonyl)serine, methyl ester; 1.05 g (12.5 mmol) of 3,4-dihydro-2H-pyran and 9.5 mg of 4-methylbenzenesulfonic acid monohydrate in 5 ml of tetrahydrofuran was refluxed overnight and the mixture was concentrated to dryness under vaccum. The residue was extracted with $CH_2Cl_2$ and the extract washed with 2 N $NaHCO_3$, brine and dried with $Na_2SO_4$. The solution was filtered through a thin pad of hydrous magnesium silicate and the filter pad washed with $CH_2Cl_2$. The filtrate was concentrated to dryness and the residue (2.3 g) was extracted with three 50 ml portions of hot hexane to give 1.92 g of product as a yellow oil; Mass spectrum (ES) 374.4 (MH$^+$).

REFERENCE EXAMPLE 160

Methyl 3-Hydroxy-2-{[4-methoxybenzenesulfonyl]-[2-(4-morpholinocarbonylamino)benzyl]amino}propionate To a mixture of 1.0 g (2.54 mmol) of methyl 2-[(2-aminobenzyl)-(4-methoxybenzenesulfonyl)amino]-3-hydroxypropionate in 8 ml of pyridine chilled at 0° to –10° C. was added 740 μL (6.34 mmol) of morpholinocarbonyl chloride. The mixture was kept at 0° to 5° C. overnight. The mixture was concentrated under vacuum and diluted with ethyl acetate. The solution was washed with $H_2O$, 2 N citric acid, and brine and dried with $Na_2SO_4$. The solvent was removed under vacuum to give 1.61 g of solid (yellow-orange foam). The solid was chromatographed on thick layer silica gel plates with hexane-ethyl acetate (1:3) as solvent to give 0.86 g of solid. Anal. for $C_{23}H_{29}N_3O_8S$: Calc'd: C,54.4; H,5.8; N,8.3; Found: C,53.9; H,5.7; N,8.1: Mass spectrum (ES) 508.4 (M+H).

REFERENCE EXAMPLE 161

Methyl 2-{(4-Methoxybenzenesulfonyl)-[2-(4-morpholinocarbonylamino)benzyl]amino acrylate To a solution of 0.70 g (1.38 mmol) of methyl 3-hydroxy-2-{[4-methoxybenzenesulfonyl]-[2-(4-morpholinocarbonylamino)benzyl]amino}propionate and 769 μL (5.54 mmol) of triethylamine in 8 ml of $CH_2Cl_2$, cooled to 0° C., was added 0.386 g (2.03 mmol) of 4-methylbenzenesulfonyl chloride. The mixture was stirred at room temperature for 2 hours, diluted with water and extracted with $CH_2Cl_2$. The extract was washed with 2 N citric acid, brine and dried with $Na_2SO_4$. The solvent was removed to give 0.67 g of a yellow oil. Anal. for $C_{23}H_{27}N_3O_7S$: Calc'd: C,56.4; H,5.6; N,8.6; S.6.6; Found: C,56.1; H,5.8; N,8.3; S,6.6.

REFERENCE EXAMPLE 162

Methyl 4-(4-Methoxybenzenesulfonyl)-1-(4-morpholinocarbonyl)-2,3,4,5-tetrahydro-1H-[1,4]-benzodiazepine-3-carboxylate A mixture of 0.50 g (1.02 mmol) of methyl 2-{(4-methoxybenzenesulfonyl)-[2-(4-morpholinocarbonyl-amino)benzyl]amino}acrylate and 0.111 g (1.32 mmol) of anhydrous $NaHCO_3$ in 5 ml of anhydrous methanol was stirred at room temperature for 16 hours. An additional 55 mg of $NaHCO_3$ was added and the mixture stirred at room temperature for 2 hours. The solvent was removed under vacuum and the residue diluted with $H_2O$ and extracted with ethyl acetate. The extract was washed with brine and dried with $Na_2SO_4$. The solvent was removed and the residue triturated with hexane-ethyl acetate to give 0.36 g of a yellow solid, Anal. calc'd for $C_{23}H_{27}N_3O_7S$: C,56.4; H,5.6; N,8.6; S,6.6. Found: C,56.5; H,5.7; N,8.4; S,6.7; Mass spectrum (ES) 490.3 (M+H).

REFERENCE EXAMPLE 163

4-(4-Methoxybenzenesulfonyl)-1-(4-morpholinocarbonyl)-2,3,4,5-tetrahydro-1H-[1,4]benzodiazepine-3-carboxylic Acid A mixture of 0.36 g (0.735 mmol) of methyl 4-(4-methoxybenzenesulfonyl)-1-(4-morpholinocarbonyl)-2,3,4,5-tetrahydro-1H-[1,4]benzodiazepine-3-carboxylate and 1 ml (0.95 mmol) of 1 N NaOH in 5 ml of tetrahydrofuran was stirred at room temperature for 1 hour. The mixture was concentrated under vacuum and the acidified with 1 N HCl and cooled. The mixture was filtered and the solid washed with water to give 0.26 g of white solid. Anal. for $C_{22}H_{25}N_3O_7S$: Calc'd: C,55.6; H,5.3; N,8.8; Found: C,53.5; H,5.6; N,8.3; Mass spectrum (ES) 474.3 (M–H).

REFERENCE EXAMPLE 164

Methyl 3-[(2-Tetrahydropyranyl)oxy]-2-[(4-methoxybenzenesulfonyl)-(2-nitro-4-chlorobenzyl)amino]propionate To a mixture of 1.67 g (4.4 mmol) of (D,L) N-(4-methoxybenzenesulfonyl)-O-(2-tetrahydropyranyl) serine, methyl ester, 0.825 g, (4.4 mol) of 4-chloro-2-nitrobenzyl alcohol and 1.16 g (4.4 mmol) of triphenylphosphine in 4.5 ml of tetrahydrofuran was added dropwise a solution of 0.766 g (4.4 mmol) of diethyl azodicarboxylate in 1 ml of tetrahydrofuran. The mixture was stirred at room temperature overnight and the solvent removed under vacuum. The residue was triturated with diethyl ether, filtered and the filtrate passed through a thin pad of hydrous magnesium silicate. The pad was washed with ethyl acetate and the total filtrate concentrated to dryness under vacuum to give 4.54 g of solid. The solid was chromatographed on silica gel with hexane-ethyl acetate (55:45) as solvent. The fractions containing product were combined and the solvent removed to give 0.55 g of oily solid; Mass spectrum (ES) 543.1 (M+H).

REFERENCE EXAMPLE 165

Methyl 2-{[2-(4-Pyridinylmethyleneamino)benzyl]-[4-methoxybenzenesulfonyl]amino}-3-hydroxypropionate A mixture of 0.50 g (1.268 mmol) of methyl 2-[(2-aminobenzyl)-(4-methoxybenzenesulfonyl)amino]-3-hydroxypropionate and 1.268 mmol of 4-pyridinecarboxaldehyde in 7 ml of anhydrous ethanol was refluxed for 1.5 hours and the mixture concentrated under vacuum to dryness. To the residue was added $H_2O$ and ethyl acetate. The ethyl acetate layer was separated and concentrated to dryness under vacuum. The solid was purified by thick layer chromatography on silica gel with hexane-ethyl acetate as solvent to give 0.40 g of solid product (plus a small amount of starting material). Anal. for $C_{24}H_{25}N_3O_6S$: Calc'd: C,59.6; H,5.2; N,8.7; Found: C,57.6; H,5.7; N,7.4; Mass spectrum (ES) 484 (M+H)-product; 395.1 (M+H)-starting material.

REFERENCE EXAMPLE 166

Methyl 1-(Cyclohexylcarbonyl)-4-(4-methoxybenzenesulfonyl)-2,3,4,5-tetrahydro-1H-[1,4]benzodiazepine-3-carboxylate To a solution of 0.80 g (1.64 mmol) of methyl 2-{[2-(cyclohexylcarbonyl)-aminobenzyl]-(4-methoxybenzenesulfonyl)amino}acrylate in 10 ml of methanol was added 0.207 g (2.46 mmol) of anhydrous sodium bicarbonate. The mixture was stirred for 2 days and then an additional 0.207 g of $NaHCO_3$ added. The mixture was stirred overnight and the solvent removed under vacuum. To the residue was added $H_2O$ and ethyl acetate and the organic layer separated. The ethyl acetate extract was washed with brine, dried with $Na_2SO_4$ and the solvent removed under vacuum to give 0.83 g of the product as a yellow oil. Anal. for $C_{25}H_{30}N_2O_6S$: Calc'd: C,61.7; H,6.2; N,5.8; Found: C,61.0; H,6.4; N,5.3; Mass spectrum (ES) 487.0 (M+H).

REFERENCE EXAMPLE 167

Methyl 3-Hydroxy-2-[(4-methoxybenzenesulfonyl)-(4-chloro-2-nitrobenzyl)amino]propionate To a solution of 0.289 g (1 mmol) of methyl 3-hydroxy-2-(4-methoxybenzenesulfonylamino)propionate in 4 ml of N,N-dimethylformamide cooled in an ice bath was added 40 mg of NaH (60% in oil) (1 mmol). After the gas evolution ceased, 0.165 g (1.1 mmol) of sodium iodide was added, followed by the addition of 0.226 g (1.1 mmol) of 4-chloro-2-nitrobenzyl chloride in 1 ml of dimethylformamide.

The solution became purple and was stirred at room temperature over the weekend.

The solvent was removed under vacuum and the residue extracted with $CH_2Cl_2$. The extract was washed with $H_2O$, brine and dried with $Na_2SO_4$. The solvent was removed to give 0.53 g of solid which was chromatographed on thick layer silica gel plates with hexane-ethyl acetate (2:1) as solvent to give 0.143 g (31%) of product, as crystals, m.p. 112°–114° C. Anal. for $C_{18}H_{19}ClN_2O_8S$: Calc'd: C,47.2; H,4.2; N,6.1; Found: C,47.0; H,4.1; N,6.0; Mass spectrum (ES) 459.2 (M+H).

REFERENCE EXAMPLE 168

Methyl 3-Hydroxy-2-[(4-methoxybenzenesulfonyl)-(4-chloro-2-aminobenzyl)amino]propionate A mixture of 0.454 g (1 mmol) of methyl 3-hydroxy-2-[(4-methoxybenzenesulfonyl)-(4-chloro-2-nitrobenzyl)amino]propionate and 0.451 g (2 mmol) of $SnCl_2.2H_2O$ in 12 ml of methanol was refluxed for 2 hours. An additional 0.451 g (2 mmol) of $SnCl_2.2H_2O$ was added and the mixture refluxed for 2 hours.

The solvent was removed and ethyl acetate added. The mixture was neutralized with 1 N $NaHCO_3$ and then stirred for 1 hour and filtered. The ethyl acetate layer was separated and washed with $H_2O$, brine and dried with $Na_2SO_4$. The solvent was removed to give 0.42 g of solid which was chromatographed on thick layer silica gel plates with hexane-ethyl acetate (45:55) as solvent to give 60 mg of product ($R_F$ 0.66) as a glass. m.p. 99°–112° C. Anal. for $C_{18}H_{21}ClN_2O_6S$: Calc'd: C,50.4; H,4.9; N,6.5; Found: C,49.7; H,4.9; N,6.4; Mass spectrum (ES) 429.1 (M+H).

REFERENCE EXAMPLE 169

Methyl 3-Hydroxy-2-[(4-methoxybenzenesulfonyl)-(4-chloro-2-aminobenzyl)amino]propionate To a solution of 0.458 g (1 mmol) of methyl 3-hydroxy-2-[(4-methoxybenzenesulfonyl)-(4-chloro-2-nitrobenzyl) amino]propionate in 25 ml of ethanol and 25 ml of ethyl acetate was added 0.045 g of 10% Pd/C (wet—50% $H_2O$).

The mixture was shaken in a Parr hydrogenator under 35 pounds per square inch of hydrogen for 3 hours. The mixture was filtered through diatomaceous earth and the filtrate was concentrated to dryness under vacuum to give 0.47 g of the product as a solid (approximately 90% pure). Thin layer chromatography on silica gel, NMR and Mass spectrum (ES) 429.1 (M+H) 395.1 (M+H) indicated approximately 10% of deschloro derivative.

A mixture of 4.74 g of methyl 3-hydroxy-2-[(4-methoxybenzenesulfonyl)-(4-chloro-2-aminobenzyl) amino}propionate, and 0.470 g of 10% Pd/C (wet—50% $H_2O$) in 200 ml of ethyl acetate-ethanol (1:1) was shaken in a Parr hydrogenator under 35 psi of hydrogen for 4 hours. The mixture was filtered through diatomaceous earth and the solvent removed to give 4.5 g of solid. The solid was chromatographed by HPLC on a Waters Prep machine with a 4×30 cm silica gel column with a step gradient of hexane-ethyl acetate (9:1 to 6:4 to 1:1 to 0:100) to give 1.56 g of a class, m.p. 110°–123° C. Anal. for $C_{18}H_{21}ClN_2O_6S$: Calc'd: C, 50.4; H, 4.9; N, 6.5; Cl, 8.3; Found: C, 50.3; H, 4.8; N, 6.5; Cl, 7.8.

REFERENCE EXAMPLE 170

N-(4-Methoxybenzenesulfonyl)-glycine, Methyl Ester

To a mixture of 12.5 g (0.1 mol) of glycine, methyl ester hydrochloride in 120 ml of $CH_2Cl_2$, cooled in an ice bath was added 41.7 ml (0.3 mol) of triethylamine, followed by the dropwise addition of a solution of 20.65 g (0.1 mol) of 4-methoxybenzenesulfonyl chloride in 40 ml of $CH_2Cl_2$. The mixture was stirred at room temperature overnight and poured into water. The organic layer was separated and washed with 2 N citric acid, $H_2O$, 1 N $NaHCO_3$, brine and dried with $Na_2SO_4$. The solvent was removed under vacuum to give 24.6 g of residue which was triturated with ethyl acetate to give 19.9 g of crystals, m.p. 59°–61° C. Anal. for $C_{10}H_{13}NSO_5$: Calc'd: C,46.3; H,5.1; N,5.4; Found: C,46.2; H,5.0; N,5.2.

REFERENCE EXAMPLE 171

Methyl 2-[(4-methoxybenzenesulfonyl)-(2-nitrobenzyl)amino]acetate

To a stirred and cooled mixture of 1.2 g (30 mmol) of NaH (58% in oil) in 50 ml of N,N-dimethylformamide was added dropwise a solution of 7.78 g (30 mmol) of N-(4-methoxybenzenesulfonyl)-lycine, methyl ester in 40 ml of N,N-dimethylformamide. After gas evolution ceased, a solution of 6.80 g, (32 mmol) of 2-nitrobenzyl bromide in 40 ml of N,N-dimethylformamide was added dropwise to the mixture. The mixture was then stirred at room temperature overnight under nitrogen and the solvent removed under vacuum. The residue was extracted with $CH_2Cl_2$ and the extract washed with $H_2O$, 2 N citric acid, $H_2O$, 1 N $NaHCO_3$. brine and dried with $Na_2SO_4$. The solution was filtered through a thin pad of hydrous magnesium silicate and the filter pad washed with $CH_2Cl_2$. The filtrate was concentrated under vacuum to give 11.79 g of solid. Trituration with ethyl acetate gave 2.64 (22%) of crystals, m.p. 114°–116° C. Anal. for $C_{17}H_{18}N_2O_7S$: Calc'd: C,51.8; H,4.6; N,7.1; Found: C,51.7; H,4.6; N,7.1.

From the mother liquors an additional 6.49 g (55%) of product as crystals was obtained by chilling at 0° C. and filtering the mother liquors.

REFERENCE EXAMPLE 172

Methyl 2-[(2-Aminobenzyl)-(4-methoxybenzenesulfonyl)amino]acetate (A) To a mixture of 2.15 g (5.45 mmol) of methyl-2-[(4-methoxybenzenesulfonyl)-(2-nitrobenzyl)amino]acetate and 1.57 g (25 mmol) of ammonium formate in 10 ml of anhydrous methanol was added 0.42 g of 10% palladium on carbon. The mixture was stirred at room temperature for 1.5 hours and then filtered through diatomaceous earth. The filtrate was concentrated to dryness under vacuum and the residue diluted with $H_2O$ (25 ml) and extracted with $CH_2Cl_2$ (75 ml). The extract was washed with brine, dried with $Na_2SO_4$ and the solvent removed to give 0.45 g of solid. Crystallization from ethyl acetate gave 0.124 g of white crystals, m.p. 100°–102° C. Anal. for $C_{17}H_{20}N_2O_5S$: Calc'd: C,56.0; H,5.5; N,7.7; Found: C,56.1; H,5.6; N,7.6.

(B) To a solution of 4.2 g of methyl 2-[(4-methoxybenzenesulfonyl)-(2-nitrobenzyl)amino]acetate in 200 ml of ethanol-ethyl acetate (1:1) was added 0.42 g of 10% Pd on carbon (wet—50% $H_2O$) and the mixture shaken in a Parr hydrogenator under 35 pounds per square inch of hydrogen for 4.5 hours at room temperature. The mixture was filtered through diatomaceous earth and the filtrate concentrated to dryness under vacuum to give 4.0 g of crystals. m.p. 100°–102° C.

REFERENCE EXAMPLE 173

2-[(2-Aminobenzyl)-(4-methoxybenzenesulfonyl) amino]acetic Acid

To a solution of 5.14 g (14.1 mmol) of methyl 2-[(2-aminobenzyl)-(4-methoxybenzenesulfonyl)amino]acetate in 50 ml of methanol-tetrahydrofuran (1:1) was added 2.86 ml of 10 N NaOH and the mixture refluxed for 2 hours. The solvent was removed under vacuum and the residue partitioned between water and ether. The water layer was separated and acidified with 2 N citric acid. The solid was filtered, washed with $H_2O$ and dried in a vacuum oven at room temperature to give 4.45 g (91%) of crystals, m.p. 145°–147° C. Anal. for $C_{16}H_{18}N_2O_5S$: Calc'd: C,54.9; H,5.2; N,8.0; Found: C,55.1; H,5.2; N,7.9.

REFERENCE EXAMPLE 174

Methyl 4-(4-Methoxybenzenesulfonyl)-1-(phenoxyacetyl)-2,3,4,5-tetrahydro-1H-[1,4] benzodiazepine-3-carboxylate To a cooled (0° C.) mixture of 1.5 g (3.8 mmol) of methyl 2-[(2-aminobenzyl)-(4-methoxybenzenesulfonyl)amino]-3- hydroxypropionate and 2.7 ml (19 mmol) of triethylamine in 15 ml of $CH_2Cl_2$ was added 1.58 g (11.4 mol) of phenoxyacetyl chloride. The mixture was stirred at room temperature overnight and filtered. The filtrate was washed with $H_2O$, 2 N citric acid, and brine and dried with $Na_2SO_4$. The solvent was removed to give 2.4 g of crude methyl 2-{(4-methoxybenzenesulfonyl)-[2-(phenoxyacetylamino)benzyl]amino}acrylate as an oil. Anal. for $C_{26}H_{26}N_2O_7S$: Calc'd: C,61.2; H,5.1; N,5.5; Found: C,62.6; H,5.1; N,4.0; Mass spectrum (ES) 511 (M+H).

To a 2.0 g (3.92 mmol) sample of the preceding compound in 15 ml of methanol was added 0.494 g of anhydrous $NaHCO_3$ and the mixture stirred for 5 hours. The mixture was concentrated under vacuum and ethyl acetate and $H_2O$ were added to the residue. The mixture was filtered and the organic layer of the filtrate separated, washed with brine and dried with $Na_2SO_4$. The solvent was removed to give 0.36 g of product as off-white crystals, m.p. 151°–153° C. Anal. for $C_{26}H_{26}N_2O_7S$: Calc'd: C,61.2; H,5.1; N,5.5; Found: C,61.1; H,5.1; N,5.4; Mass spectrum (ES) 511 (M+H).

REFERENCE EXAMPLE 175

3-hydroxymethyl-4-(4-Methoxybenzenesulfonyl)-1-(3-pyridinylmethyl)-2,3,4,5-tetrahydro-1H-[1,4]benzodiazepine A mixture of 0.100 g (0.208 mmol) of methyl 4-(4-methoxybenzenesulfonyl)-1-(3-pyridinylcarbonyl)-2,3,4,5-tetrahydro-1H-[1,4]benzodiazepine-3-carboxylate and 3 ml of borane-tetrahydrofuran complex in tetrahydrofuran (1.0 M) was refluxed overnight. The solution was cooled to room temperature, diluted with methanol and the solvent removed. Methanol was added several times and, after each addition, the solvent was removed. To the residue was added 1N $NaHCO_3$. The mixture was stirred for 45 minutes and then extracted with ethyl acetate. The extract was concentrated and then washed with $H_2O$, brine and dried with $Na_2SO_4$. The solvent was removed under vacuum and the residue chromatographed on thick layer silica gel plates with 10% methanol in ethyl acetate as solvent to give 60 mg of solid ($R_F$ 0.26). Crystallization from ethyl acetate gave 30 mg of white crystals. Anal. for $C_{23}H_{25}N_3O_4S$: Calc'd: C,62.8; H,5.7; N,9.6; S,7.3; Found: C,61.1; H,5.6; N,9.2; S,7.3; Mass spectrum (ES) 440.2 (M+H).

REFERENCE EXAMPLE 176

Methyl 4-(4-Methoxybenzenesulfonyl)-1-(2-methoxypyridinyl-3-carbonyl)-2,3,4,5-tetrahydro-1H-[1,4]benzodiazepine-3-carboxylate To a cooled (0° C.) mixture of 1.0 g (2.54 mmol) of methyl 2-[(2-aminobenzyl)-(4-methoxybenzenesulfonyl)amino]-3-hydroxypropionate and 1.8 ml (12.68 mmol) of triethylamine in 10 ml of $CH_2Cl_2$ was added 0.957 g (5.58 mmol) of 2-methoxypyridine-3-carbonyl chloride in 4 ml of $CH_2Cl_2$. The solution was stirred at room temperature overnight, diluted with $H_2O$ and $CH_2Cl_2$ and the organic layer separated. The organic layer was washed with $H_2O$, 2N citric acid, and brine and dried with $Na_2SO_4$. The solvent was removed under vacuum to give 1.2 g of solid. The solid was chromatographed on thick layer silica gel plates with ethyl acetate-hexane (3:1) as solvent to give 0.27 g of yellow foam. Anal. for $C_{25}H_{25}N_3O_7S$: Calc'd: C,58.7, H,4.93; N,8.21; Found: C,57.8; H.4.5; N,8.3; S,6.2.

REFERENCE EXAMPLE 177

5-Methyl-2-nitrobenzyl Bromide

To a cooled (ice-water bath) mixture of 30% HBr in acetic acid (3 ml) was added 2.5 g 5-methyl-2-nitrobenzyl alcohol and the chilled solution stirred for 2 hours. The mixture was poured into ice-water and extracted with diethyl ether. The extract was washed with $H_2O$, brine and the solvent removed under vacuum to give a mixture of product (50%) and starting material (50%).

REFERENCE EXAMPLE 178

Methyl 3-Hydroxy-2-[(4-methoxybenzenesulfonyl)-(5-methyl-2-nitrobenzyl)amino]propionate A solution of 23.14 g (0.08 mol) of methyl 3-hydroxy-2-(4-methoxybenzenesulfonylamino)propionate in 120 ml of dry N,N-dimethylformamide was added dropwise to a stirred suspension of 3.2 g (0.08 mol) of sodium hydride (57% in oil) in 120 ml of N,N-dimethylformide. When gas evolution ceased, the mixture was chilled in an ice bath and a solution of 16.4 g (0.084 mol) of 5-methyl-2-nitrobenzyl chloride in 100 ml of N N-dimethylformamide was added. To the mixture was added 12.6 g (0.084 mol) of anhydrous sodium iodide and the mixture was chilled in an ice bath and stirred for 20 minutes. The mixture was allowed to warm to room temperature and was stirred overnight. The solvent was removed under vacuum and the residue diluted with 200 ml of $H_2O$ and extracted with 500 ml of ethyl acetate. The aqueous layer was extracted with an additional 200 ml of ethyl acetate. The combined extract was washed with $H_2O$, brine and dried with $Na_2SO_4$. The solvent was removed to give 41.18 g of crude product. The product was chromatographed on silica gel with hexane-ethyl acetate (1:1) as solvent to give 8.14 g ($R_F$ 0.38) of product as a yellow semi-solid. From a small scale run (1 mmol) the product was chromatographed twice on thick silica gel plates with hexane-ethyl acetate (1:1) to give 0.12 g of a yellow semi-solid. Anal. for $C_{19}H_{22}N_2SO_8$: Calc'd: C,52.0; H,5.1; N,6.4: Found: C,51.7; H,5.1; N,6.0.

REFERENCE EXAMPLE 179

Methyl 3-Hydroxy-2-[(4-methoxybenzenesulfonyl)-(2-amino-5-methylbenzyl)amino]propionate To a solution of 3.4 g of methyl 3-hydroxy-2-[(4-methoxybenzenesulfonyl)-(5-methyl-2-nitrobenzyl)-amino]propionate in 200 ml of ethanol-ethyl acetate (1:1) was added 0.34 g of 10% palladium on carbon (wet –50% $H_2O$). The mixture was then shaken in a Parr hydrogenator under 35 psi of hydrogen for 2.5 hours. The mixture was filtered through diatomaceous earth and the filtrate concentrated under vacuum to give 2.86 a of a brown oil. Anal. for $Cl_{19}H_4N_2O_6S$: Calc'd: C,55.9; H,5.9; N,6.9: Found: C,55.6; H,5.9; N,6.4: Mass spectrum (ES) 409 (M+H).

REFERENCE EXAMPLE 180

Methyl 3-[(2-Tetrahydropyranyl)oxy]-2-[(-4-methoxybenzenesulfonyl)-(5-methyl-2-nitrobenzyl)amino]propionate To a mixture of 1.75 g (4.68 mmol) of (D,L)N-(4-methoxybenzenesulfonyl)-O-(2-tetrahydropyranyl) serine, methyl ester, 0.790 g (4.68 mmol) of 5-methyl-2-nitrobenzyl alcohol and 1.23 g (4.68 mmol) of triphenylphosphine in 4.5 ml of anhydrous tetrahydrofuran was added dropwise (over 15 minutes) a solution of 0.815 g (4.68 mmol) of diethyl azodicarboxylate (DEAD) in 1 ml of tetrahydrofuran. The mixture was stirred at room temperature overnight and the solvent removed under vacuum. The residue was triturated with diethyl ether and the solid filtered off. The filtrate was concentrated to dryness under vacuum to give 4.67 g of solid. The solid was chromatographed on silica gel with hexane-ethyl acetate (1:1) to give 0.56 g of product ($R_F$ 0.48).

REFERENCE EXAMPLE 181

Methyl 1-Methoxyacetyl-4-(4-methoxybenzenesulfonyl)-7-methyl-2,3,4,5-tetrahydro-1H-[1,4]benzodiazepine-3-carboxylate To a cooled (0° C.) mixture of 1.598 g (3.91 mmol) of methyl 3-hydroxy-2-[(4-methoxybenzenesulfonyl)-(2-amino-5-methylbenzyl)amino]propionate and 1.97 g (19.5 mmol) of triethylamine in 15 ml of dichloromethane was added 0.787 ml (8.60 mmol) of methoxyacetylchloride. The mixture was stirred at room temperature overnight. The mixture was then diluted with $CH_2Cl_2$ and washed with $H_2O$, 2N citric acid, $H_2O$, brine and dried with $Na_2SO_4$. The solution was filtered through a thin pad of hydrous magnesium silicate and the filtrate concentrated to give 1.94 g of crude methyl 2-{[2-(methoxyacetylamino)-5-methylbenzyl]-(4-methoxy-benzenesulfonyl)-amino}acrylate as a brown oil. Mass spectrum (ES) 463.4 (M+H).

To a solution of 1.62 g (3.5 mmol) of the preceding compound in 15 ml of anhydrous methanol was added 0.382 g (4.50 mmol) of anhydrous $NaHCO_3$ and the mixture was stirred overnight at room temperature. The solvent was removed under vacuum and the residue partitioned between 100 ml of ethyl acetate and 20 ml of water. The ethyl acetate layer was separated and washed with $H_2O$, brine and dried with $Na_2SO_4$. The solution was filtered through a thin pad of hydrous magnesium silicate and the filtrate concentrated under vacuum to give a yellow oil. Trituration with ethyl acetate-hexane gave 1.26 g (78%) of tan crystals, m.p. 122–124° C. Anal. for $C_{22}H_{26}N_2O_7S$: Calc'd: C.57.1; H,5.7; N,6.1; Found: C,57.4; H,5.7; N,6.0.

REFERENCE EXAMPLE 182

Methyl 1-Benzoyl-4-(4-methoxybenzenesulfonyl)-7-methyl-2,3,4,5-tetrahydro-1H-[1,4]benzodiazeprine-3-carboxylate To a cooled (0° C.) mixture of 1.465 g (3.586 mmol) of methyl 3-hydroxy-2-[4-methoxybenzenesulfonyl)-(2-amino-5-methylbenzyl)amino]propionate and 2.49 ml (17.93 mmol) of triethylamine in 20 ml of $CH_2Cl_2$ was added 0.915 ml (7.89 mmol) of benzoyl chloride. The mixture was stored at room temperature overnight, diluted with $CH_2Cl_2$ and washed with $H_2O$, 2N citric acid, $H_2O$, brine and dried with $Na_2SO_4$. The solution was filtered through a thin pad of hydrous magnesium silicate and the filtrate concentrated under vacuum to give 1.8 g of crude methyl 2-[(2-benzoylamino-5-methylbenzyl)-(4-methoxybenzenesulfonyl)amino]acrylate as a brown oil. Anal. for $C_{26}H_{26}N_2O_6S$: Calc'd: C,63.1; H,5.3; N,5.7; Found: C,63.9; H,5.2; N,5.2.

As described for Reference Example 181, 1.825 g (3.68 mmol) of the preceding compound was stirred with 0.402 g (4.78 mmol) of $NaHCO_3$ in 1.5 ml of methanol to give an oil. Trituration with hexane (plus several drops of ethyl acetate) gave crystals, m.p. 58°–62° C.

REFERENCE EXAMPLE 183

Methyl 1-(trans-Crotonyl)-4-(4-methoxybenzenesulfonyl)-7-methyl-2,3,4,5-tetrahydro-1H-[1,4]benzadiazepine-3-carboxylate As described for Reference Examples 181 and 182, a mixture of 1.41 g (3.455 mmol) of methyl 3-hydroxy-2-[-(4-methoxybenzenesulfonyl)-(2-amino-5-methylbenzyl)amino]propionate, 1.75 g (17.3 mmol) of triethylamine and 0.809 ml of trans-crotonyl chloride in 15 ml of $CH_2Cl_2$ was stirred overnight to give 1.52 g of methyl 2-{[2-(trans-crotonylamino)-5-methylbenzyl]-(4-methoxybenzenesulfonyl) amino}acrylate as a brown oil; Mass spectrum (ES) 459.4 (M+H).

As described in Reference Example 181, 1.52 g (3.31 mmol) of the preceding product was stirred with 0.362 g (4.3 mmol) of $NaHCO_3$ in 15 ml of methanol at room temperature overnight. To the mixture was added 0.056 g of $NaHCO_3$ and the mixture was heated at 80° C. for 3 hours and worked up as for Reference Example 181 to give a 1.05 g of a yellow glass. m. p. 75°–84° C. Mass spectrum (ES) 459.4 (M+H).

REFERENCE EXAMPLE 184

1-(trans-Crotonyl)-4-(4-methoxybenzenesulfonyl)-7-methyl-2,3,4,5-tetrahydro-1H-[1,4]benzodiazepene-3-carboxylic acid A mixture of 1.26 g (2.72 mmol) of methyl 1-(trans-crotonyl)-4-(4-methoxybenzenesulfonyl)-7-methyl-2,3,4.5-tetrahydro-1H-[1,4]benzodiazepine-3-carboxylate and 3.53 ml (3.53 mmol) of 1N NaOH in 10 ml of tetrahydrofuran was stirred at room temperature for 3 hours. The solvent was removed under vacuum and the residue dissolved in $H_2O$ and the solution extracted with ethyl acetate. The aqueous layer was acidified with 1N HCl (pH 2) and extracted with $CH_2Cl_2$. The $CH_2Cl_2$ extract was dried with $Na_2SO_4$ and the solvent removed to give 1.06 g (after drying under vacuum) of solid, m.p. 101°–105° C.

REFERENCE EXAMPLE 185

1-(Benzoyl)-4-(4-methoxybenzenesulfonyl)-7-methyl-2,3-4,5-tetrahydro-1H[1,4]benzodiazepine-3-carboxylic acid A mixture of 1.18 g, (2.38 mmol) of methyl 1-(benzoyl)-4-(4-methoxybenzenesulfonyl)-7-methyl-2,3,4.5-tetrahydro-1H-[1,4]benzodiazepine-3-carboxylate and 3.09 ml (3.09 mmol) of 1N NaOH in 10 ml of tetrahydrofuran was stored at room temperature overnight and the solvent removed under vacuum. The residue was diluted with $H_2O$, extracted with ethyl acetate and the aqueous layer acidified with 2N citric acid. The mixture was extracted with $CH_2Cl$, and the $CH_2Cl_2$ extracts were washed with $H_2O$, brine and dried with $Na_2SO_4$. The solvent was removed to give 0.82 g of a light yellow glass, m.p. 95°–100° C.; Mass spectrum (ES) 481.4 (M+H).

REFERENCE EXAMPLE 186

Methyl 4-(4-Methoxybenzenesulfonyl)-1-(2-methoxyethyl)-2,3,4,5-tetrahydro-1H-[1,4]benzodiazepine-3-carboxylate A mixture of 1.6 g (3.57 mmol) of methyl 1-(methoxyacetyl)-4-(4-methoxybenzenesulfonyl)-2,3,4,5-tetrahydro-1H-[1,4]benzodiazepine-3-carboxylate and 32 ml of borane in tetrahydrofuran (1.0M) was refluxed under nitrogen overnight. Methanol was added and the solvent removed. To the residue was added 25 ml of $CH_2Cl_2$ and 25 ml of 2N HCl and the mixture stirred at room temperature for 1 hour. The organic layer was separated and washed with $H_2O$ and concentrated to dryness. The residue was triturated with ethyl acetate-hexane, cooled and filtered to give 1.2 g of white crystals, m.p. 86°–90° C.; Mass spectrum (ES) 435.4 (M+H). Anal. for $C_{21}H_{26}N_2O_6S$: Calc'd: C,58.1; H,6.0; N,6.5; Found: C.58.5; H,6.0: N,6.5.

REFERENCE EXAMPLE 187

4-(4-Methoxybenzenesulfonyl)-1-(2-methoxyethyl)-2,3,4,5-tetrahydro-1H[1,4]benzodiazepine-3-carboxylic acid A mixture of 1.0 g (2.3 mmol) of methyl 4-(4-methoxybenzenesulfonyl)-1-(2-methoxyethyl)-2,3,4,5-tetrahydro-1H-[1,4]benzodiazepine-3-carboxylate and 3.0 ml of 1N NaOH in 10 ml of tetrahydrofuran was stirred at room temperature for 2 hours and the solvent removed. To the residue was added water and the mixture acidified with 1N HCl. The mixture was extracted with ethyl acetate and the extract was washed with brine and dried with $Na_2SO_4$. The solvent was removed and the residue triturated with ethyl acetate-hexane, cooled and filtered to give 0.65 g of white crystals, m.p. 164°–165° C.,; Mass spectrum (ES) 421.4 (M+H). Anal. for $C_{20}H_{24}N_2O_6S$: Calc'd: C,57.1; H,5.8; N,6.7; Found: C,57.3; H,5.7; N,6.4.

REFERENCE EXAMPLE 188

Methyl 1-(Benzyl)-4-(4-methoxybenzenesulfonyl)-2,3,4,5-tetrahydro-1H-[1,4]benzodiazepine-3-carboxylate A mixture of 0.20 g (0.416 mmol) of methyl 1-(benzoyl)-4-(4-methoxybenzenesulfonyl)-2,3,4,5-tetrahydro-1H-[1,4]benzodiazepine-3 -carboxylate and 4 ml of borane in tetrahydrofuran (1.0M) was refluxed overnight and the solvent removed. To the residue was added 5 ml of $CH_2Cl_2$ and 5 ml of 2N HCl and the mixture stirred for 1 hour. The organic layer was separated and concentrated to dryness. The residue was chromatographed on thick layer silica gel plates with hexane-ethyl acetate (2:1) as solvent to give 0.140 g of a colorless oil, Mass spectrum (ES) 467.5 (M+H).

REFERENCE EXAMPLE 189

4-(4-Methoxybenzenesulfonyl)-1-[4-(trifluoromethoxy)benzoyl]-8-chloro-2,3,4,5-tetrahydro-1H[1,4]benzodiazepine-3-carboxylic acid As described for Reference Example 18, 1.46 g (3.40 mmol) of methyl 2-[(2-amino-4-chlorobenzyl)-(4-methoxybenzenesulfonyl)amino]-3-hydroxypropionate was reacted with 4-(trifluoromethoxy)benzoyl chloride to give 2.59 g of methyl 2-{2-[4-(trifluoromethoxy) benzoyl]amino-4-chlorobenzyl]amino}acrylate as a yellow oil; Mass spectrum (ES) 599.3 (M+H). The preceding compound was stirred with 0.445 g (5.29 mmol) of anhydrous $NaHCO_3$ in 15 ml of methanol at room temperature for 16 hours and then was heated at 80° C. for 2 hours. The solvent was removed and the residue extracted with ethyl acetate. The extract was washed with $H_2O$. brine, and dried ($Na_2SO_4$). The solvent was removed and the residue crystallized from ethyl acetate-hexane to give methyl 4-(4-methoxybenzenesulfonyl)-1-[4-(trifluoromethoxy)benzoyl}-8-chloro-2,3,4,5-tetrahydro-1H-[1,4]benzodiazepine-3-carboxylate as yellow crystals, m.p. 149°–151° C. Anal. for $C_{26}H_{22}ClF_3O_7S$: Calc'd: C,52.1; H,3.7; N,4.7; Cl,6.0; F,9.5; Found: C,51.8; H,3.6; N,4.7; Cl,5.9: F,9.4.

1.58 g (2.64 mmol) of the preceding compound was stirred with 3.43 ml of 1N NaOH in 10 ml of tetrahydrofuran at room temperature for 2 hours and worked up as for Reference Example 104 to give 1.52 g of product. Crystallization from ethyl acetate-hexane gave 1.2 g of white crystals, m.p. 184°–186° C.

REFERENCE EXAMPLE 190

Methyl 4-(4-Methoxybenzenesulfonyl)-1-(4-morpholinoacetyl)-2,3,4,5-tetrahydro-1H[1,4]benzodiazepine-3-carboxylate A mixture of 0.10 g (0.22 mmol) of methyl 1-(chloroacetyl)4-(4-methoxybenzenesulfonyl)-2,3,4,5-tetrahydro-1H-[1,4]benzodiazepine-3-carboxylate, 21.2 µl of morpholine and 125.4 µl of N,N-diisopropylethylamine in 3 ml of $CH_2Cl_2$ was stirred overnight at room temperature. An additional 2.2 µl of morpholine was added and the solution stirred for 2 days at room temperature. The mixture was diluted with $CH_2Cl_2$ and washed with $H_2O$, brine and dried with $Na_2SO_4$. The solvent was removed to give the product as a solid, Mass spectrum (ES) 504.3 (M+H). Anal. for $C_{24}H_{29}N_3O_7S$: Calc'd: C,57.2; H,5.8: N,8.3; Found: C,56.5; H,5.6: N,8.1.

REFERENCE EXAMPLE 191

Methyl 4-(4-Methoxybenzenesulfonyl)-1-[2-(1-pyrazolyl)phenylcarbonyl]-7-methyl-2,3,4,5-tetrahydro-1H-[1,4]benzodiazepine-3-carboxylate As described for the general reaction of ethyl 2-fluorobenzoate with amines set forth in *Tetrahedron*, 53:7557–7576 (1997), ethyl 2-fluorobenzoate was reacted with pyrazole by refluxing N,N-dimethylformamide to give ethyl 2-(1-pyrazolyl)benzoate, as a thick yellow oil. Anal. Calc'd: for $C_{12}H_{12}N_2O_2$: C, 66.7; H, 5.6; N 13.0: Found: C, 66.5: H, 5.4: N, 12.9; Mass spectrum (ES) 217.2 (M+H). A sample (7.02 g) of this compound and 8.42 ml of 5N NaOH in 40 ml of ethanol-tetrahydrofuran (2:1) was refluxed for 2 hrs and the solvent removed. The residue was made acidic (pH6) with 2N citric acid and the precipated solid was filtered to obtain 3.7 g of product. The pH of the filtrate was adjusted to 4.5 and extracted with ethyl acetate. The extract was concentrated to dryness to give 1.5 g of product. The two crops were combined to give 5.2 g of 2-(1-pyrazolyl) benzoic acid, mp 140–142° C. To the preceding compound (2.07 g) in 5 ml $CH_2Cl_2$ (chilled in an ice bath) was added 11.1 ml of a 2 Molar solution of oxalyl chloride in $CH_2Cl_2$ and 0.085 ml of N,N-dimethylformamide. The mixture was allowed to warm to room temperature and stirred for 4 hours. The solvent was removed and 25 ml of toluene added (twice) and removed under vacuum to give 2-(1-pyrazolyl) benzoyl chloride as a yellow solid.

A 2.3 g sample of the preceding compound was reacted with 1.5 g of the compound of Reference Example 179 in 15 ml of $CH_2Cl_2$ and 5.12 ml of triethylamine in the manner described for Reference Example 181 to give methyl 2-[(4-methoxybenzenesulfonyl)-{2-[2-(1-pyrazolyl) phenylcarbonyl]amino-5-methylbenzyl}amino]acrylate. This compound was cyclized with $NaHCO_3$ in methanol in the manner described in Reference Example 181 to give methyl 4-(4-methoxybenzenesulfonyl)-1-[2-(1-pyrazolyl) phenylcarbonyl]-7-methyl-2,3,4,5-tetrahydro-1H-[1,4] benzodiazepine-3-carboxylate (m.p. 240–242° C.).

A 1.16 sample of the preceding compound was hydrolysed with 2.69 ml of 1N NaOH in 10 ml of tetrahydrofuran in the manner described for Reference Example 104 to give 0.71 g of 4-(4-methoxybenzenesulfonyl)-1-[2-(1-pyrazolyl) phenylcarbonyl)-7-methyl-2,3,4,5-tetrahydro-1H[1,4] benzodiazepine-3-carboxylic acid (mp 149–151° C.).

REFERENCE EXAMPLE 192

Methyl 4-(4-Methoxybenzenesulfonyl)-1-[2-(4-morpholino)phenylcarbonyl]-8-chloro-2,3,4,5-tetrahydro-1H-3,4)benzodiazepine-3-carboxylate Ethyl 2-morpholinobenzoate prepared in the manner described in *Tetrahedron*, 53:7557, (1997) was refluxed with 10N NaOH in tetrahydrofuran-ethanol (8:2) for 1.5 hrs to give 2-morpholinobenzoic acid, mp 156–157° C. A 1.8 g, sample of this compound in 5 ml of $CH_2Cl_2$ (chilled) was added to a solution of 7.9 ml of oxalyl chloride in $CH_2Cl_2$ (2M) followed by the addition of 0.058 ml of N,N-dimethylformanide. The solution was stirred at room temperature for 6 hrs and the solvent removed. Toluene was added (2 times) and removed to give 2-(4-morpholino) benzoyl chloride as a yellow solid.

The preceding 2-(4-morpholino)benzoyl chloride was reacted with methyl 2-in the manner described in Reference Examples 181 and 189, and the product was stirred with $NaHCO_3$ in methanol to give methyl 4-(4-methoxybenzenesulfonyl)-1-[2-(4-morpholino)phenylcarbonyl]-8-chloro-2,3,4,5-tetrahydro-1H-[1,4]benzodiazepine-3-carboxylate, as a white solid having a mp 100–105° C.

To 0.90 g of this compound in 10 ml of tetrahydrofuran was added 1.95 ml of 1N NaOH and the solution was stirred at room temperature overnight. Acidification with 2N citric acid gave 0.82 g of 4-(4-methoxybenzenesulfonyl)-1-[2-(4-morpholino)phenylcarbonyl]-8-chloro-2,3,4,5-tetrahydro-1H-[1,4]benzodiazepine-3-carboxylic acid (mp 136–143° C.).

REFERENCE EXAMPLE 193

Methyl 1-(4-Ethoxybenzoyl)-4-(4-methoxybenzenesulfonyl)-2,3,4,5-tetrahydro-1H-[1,4]benzodiazepine-3-carboxylate A mixture of 0.270 g of methyl 4-(4-methoxybenzenesulfonyl)-2,3,4,5-tetrahydro-1H-[1,4]benzodiazepine-3-carboxylate of Reference Example 12, 0.291 g of 4-ethoxybenzoyl chloride and 500 μl of triethylamine in 5 ml of $CH_2Cl_2$ was stirred at room temperature overnight. The mixture was diluted with $CH_2Cl_2$ and $H_2O$ and the $CH_2Cl_2$ layer was separated and concentrated to dryness. The residue was triturated with ethyl acetate to give 0.276 g of methyl 1-(4-ethoxybenzoyl)-4-(4-methoxybenzenesulfonyl)-2,3,4,5tetrahydro-1H-[1,4]benzodiazepine-3-carboxylate as white crystals, (mp 187–190° C.).

A 0.47 g sample of this compound was hydrolyzed with 1.2 ml of 1N NaOH in 4 ml of tetrahydrofuran. Dilution with $H_2O$ and acidification with 1N HCl gave 0.40 g of the acid as a white solid, mp 144–152° C.

REFERENCE EXAMPLE 194

Methyl 4-(4-Methoxybenzenesulfonyl)-1-[2-chloro-4-(3-methyl-1-pyrazolyl)phenylcarbonyl}-2,3,4,5-tetrahydro-1H-[1,4]benzodiazepine-3-carboxylate As described in Example 65, methyl 4-(4-methoxybenzenesulfonyl)-2,3,4,5-tetrahydro-1H-[1,4]benzodiazepine-3-carboxylate was reacted with 4-(3-methyl-1-pyrazolyl)-2-chlorobenzoyl chloride to give methyl 4-(4-methoxybenzenesulfonyl)-1-[2-chloro-4-(3-methyl-1-pyrazolyl)phenylcarbonyl]-2,3,4,5-tetrahydro-1H-[1,4]benzodiazepine-3-carboxylate as a white solid.

Anal. for $C_{29}H_{27}ClN_4O_6S$: Calc'd: C, 58.3; H, 4.6; N, 9.4. Found: C,58.2; H, 4.9; N, 8.9.

This compound was hydrolysed with 1N NaOH in tetrahydrofuran as described in Reference Example 185 to give the benzodiazepine-3-carboxylic acid derivative as a white solid.

REFERENCE EXAMPLE 195

1-Benzyl-4-(4-methoxybenzenesulfonyl)-2,3,4,5-tetrahydro-1H-[1,4]benzodiazepine-3-carboxylic acid A mixture of 1.7 g of the compound of Reference Example 45 and 25 ml of borane in tetrahydrofuran (1.0 Molar) was refluxed under nitrogen overnight. To the solution was added 5 ml of $CH_3OH$, $CH_2Cl_2$ (40 ml) and 30 ml of 2N HCl and the mixture stirred at room temperature for 1.5 hr. The organic layer was separated, washed with brine, dried with $Na_2SO_4$ and the solvent removed. The residue was crystallized from ethanol-hexane to give 1.15 g of methyl 1-benzyl-4-(4-methoxybenzenesulfonyl)-2,3,4,5-tetrahydro-1H-[1,4]benzodiazepine-3-carboxylate as white crystals, mp 120–122° C. A sample (1.0 g) of this compound was hydrolysed with 2.8 ml of 1N NaOH in 7 ml of tetrahydrofuran as described in Reference Example 104 to give 0.64 g of the 2,3,4,5- tetrahydro-1H-[1,4]benzodiazepine-3-carboxylic acid derivative as white crystals (mp 183–185° C.).

REFERENCE EXAMPLE 196

Methyl 1-(2,4-Dimethoxybenzoyl)-4-(4-methoxybenzenesulfonyl)-2,3,4,5-tetrahydro-1H-[1,4]benzodiazepine-3-carboxylate To a cooled (0° C.) solution of 1.0 g (2.66 mmol) of 4-(4-methoxybenzenesulfonyl)-2,3,4,5-tetrahydro-1H-[1,4]benzodiazepine-3-carboxylate from Reference Example 12 and 1.85 ml (13.3 mmol) of triethylarnine in 8 ml of $CH_2Cl_2$ was added 1.17 g (6.65 mmol) of 2,4-dimethoxybenzoyl chloride. The mixture was stirred at room temperature overnight, diluted with $CH_2Cl_2$ and washed with 2N citric acid. The organic layer was washed with $H_2O$, 1N $Na_2CO_3$, brine and dried over $Na_2SO_4$. The solvent was removed and the residue was chromatographed on thick layer silica gel plates with ethyl acetate-hexane (1:1) as an eluent to give 1.0 g of methyl 1-(2,4-dimethoxybenzoyl)-4-(4-methoxybenzenesulfonyl)-2,3,4,5-tetrahydro-1H-[1,4]benzodiazepine-3-carboxylate as a white foam. Anal. for $C_{27}H_{28}H_2O_8S$: Calc'd: C,60.0; H,5.2; N,5.2; Found: C,60.0; H,5.2; N,5.1; Mass Spectrum (ES): 541.0 (M+H).

A 0.80 g (1.48 mmol) sample of the preceding compound and 1.92 ml (1.92 mmol) of 1N NaOH in 5 ml of tetrahydrofuran was stirred at room temperature for 1.5 hours. The solvent was removed and the residue diluted with water. The solution was acidified with 1N HCl, chilled and filtered to give 0.70 g of 1-(2,4-dimethoxybenzoyl)-4-(4-methoxybenzenesulfonyl)-2,3,4,5-tetrahydro-1H-[1,4]benzodiazepine-3-carboxylic acid as a white solid. Anal. for $C_{26}H_{26}N_2O_8S$: Calc'd: C,59.3; H,5.0; N,5.3; Found: C,56.1; H,4.8; N,5.0; Mass Spectrum (ES): 527.0 (M+H).

REFERENCE EXAMPLE 197

Methyl 4-(4-Methoxybenzenesulfonyl)-1-[2-(4-methylpiperazin-1-yl)acetyl]-2,3,4,5-tetrahydro-1H-[1,4]benzodiazepine-3-carboxylate To a mixture of 2.5 g (6.64 mmol) of methyl 4-(4-methoxybenzenesulfonyl)-2,3,4,5-tetrahydro-1H-[1,4]

benzodiazepine-3-carboxylate (Reference Example 12) and 4.63 ml (33.2 mmol) of triethylamine in 40 ml of $CH_9Cl_2$ cooled to 0° C. was added to 1.65 g (14.63 mmol) of chloroacetyl chloride. The solution was stirred at room temperature for 2 days, chilled to 0° C. and 926 μl of triethylamine and 750 mg of chloroacetyl chloride were added thereto. The mixture was stirred at room temperature overnight, diluted with $CH_2Cl_2$ and $H_2O$. The insoluble solid was filtered off. The organic layer of the filtrate was separated, washed with brine, dried with $Na_2SO_4$ and filtered through diatomaceous earth. The solvent was removed and the residue triturated with ethyl acetate and a trace of ethanol. Chilling and filtering gave 0.75 g of methyl 1-(chloroacetyl)-4-(4-methoxybenzenesulfonyl)-2,3,4,5-tetrahydro-1H-[1,4]benzo-diazepine-3-carboxylate (Reference Example 91). Anal. for $C_{20}H_{21}ClN_2O_6S$: Calc'd: C,53.0; H,4.7; N,6.2; Found: C,51.6; H,4.6; N,5.7; Mass Spectrum (ES): 453.0 (M+H).

To a solution of 1.4 g (3.09 mmol) of the preceding compound in 12 ml of $CH_2Cl_2$ cooled to 0° C. was added 1.2 ml (6.79 mmol) of N,N-diisopropylethylamine followed by the addition of 753.2 μl (6.79 mmol) of 1-methylpiperazine. The mixture was stirred at room temperature overnight, diluted with $CH_2Cl_2$, and washed with 2N citric acid, $H_2O$, 1M $NaHCO_3$, brine and dried $(Na_2SO_4)$. The citric acid wash was made basic with saturated $NaHCO_3$ and then extracted with $CH_2Cl_2$. The extract was dried over $Na_2SO_4$ and the solvent removed under vacuum to give 1.10 g of methyl 4-(4-methoxybenzenesulfonyl)-1-[2-(4-methylpiperazin-1-yl)acetyl]-2,3,4,5-tetrahydro-1H-[1,4]benzodiazepine-3-carboxylate as a white glass.

A mixture of 1.0 g (1.94 mmol) of the preceding compound and 2.3 ml (2.3 mmol) of 1N KOH in 5 ml of methanol was stirred at room temperature for 2 hours. The solvent was removed under vacuum. To the residue was added toluene (2 times) and the solvent removed under vacuum after each addition. The solid was dried at 65° C. under vacuum for 6 hours to give 1.1 g of potassium 4-(4-methoxybenzenesulfonyl)-1-[2-(4-methylpiperazin-1-yl)acetyl]-2,3,4,5-tetrahydro-1H-[1,4]benzodiazepine-3-carboxylate as a white solid.

REFERENCE EXAMPLE 198

Methyl 1-Acetyl-4-(4-hydroxybenzenesulfonyl)-2,3,4,5-tetrahydro-1H-[1,4]benzodiazepine-3-carboxylate To a cooled (0°) solution of 2.0 g (4.78 mmol) of methyl 1-acetyl-4-(4-methoxybenzenesulfonyl)-2,3,4,5-tetrahydro-1H-[1,4]benzodiazepine-3-carboxylate in 14 ml of $CH_2Cl_2$ was added dropwise 143.3 ml (14.3 mmol) of a 1.0 molar solution of $BBr_3$ in $CH_2Cl_2$ The mixture was stirred at room temperature for 1.5 hours. Ice and $H_2O$ were added to the reaction mixture and the insolubles filtered off. The filtrate was diluted with $CH_2Cl_2$ and $H_2O$ and the $CH_2Cl_2$ layer separated, washed with brine and dried $(Na_2SO_4)$ The solvent was removed under vacuum to give 1.5 g of a white foam. The solid was chromatographed on silica gel with hexane-ethyl acetate (1:1) as solvent to give a foam which was dried under vacuum to give 0.52 g of product as a white foam; Anal. Calc'd for $C_{19}H_{20}N_2O_6S$: C, 56 4:H, 5.0; N, 6.9 Found: C 55.1; H, 4.7: N, 6.5.

REFERENCE EXAMPLE 199

Methyl 4-(4-Hydroxybenzenesulfonyl)-1-(2-thienylcarbonyl)-2,3,4,5-tetrahydro-1H-[1,4]benzodiazepine-3-carboxylate To a solution of 4.0 g (8.22 mmol) of methyl 4-(4-methoxybenzenesulfonyl)-1-(2-thienylcarbonyl)-2,3,4,5-tetrahydro-1H-[1,4]benzodiazepine-3-carboxylate in 17 ml of $CH_2Cl_2$ chilled to 0° C., was added slowly 16.4 ml (16.44 mmol) of 1.0 molar solution of boron tribromide in $CH_2Cl_2$. The mixture was stirred at room temperature overnight and diluted with $CH_2Cl_2$. The mixture was filtered and the solid washed with $CH_2Cl_2$. and $H_2O$. The filtrate was diluted with $H_2O$ and the organic layer separated. The solvent was removed under vacuum and the solid chromatographed on silica gel with hexane-ethyl acetate (1:1) as solvent to give 0.80 g of off white foam; Mass Spectrum (ES) 473.5 (M+H); Anal. Calc'd for $C_{22}H_{20}N_2O_6S_2$: C, 55.9; H, 4.3; N, 5.9. Found: C, 54.5; H, 4.4; N, 5.5.

REFERENCE EXAMPLE 200

Methyl 1-Benzoyl-4-(4-hydroxybenzenesulfonyl)-2,3,4,5-tetrahydro-1H-[1,4]benzodiazepine-3-carboxylate To a solution of 9.8 g (20.39 mmol) of methyl 1-benzoyl-4-(4-methoxybenzenesulfonyl)-2,3,4,5-tetraydro-1H-[1,4]benzodiazepine in 50 ml of $CH_2Cl_2$ cooled to 0°, was added slowly 40.8 ml (40.8 mmol) of a 1.0 molar solution of $BBr_3$ in $CH_2Cl_2$. The mixture was stirred under nitrogen at room temperature overnight. Ice and $H_2O$ were added and the mixture diluted with $CH_2Cl_2$. The organic layer was separated and the aqueous layer extracted with ethyl acetate. The combined organic extracts ($CH_2Cl_2$+ethyl acetate) were concentrated under vacuum and the residue dissolved in ethyl acetate. The solution was washed with $H_2O$, brine and dried $(Na_2SO_4)$. The solution was filtered through a thin pad of hydrous magnesium silicate and the filtrate concentrated to dryness. The residue was chromatographed on silica gel with hexane-ethyl acetate as solvent to give 8 g of product as an off-white foam; Mass Spectrum (ES) 467 (M+H); Anal Calc'd for $C_{24}H_{22}N_2O_6S$: C, 61.8; H, 4.8; N, 6.0. Found: C, 61.3; H, 4.6; N, 5.8.

Utilizing the method described in Reference Examples 198–200, the following methyl-1-substituted-4-hydroxybenzenesulfonyl)-2,3,4,5-tetrahydro-1H-[1,4]benzodiazepine-3-carboxylates can be prepared.

REFERENCE EXAMPLE 201

Methyl 4-(4-Hydroxybenzenesulfonyl)-1-(4-methylphenylsulfonyl)-2,3,4,5-tetrahydro-1H-[1,4]benzodiazepine-3-carboxylate

REFERENCE EXAMPLE 202

Methyl 1-Methanesulfonyl-4-(4-hydroxybenzenesulfonyl)-2,3,4,5-tetrahydro-1H-[1,4]benzodiazepinef-3-carboxylate 6.0 g (13.2 mmol) of Reference Example 44 and 22.6 ml (22.6 mmol) of $BBr_3$ in $CH_2Cl_2$ (solution) gave, after chromatography on silica with ethyl acetate-hexane (1:1), 0.82 g of a white foam; Mass spectrum (ES) 440.9 (M+H).

REFERENCE EXAMPLE 203

Methyl 4-(4-Hydroxybenzenesulfonyl)-1-(3-pyridinylcarbonyl)-2,3,4,5-tetrahydro-1H-[1,4]benzodiazepine-3-carboxylate

REFERENCE EXAMPLE 204

Methyl 4-(4-Hydroxybenzenesulfonyl)-1-(4-pyridinylcarbonyl-2,3,4,5-tetrahydro-1H-[1,4]benzodiazepine-3-carboxylate

REFERENCE EXAMPLE 205

Methyl 1-(4-Biphenylcarbonl)-4-(4-hydroxybenzenesulfonyl)-2,3,4,5-tetrahydro-1H-[1,4]benzodiazepine-3-carboxylate

REFERENCE EXAMPLE 206

Methyl 4-(4-Hydroxybenzenesulfonyl)-1-(propane-1-sulfonyl)-2,3,4,5-tetrahydro-1H-[1,4]benzodiazepine-3-carboxylate

REFERENCE EXAMPLE 207

Methyl 1-([1,1'-Biphenyl]-2-carbonyl)-4-(4-hydroxybenzenesulfonyl)-2,3,4,5-tetrahydro-1H-[1,4]benzodiazepine-3-carboxylate

REFERENCE EXAMPLE 208

Methyl 1-(3-Fluorobenzoyl)-4-(4-hydroxybenzenesulfonyl)-2,3,4,5-tetrahydro-1H-[1,4]benzodiazepine-3-carboxylate

REFERENCE EXAMPLE 209

Methyl 4-(4-Hydroxybenzenesulfonyl)-1-(2-methyl-5-fluorobenzoyl)-2,3,4,5-tetrahydro-1H-[1,4]benzodiazepine-3-carboxylate

REFERENCE EXAMPLE 210

Methyl 4-(4-Hydroxybenzenesulfonyl)-1-(2-methyl-3-fluorobenzoyl)-2,3,4,5-tetrahydro-1H-[1,4]benzodiazepine-3-carboxylate

REFERENCE EXAMPLE 211

Methyl 4-(4-Hydroxybenzenesulfonyl)-1-(3-phenylpropionyl)-2,3,4,5-tetrahydro-1H-[1,4]benzodiazepine-3-carboxylate

REFERENCE EXAMPLE 212

Methyl 4-(4-Hydroxybenzenesulfonyl)-1-(2-trifluoromethylbenzoyl)-2,3,4,5-tetrahydro-1H-[1,4]benzodiazepine-3-carboxylate

REFERENCE EXAMPLE 213

Methyl 1-(2-Chloro-6-trifluoromethylbenzoyl)-4-(4-hydroxybenzenesulfonyl)-2,3,4,5-tetrahydro-1H-[1,4]benzodiazepine-3-carboxylate

REFERENCE EXAMPLE 214

Methyl 1-(4-Fluoro-2-trifluoromethylbenzoyl)-4-(4-hydroxybenzenesulfonyl)-2,3,4,5-tetrahydro-1H-[1,4]benzodiazepine-3-carboxylate

REFERENCE EXAMPLE 215

Methyl 1-(2-Fluoro-6-trifluoromethybenzoyl)-4-(4-hydroxybenzenesulfonyl)-2,3,4,5-tetrahydro-1H-[1,4]benzodiazepine-3-carboxylate

REFERENCE EXAMPLE 216

Methyl 4-(4-Hydroxybenzenesulfonyl)-1-(2methylbenzoyl)-2,3,4,5-tetrahydro-1H-[1,4]benzodiazepine-3-carboxylate

REFERENCE EXAMPLE 217

Methyl 4-(4-Hydroxybenzenesulfonyl)-1-(2-methyl-6-chlorobenzoyl)-2,3,4,5-tetrahydro-1H-[1,4]benzodiazepine-3-carboxylate

REFERENCE EXAMPLE 218

Methyl 1-(2,4-Dimethylbenzoyl)-4-(4-hydroxybenzenesulfonyl)-2,3,4,5-tetrahydro-1H-[1,4]benzodiazepine-3-carboxylate

REFERENCE EXAMPLE 219

Methyl 1-(2,5-Dimethylbenzoyl)-4-(4-hydroxybenzenesulfonyl)-2,3,4,5-tetrahydro-1H-[1,4]benzodiazepine-3-carboxylate

REFERENCE EXAMPLE 220

Methyl 1-(2-Chloro-4-fluorobenzoyl)-4-(4-hydroxybenzenesulfonyl)-2,3,4,5-tetrahydro-1H-[1,4]benzodiazepine-3-carboxylate

REFERENCE EXAMPLE 221

Methyl 1-(2-Chlorobenzoyl)-4-(4-hydroxybenzenesulfonyl)-2,3,4,5-tetrahydro-1H-[1,4]benzodiazepine-3-carboxylate

REFERENCE EXAMPLE 222

Methyl 1-(2-Fluorobenzoyl)-4-(4-hydroxybenzenesulfonyl)-2,3,4,5-tetrahydro-1H-[1,4]benzodiazepine-3-carboxylate

REFERENCE EXAMPLE 223

Methyl 1-(2-Chloro-6-fluorobenzoyl)-4-(4-hydroxybenzenesulfonyl)-2,3,4,5-tetrahydro-1H-[1,4]benzodiazepine-3-carboxylate

REFERENCE EXAMPLE 224

Methyl 1-(2,3-Difluorobenzoyl)-4-(4-hydroxybenzenesulfonyl)-2,3,4,5-tetrahydro-1H-[1,4]benzodiazepine-3-carboxylate

REFERENCE EXAMPLE 225

Methyl 1-(2,4-Dichlorobenzoyl)-4-(4-hydroxybenzenesulfonyl)-2,3,4,5-tetrahydro-1H-[1,4]benzodiazepine-3-carboxylate

REFERENCE EXAMPLE 226

Methyl 1-(2,3-Dichlorobenzoyl)-4-(4-hydroxybenzenesulfonyl)-2,3,4,5-tetrahydro-1H-[1,4]benzodiazepine-3-carboxylate

REFERENCE EXAMPLE 227

Methyl-1-(2,5-Dichlorobenzoyl)-4-(4-hydroxybenzenesulfonyl)-2,3,4,5-tetrahydro-1H-[1,4]benzodiazepine-3-carboxylate

REFERENCE EXAMPLE 228

Methyl 4-(4-Hydroxybenzenesulfonyl)-1-(2-methylthiobenzoyl)-2,3,4,5-tetrahydro-1H-[1,4]benzodiazepine-3-carboxylate

REFERENCE EXAMPLE 229

Methyl 4-(4-Hydroxybenzenesulfonyl)-1-(3-methyl-2-thienylcarbonyl)-2,3,4,5-tetrahydro-1H-[1,4]benzodiazepine-3-carboxylate

REFERENCE EXAMPLE 230

Methyl 4-(4-Hydroxybenzenesulfonyl)-1-(4-methyl-2-thienylcarbonyl)-2,3,4,5-tetrahydro-1H-[1,4]benzodiazepine-3-carboxylate

REFERENCE EXAMPLE 231

Methyl 1-(3-Chloro-2-thienylcarbonyl)-4-(hydroxybenzenesulfonyl)-2,3,4,5-tetrahydro-1H-[1,4]benzodiazepine-3-carboxylate

REFERENCE EXAMPLE 232

Methyl 1-(2-Furanylcarbonyl)-4-(4-hydroxybenzenesulfonyl)-2,3,4,5-tetrahydro-1H-[1,4]benzodiazepine-3-carboxylate To a solution of 3.0 g (6.38 mmol) of methyl 1-(2-furanylcarbonyl)-4-(4-methoxybenzenesulfonyl)-2,3,4,5-tetrahydro-1H-[1,4]benzodiazepine-3-carboxylate in., 15 ml of $CH_2Cl_2$ (cooled to 0° C.) was added dropwise 12.8 ml (2.8 mmol) of $BBr_3$ in $CH_2Cl_2$ (1.0M in $CH_2Cl_2$). The mixture was stirred at room temperature for 3 days, diluted with $CH_2Cl_2$ and then ice was added. The organic layer was separated, washed with $H_2O$, brine and dried ($Na_2SO_4$). The solvent was removed and the residue chromatographed on silica gel (flash column) with ethyl acetate-hexane (1:1) as solvent. The fractions containing product were combined, the solvent removed and the residue triturated with ethyl acetate. Chilling and filtering gave 0.72 g of methyl 1-(2-furanylcarbonyl)-4-hydroxybenzenesulfonyl)-2,3,4,5-tetrahydro-1H-[1,4]benzodiazepine-3-carboxylate as a white solid, mp 204–206° C.; Anal Cal'd for $C_{22}H_{20}N_2O_7S$: C, 57.9; H, 4.2; N, 6.1. Found: C,57.2; H,4.3; N, 6.0.;Mass spectrum (ES) 457.1 (M+H).

REFERENCE EXAMPLE 233

Methyl 4-(4-Hydroxybenzenesulfonyl)-1-(3-methyl-2-furanylcarbonyl)-2,3,4,5-tetrahydro-1H-[-1,4]benzodiazepine-3-carboxylate

REFERENCE EXAMPLE 234

Methyl 4-(4-Hydroxybenzenesulfonyl)-1-(4-methyl-2-furanylcarbonyl)-2,3,4,5-tetrahydro-1H-[1,4]benzodiazepine-3-carboxylate

REFERENCE EXAMPLE 235

Methyl 1-(5-Chloro-2-furanylcarbonyl)-4-(4-hydroxybenzenesulfonyl)-2,3,4,5-tetrahydro-1H-[1,4]benzodiazepine-3-carboxylate

REFERENCE EXAMPLE 236

Methyl 1-(5-Chloro-2-thienylcarbonyl)-4-(4-hydroxybenzenesulfonyl)-2,3,4,5-tetrahydro-1H-[1,4]benzodeiazepine-3-carboxylate

REFERENCE EXAMPLE 237

Methyl 1-Propionyl-4-(4-hydroxybenzenesulfonyl)-2,3,4,5-tetrahydro-1H-[1,4]benzodeiazepine-3-carboxylate

REFERENCE EXAMPLE 238

Methyl 1-Hexanoyl-4-(4-hydroxybenzenesulfonyl)-2,3,4,5-tetrahydro-1H-[1,4]benzodiazepine-3-carboxylate

REFERENCE EXAMPLE 239

Methyl 4-(4-Hydroxybenzenesulfonyl)-1-(3-thienylcarbonyl)-2,3,4,5-tetrahydro-1H-[1,4]benzodiazepine-3-carboxylate

REFERENCE EXAMPLE 240

Methyl 1-(3-Furanylcarbonyl)-4-(4-hydroxybenzenesulfonyl)-2,3,4,5-tetrahydro-1H-[1,4]benzodiazepine-3-carboxylate

REFERENCE EXAMPLE 241

Methyl 1-(Acetylaminoacetyl)-4-(4-hydroxybenzenesulfonyl)-2,3,4,5-tetrahydro-1H-[1,4]benzodiazepine-3-carboxylate

REFERENCE EXAMPLE 242

Methyl 1-(N,N Dimethylaminoacetyl)-4-(4-hydroxybenzenesulfonyl)-2,3,4,5-tetrahydro-1H-[1,4]benzodiazepine-3-carboxylate

REFERENCE EXAMPLE 243

Methyl 1-(Cyclopropylcarbonyl)-4-(4-hydroxybenzenesulfonyl)-2,3,4,5-tetrahydro-1H-[1,4]benzodiazepine To a solution of 4.44 g (10 mmol) of methyl 1-cyclopropylcarbonyl-4-(4-methoxybenzenefulfonyl)-2,3,4-tetrahydro-1H-[1,4]benzodiaxepine-3-carboxylate in 25 ml of $CH_2Cl_2$ chilled to 0° C. was added dropwise 22 ml (22 mmol) of $BBr_3$ in $CH_2Cl_2$ (1.0 molar solution). The mixture was stirred overnight, cooled and diluted with ice and $H_2O$. Dichloromethane was added and the organic layer separated and washed with $H_2O$, brine and dried ($Na_2SO_4$). The solvent was removed under vacuum to give a solid which was chromatographed on silica gel with the solvent ethyl acetate-hexane (1:1) to give 1.0 g of methyl 1-cyclopropylcarbonyl-4-(4-hydroxybenzenesulfonyl)-2,3,4,5-tetrahydro-1H-[1,4]benzodiazepine-3-carboxylate as a foam; Mass spectrum (ES) 431.3 (M+H).

REFERENCE EXAMPLE 244

Methyl 4-(4-Hydroxybenzenesulfonyl)-1-(trifluoroacetyl)-2,3,4,5-tetrahydro-1H-[1,4]benzodiazepine

EXAMPLE 1

4-(4-Methoxybenzenesulfonyl)-1-(3-trifluoromethylbenzoyl)-2,3,4,5-tetrahydro-1H-[1,4]benzodiazepine-3-carboxylic acid, Hydroxyamide To a solution of 0.297 g (0.556 mmol) of 4-(4-methoxybenzenesulfonyl)-1-(3-trifluoromethylbenzoyl)-2,3,4,5-tetrahydro-1H-[1,4]benzodiazepine-3-carboxylic acid from Reference Example 9 in 5 ml of $CH_2Cl_2$, was added 0.556 ml (1.11 mmol) of 2.0M oxalyl chloride in $CH_2Cl_2$ and 0.044 ml of N,N-dimethylformamide. The mixture was stirred under nitrogen at room temperature for 1.5 hours and cooled in an ice bath. To this solution was added a chilled mixture of 0.156 g (2.24 mmol) of hydroxylamine hydrochloride and 4.68 ml (3.36 mmol) of triethylamine in 1.39 ml of tetrahydrofuran and 0.33 ml of $H_2O$. The mixture was stirred at room temperature overnight and diluted with $CH_2Cl_2$. The mixture was washed with 2N citric acid, $H_2O$, 1N $NaHCO_3$, brine and dried with $Na_2SO_4$. The solvent was removed under vacuum to give 0.29 g of solid. Chromatography on thick layer silica gel plates with ethyl acetate-methanol (9:1) gave 60 mg of solid, m.p. 128–130° C. Anal. for $C_{25}H_{22}F_3N_3O_6S$: Calc'd: C,54.6; H,4.0; N,7.7; Found: C.54.1; H,4.2; N,7.3.

Utilizing the procedure described in Example 1, the following compounds are prepared from the appropriately 1-substituted-4(4-methoxybenzenesulfonyl)-2,3,4,5-tetrahydro-1H-[1,4]benzodiazepine-3-carboxylic acids.

EXAMPLE 2

4-(4-Metboxybenzenesulfonyl)-1-(4-methylphenylsulfonyl)-2,3,4,5-tetrahydro-1H-[1,4]benzodiazepine-3-carboxylic acid, Hydroxyamide Solid. Anal. for $C_{24}H_{25}N_3O_7S_2$: Calc'd: C,54.2; H,4.7; N,7.9: Found: C,53.5; H,5.2; N,7.3.

EXAMPLE 3

1-Methanesulfonyl-4-(4-methoxybenzenesulfonyl)-2,3,4,5-tetrahydro-1H-[1,4]benzodiazepine-3-carboxylic acid, Hydroxyamide Solid. Anal. for $C_{18}H_{21}N_3O_7S_2$: Calc'd: C.47.5; H,4.7; N.9.2; Found: C,46.8; H,4.8: N,8.5.

EXAMPLE 4

1,4-Bis-(4-Methoxybenzenesulfonyl)-2,3,4,5-tetrahydro-1H-[1,4]benzodiazepine-3-carboxylic acid, Hydroxyamide Solid. Anal. for $C_{24}H_{25}N_3O_8S_2$: Calc'd: C,52.6; H,4.6; N,7.7; Found: C,52.2; H,4.8; N,7.3.

EXAMPLE 5

1-Benzoyl-4-(4-methoxybenzenesulfonyl)-2,3,4,5-tetrahydro-1H-[1,4]benzodiazepine-3-carboxylic acid, Hydroxyamide White solid. Anal. for $C_{24}H_{23}N_3O_6S$: Calc'd: C,59.9; H,4.8; N,8.7.; Found: C,59.2; H,4.6; N,8.6; S, 6.4; Mass spectrum (ES) 482.3 (M+H).

EXAMPLE 6

1-Acetyl-4-(4-methoxybenzenesulfonyl)-2,3,4,5-tetrahydro-1H-[1,4]benzodiazepine-3-carboxylic acid, Hydroxyamide White crystals. m.p. 195–197° C. Anal. for $C_{19}H_{21}N_3O_6S$: Calc'd: C,54.4; H,5.1; N,10.0; Found: C,52.6; H,4.9; N,9.4.

EXAMPLE 7

4-(4-Methoxybenzenesulfonyl)-1-(3-pyridinylcarbonyl)-2,3,4,5-tetrahydro-1H-[1,4]benzodiazepine-3-carboxylic acid, Hydroxyamide White crystals, m.p. 167–169° C. Anal. for $C_{23}H_{22}N_4O_6S$: Calc'd: C,57.3; H,4.6; N, 11.6; Found: 55.3; H,4.6; N,10.6.

EXAMPLE 8

4-(4-Methoxybenzenesulfonyl)-1-(2-thienylcarbonyl)-2,3,4,5-tetrahydro-1H-[1,4]benzodiazepine-3-carboxylic acid, Hydroxyamide White solid. Anal. for $C_{22}H_{21}N_3O_6S$): Calc'd: C,54.2; H,4.3; N,8.6; Found: C.53.7; H,4.4; N,8.1.

EXAMPLE 9

1-Methoxyacetyl-4-(4-methoxybenzenesulfonyl)-2,3,4,5-tetrahydro-1H-[1,4]benzodiazepine-3-carboxylic acid, Hydroxyamide White crystals, m.p. 143–145° C. Anal. for $C_{20}H_{23}N_3O_7S$: Calc'd: C,53.4; H,5.2; N,9.4; Found: C,53.9; H,5.6; N,8.5.

EXAMPLE 10

4-(4-Methoxybenzenesulfonyl)-1-(propane-1-sulfonyl)-2,3,4,5-tetrahydro-1H-[1,4]benzodiazepine-3-carboxylic acid, Hydroxyamide Off-white solid. Anal. for $C_{20}H_{25}N_3O_7S_2$: Calc'd: C,49.7; H,5.2; N,8.7; Found: C,48.9; H,5.3; N,8.4.

EXAMPLE 11

4-(4-Methoxybenzenesulfonyl)-1-(2-methyl-5-fluorobenzoyl)-2,3,4,5-tetrahydro-1H-[1,4]benzodiazepine-3-carboxylic acid, Hydroxyamide Off-white solid. Anal. for $C_{25}H_{24}FN_3O_6S$: Calc'd: C,58.5; H.4.7; N,8.2; Found: C,57.1; H,4.8; N.7.6.

EXAMPLE 12

4-(4-Methoxybenzenesulfonyl)-1-(3-phenylpropionyl)-2,3,4,5-tetrahydro-1H-[1,4]benzodiazepine-3-carboxylic acid, Hydroxyamide Solid. Anal. for $C_{26}H_{27}N_3O_6S$: Calc'd: C,61.3; H.5.3; N,8.3; Found: C.59.8; H,5.3; N,7.5.

EXAMPLE 13

4-(4-Methoxybenzenesulfonyl)-1-(4-pyridinylcarbonyl)-2,3,4,5-tetrahydro-1H-[1,4]benzodiazepine-3-carboxylic acid, Hydroxyamide White crystals, m.p. 155–165° C. Anal. for $C_{23}H_{22}N_4O_6S$: Calc'd: C,57.3; H,4.6; N,11.6; Found: C.56.8; H.4.9; N,10.9.

EXAMPLE 14

1-([1,1'-Biphenyl]-2-carbonyl)-4-(4-methoxybenzenesulfonyl)-2,3,4,5-tetrahydro-1H-[1,4]benzodiazepine-3-carboxylic acid, Hydroxyamide Purified by chromatography on silica gel thick layer plates with hexane-ethyl acetate as solvent to give a white solid; m.p. 176–178° C. Anal. for $C_{30}H_{27}N_3O_6S$: Calc'd: C,64.6; H,4.9; N,7.5: Found: C,63.7; H,4.6; N,7.1.

EXAMPLE 15

1-(4-Biphenylcarbonyl)-4-(4-methoxybenzenesulfonyl)-2,3,4,5-tetrahydro-1H-[1,4]benzodiazepine-3-carboxylic acid, Hydroxyamide Purified by chromatography on silica gel thick layer plates with hexane-ethyl acetate (1:1) as solvent to give a white solid, m.p. 160–168° C. Anal. for $C_{30}H_{27}N_3O_6S$: Calc'd: C,64.6; H,4.9; N,7.5; Found: C,61.2. H,4.9; N,7.0; Mass spectrum (ES) 558.1 (M+H).

EXAMPLE 16
1-(3-Fluorobenzoyl)-4-(4-methoxybenzenesulfonyl)-2,3,4,5-tetrahydro-1H-[1,4]benzodiazepine-3-carboxylic acid, Hydroxyamide

EXAMPLE 17
4-(4-Methoxybenzenesulfonyl)-1-(2-methyl-3-fluorobenzoyl)-2,3,4,5-tetrahydro-1H-[1,4]benzodiazepine-3-carboxylic acid, Hydroxyamide

EXAMPLE 18
4-(4-Methoxybenzenesulfonyl)-1-(2-methyl-3-trifluoromethylbenzoyl)-2,3,4,5-tetrahydro-1H-[1,4]benzodiazepine-3-carboxylic acid, Hydroxyamide

EXAMPLE 19
1-(2-Chloro-6-trifluoromethylbenzoyl)-4-(4-methoxybenzenesulfonyl)-2,3,4,5-tetrahydro-1H-[1,4]benzodiazepine-3-carboxylic acid, Hydroxyamide

EXAMPLE 20
1-(4-Fluoro-2-trifluoromethylbenzoyl)-4-(4-methoxybenzenesulfonyl)-2,3,4,5-tetrahydro-1H-[1,4]benzodiazepine-3-carboxylic acid, Hydroxyamide

EXAMPLE 21
1-(2-Fluoro-6-trifluoromethylbenzoyl)-4-(4-methoxybenzenesulfonyl)-2,3,4,5-tetrahydro-1H-[1,4]benzodiazepine-3-carboxylic acid, Hydroxyamide

EXAMPLE 22
4-(4-Methoxybenzenesulfonyl)-1-(2-methylbenzoyl)-2,3,4,5-tetrahydro-1H-[1,4]benzodiazepine-3-carboxylic acid, Hydroxyamide

EXAMPLE 23
4-(4-Methoxybenzenesulfonyl)-1-(2-methyl-6-chlorobenzoyl)-2,3,4,5-tetrahydro-1H-[1,4]benzodiazepine-3-carboxylic acid, Hydroxyamide

EXAMPLE 24
1-(2,4-Dimethylbenzoyl)-4-(4-methoxybenzenesulfonyl)-2,3,4,5-tetrahydro-1H-[1,4]benzodiazepine-3-carboxylic acid, Hydroxyamide

EXAMPLE 25
1-(2,5-Dimethylbenzoyl)-4-(4-methoxybenzenesulfonyl)-2,3,4,5-tetrahydro-1H-[1,4]benzodiazepine-3-carboxylic acid, Hydroxyamide

EXAMPLE 26
1-(2-Chloro-4-fluorobenzoyl)-4-(4-methoxybenzenesulfonyl)-2,3,4,5-tetrahydro-1H-[1,4]benzodiazepine-3-carboxylic acid, Hydroxyamide

EXAMPLE 27
1-(2-Chlorobenzoyl)-4-(4-methoxybenzenesulfonyl)-2,3,4,5-tetrahydro-1H-[1,4]benzodiazepine-3-carboxylic acid, Hydroxyamide

EXAMPLE 28
1-(2-Fluorobenzoyl)-4-(4-methoxybenzenesulfonyl)-2,3,4,5-tetrahydro-1H-[1,4]benzodiazepine-3-carboxylic acid, Hydroxyamide

EXAMPLE 29
1-(2-Chloro-6-fluorobenzoyl)-4-(4-methoxybenzenesulfonyl)-2,3,4,5-tetrahydro-1H-[1,4]benzodiazepine-3-carboxylic acid, Hydroxyamide

EXAMPLE 30
1-(2,3-Difluorobenzoyl)-4-(4-methoxybenzenesulfonyl)-2,3,4,5-tetrahydro-1H-[1,4]benzodiazepine-3-carboxylic acid, Hydroxyamide

EXAMPLE 31
1-(2,4-Dichlorobenzoyl)-4-(4-methoxybenzenesulfonyl)-2,3,4,5-tetrahydro-1H-[1,4]benzodiazepine-3-carboxylic acid, Hydroxyamide
white crystals, m.p. 158–162° C. Anal. for $C_{24}H_{21}Cl_2N_3O_6S$: Calc'd: C,52.4: H.3.9; N,7.6; Found: C,52. 1; H,3.8; N,7.5; Mass spectrum (ES) 549.9 (M+H); 552.0 (M+H).

EXAMPLE 32
1-(2,3-Dichlorobenzoyl)-4-(4-methoxybenzenesulfonyl)-2,3,4,5-tetrahydro-1H-[1,4]benzodiazepine-3-carboxylic acid, Hydroxyamide

EXAMPLE 33
1-(2,5-Dichlorobenzoyl)-4-(4-methoxybenzenesulfonyl)-2,3,4,5-tetrahydro-1H-[1,4]benzodiazepine-3-carboxylic acid, Hydroxyamide

EXAMPLE 34
1-(2-Methoxybenzoyl)-4-(4-methoxybenzenesulfonyl)-2,3,4,5-tetrahydro-1H-[1,4]benzodiazepine-3-carboxylic acid, Hydroxyamide

EXAMPLE 35
1-(4-Chloro-2-methoxybenzoyl)-4-(4-methoxybenzenesulfonyl)-2,3,4,5-tetrahydro-1H-[1,4]benzodiazepine-3-carboxylic acid, hydroxyamide

EXAMPLE 36
4-(4-Methoxybenzenesulfonyl)-1-(2-methylthiobenzoyl)-2,3,4,5-tetrahydro-1H-[1,4]benzodiazepine-3-carboxylic acid, Hydroxyamide

EXAMPLE 37
4-(4-Methoxybenzenesulfonyl)-1-(3-methyl-2-thienylcarbonyl)-2,3,4,5-tetrahydro-1H-[1,4]benzodiazepine-3-carboxylic acid, Hydroxyamide

EXAMPLE 38
4-(4-(Methoxybenzenesulfonyl)-1-(4-methyl-2-thienylcarbonyl)-2,3,4,5-tetrahydro-1H-[1,4]benzodiazepine-3-carboxylic acid, Hydroxyamide

EXAMPLE 39
1-(3-Chloro-2-thienylcarbonyl)-4-(4-methoxybenzenesulfonyl)-2,3,4,5-tetrahydro-1H-[1,4]benzodiazepine-3-carboxylic acid, Hydroxyamide

EXAMPLE 40
1-(2-Furanylcarbonyl)-4-(4-methoxybenzenesulfonyl)-2,3,4,5-tetrahydro-1H-[1,4]benzodiazepine-3-carboxylic acid, Hydroxyamide white solid. Anal. for $C_{22}H_{21}N_3O_7S$: Calc'd: C, 56.0; H, 4.5; N, 8.9; Found: C, 55.6; H, 4.8; N, 8.3; Mass spectrum (ES) 472.0 (M+H).

EXAMPLE 41
4-(4-Methoxybenzenesulfonyl)-1-(3-methyl-2-furanylcarbonyl)-2,3,4,5-tetrahydro-1H-[1,4]benzodiazepine-3-carboxylic acid, Hydroxyamide

EXAMPLE 42
4-(4-Methoxybenzenesulfonyl)-1-(4-methyl-2-furanylcarbonyl)-2,3,4,5-tetrahydro-1H-[1,4]benzodiazepine-3-carboxylic acid, Hydroxyamide

EXAMPLE 43
1(5-Chloro-2-furanylcarbonyl)-4-(4-methoxybenzenesulfonyl)-2,3,4,5-tetrahydro-1H-[1,4]benzodiazepine-3-carboxylic acid, Hydroxyamide

EXAMPLE 44
1-(5-Chloro-2-thienylcarbonyl)-4-(4-methoxybenzenesulfonyl)-2,3,4,5-tetrahydro-1H-[1,4]benzodiazepine-3-carboxylic acid, Hydroxyamide

EXAMPLE 45
1-Propionyl-4-(4-methoxybenzenesulfonyl)-2,3,4,5-tetrahydro-1H-[1,4]benzodiazepine-3-carboxylic acid, Hydroxyamide

EXAMPLE 46
1-Hexanoyl-4-(4-methoxybenzenesulfonyl)-2,3,4,5-tetrahydro-1H-[1,4]benzodiazepine-3-carboxylic acid, Hydroxyamide

EXAMPLE 47
1-(3-Methoxypropionyl)-4-(4-methoxybenzenesulfonyl)-2,3,4,5-tetrahydro-1H-[1,4]benzodiazepine-3-carboxylic acid, Hydroxyamide

EXAMPLE 48
4-(4-Methoxybenzenesulfonyl)-1-(3-thienylcarbonyl)-2,3,4,5-tetrahydro-1H-[1,4]benzodiazepine-3-carboxylic acid, Hydroxyamide

EXAMPLE 49
1-(3-Furanylcarbonyl)-4-(4-methoxybenzenesulfonyl)-2,3,4,5-tetrahydro-1H-[1,4]benzodiazepine-3-carboxylic acid, Hydroxyamide

EXAMPLE 50
1-(trans-Crotonyl)-4-(4-methoxybenzenesulfonyl)-2,3,4,5-tetrahydro-1H-[1,4]benzodiazepine-3-carboxylic acid, Hydroxyamide

EXAMPLE 51
1-(Methacryloyl)-4-(4-methoxybenzenesulfonyl)-2,3,4,5-tetrahydro-1H-[1,4]benzodiazepine-3-carboxylic acid, Hydroxyamide

EXAMPLE 52
1-(Acetylaminoacetyl)-4-(4-methoxybenzenesulfonyl)-2,3,4,5-tetrahydro-1H-[1,4]benzodiazepine-3-carboxylic acid, Hydroxyamide

EXAMPLE 53
1-(Aminoacetyl)-4-(4-methoxybenzenesulfonyl)-2,3,4,5-tetrahydro-1H-[1,4]benzodiazepine-3-carboxylic acid, Hydroxyamide

EXAMPLE 54
1-(N,N-Dimethylaminoacetyl)-4-(4-methoxybenzenesulfonyl)-2,3,4,5-tetrahydro-1H-[1,4]benzodiazepine-3-carboxylic acid, Hydroxyamide

EXAMPLE 55
1-(Cyclopropylcarbonyl)-4-(4-methoxybenzenesulfonyl)-2,3,4,5-tetrahydro-1H-[1,4]benzodiazepine-3-carboxylic acid, Hydroxyamide off-white solid. Anal. for $C_{21}H_{23}N_3O_6S$: Calc'd: C,56.6; H,5.2; N,9.4; Found: C,55.1; H,5.2; N,8.8; Mass spectrum (ES) 446.5 (M+H).

EXAMPLE 56
1-(Cyclobutylcarbonyl)-4-(4-methoxybenzenesulfonyl)-2,3,4,5-tetrahydro-1H-[1,4]benzodiazepine-3-carboxylic acid, Hydroxyamide

EXAMPLE 57
1-(Cyclohexylcarbonyl)-4-(4-methoxybenzenesufonyl)-2,3,4,5-tetrahydro-1H-[1,4]benzodiazepine-3-carboxylic acid, Hydroxyamide off-white solid. Anal. for $C_{24}H_{29}N_3O_6S$: Calc'd: C,59.1; H,6.0; N,8.6; Found: C,58.0; H,6.0; N,8.1; Mass spectrum (ES) 488.6 (M+H).

EXAMPLE 58
4-(4-Methoxybenzenesulfonyl)-1-(phenoxyacetyl)-2,3,4,5-tetrahydro-1H-[1,4]benzodiazepine-3-carboxylic acid, Hydroxamide A mixture of 0.70 g (1.37 mmol) of methyl 4-(4-methoxybenzenesulfonyl)-1-(phenoxyacetyl)-2,3,4-5-tetrahydro-1H[1,4]benzodiazepine-3-carboxylate and 1.8 ml (1.78 mmol) of 1N NaOH in 3 ml of tetrahydrofuran was stirred at room temperature for 2 hours. The mixture was diluted with 3 ml of $H_2O$ and acidified with 1N HCl to give a gummy solid. Ethyl acetate was added thereto and the mixture was chilled overnight. Filtration gave 4-(4-methoxybenzenesulfonyl)-1-(phenoxyacetyl)-2,3,4,5-tetrahydro-1H-[1,4]benzodiazepine-3-carboxylic acid as crystals. m.p. 188°–191° C.

To a 0.496 g (1 mmol) sample of the preceeding compound in 5 ml of $CH_2Cl_2$ cooled to 0° C., was added 1 ml (2 mmol) of oxalyl chloride followed by the addition of 77.4 μl (1 mmol) of N,N-dimethylformamide. The mixture was stirred at room temperature under nitrogen for 1 hour (referred to as solution A). In a separate flask was added 0.278 g (4 mmol) of hydroxyamine hydrochloride, 0.5 ml of $H_2O$ and 836.3 μl (5 mmol) of triethylamine. The mixture was stirred for 20 minutes and then cooled to 0° C. (referred to as solution B). The cooled solution B was added to the cooled (0° C.) and stirred solution A and then this mixture was allowed to warm to room temperature and was stirred overnight. The mixture was concentrated under vacuum, diluted with $CH_2Cl_2$ and washed with $H_2O$, 2N citric acid, 1N $NaHCO_3$, and brine and dried with $Na_2SO_4$. The solvent was removed and the residue crystallized from hexane-ethyl acetate (3:97) to give 0.396 g of white crystals, m.p. 159°–163° C. Anal. for $C_{25}H_{25}N_3O_7S$; Calc'd: C,58.7; H,4.9, N.8.2; Found: C,58.4; H,5. 1; N,7.8; Mass spectrum (ES) 512 (M+H).

EXAMPLE 59
1-Methoxyacetyl-4-(4-methoxybenzenesulfonyl)-7-methyl-2,3-4,5-tetrahydro-1H-[1,4]benzodiazepine-3-carboxylic acid, hydroxyamine A mixture of 1.26 g (2.72 mmol) of methyl 1-metboxyacetyl4-(4-methoxybenzenesulfonyl)-7-methyl-2,3,4,5-tetrahydro-1H-[1,4]benzodiazepine-3-carboxylate from Reference Example 181, 3.53 ml of 1N NaOH and 10 ml of tetrahydrofuran was stirred at room temperature for 3 hours. The solvent was then removed under vacuum and the residue dissolved in $H_2O$ and extracted with ethyl acetate. The aqueous layer was acidified with 1N HCl and then extracted with $CH_2Cl_2$. The $CH_2Cl_2$ layer was dried over $Na_2SO_4$ and the solvent removed to provide a solid. This material was dried in a vacuum oven and given 1.06 of solid, m.p. 101–105° C.

A 1.02 g (2.27 mmol) sample of 1-methoxyacetyl-4-(4-methoxybenzenesulfonyl)-7-methyl-2,3-4,5-tetrahydro-1H-[1,4]benzodiazepine-3-carboxylic acid prepared above was dissolved in 2.57 ml of 1N KOH. Toluene was added several times and the solvent was removed after each addition. The residue was dried in a vacuum oven to give 1.1 g of potassium salt. A mixture of 2.26 ml (4.52 mmol) of oxalyl chloride in 20 ml of $CH_2Cl_2$ was cooled at 0° C. and 0.351 ml (4.52 mmol) of N,N-dimethylformamide (DMF) was added dropwise. The mixture was stirred for 5 minutes and the potassium salt (1.1 g) was added. The mixture was allowed to warm to room temperature and was stirred for 2 hours under nitrogen. The mixture was cooled (0° C.) and this mixture was added to a cooled (0° C.) mixture of 0.628 g (9.04 mmol) of hydroxylamine hydrochloride, 1.89 ml (13.56 mmol) of triethylamine in 1 ml of tetrahydrofuran-water (8:2). The mixture was stirred and chilled at 0° C. for 10 minutes and then stirred at room temperature overnight. The solvent was removed under vacuum and the residue diluted with $CH_2Cl_2$—$H_2O$ and acidified with 2N citric acid (pH 4). The $CH_2Cl_2$ layer was separated and washed with $H_2O$, 1N $NaHCO_3$, $H_2O$, and brine and dried with $Na_2SO_4$. The solution was filtered through a thin pad of hydrous magnesium silicate and the solvent removed under vacuum to give 0.73 g of solid. Crystallization from ethyl acetate gave 0.32 g of crystals, m.p. 146°–148° C.

EXAMPLE 60

1-Benzoyl-4-(4-methoxybenzenesulfonyl)-7-methyl-2,3,4,5-tetrahydro-1H[1,4]benzodianzepine-3-carboxylic acid, Hydroxyamide In the manner described in Example 59, 0.83 g (1.71 mmol) of 1-benzoyl-4-(4-methoxybenzene-sulfonyl)-7-methyl-2,3,4,5-tetrahydro-1H[1,4]benzodianzepine-3-carboxylic acid from Reference Example 185 was converted to the potassium salt with 1.87 ml of 1N KOH and the salt reacted with oxalyl chloride-DMF to give the acid chloride which was reacted with hydroxylamine. The solid from the reaction gave from $CH_2Cl_2$ 0.20 g, of yellow solid, m.p. 137°–139° C.

EXAMPLE 61

4-(4-Methoxybenzenesulfonyl)-1-[4-(trifluoromethoxy)benzoyl]-8-chloro-2,3,4,5-tetrahydro-1H-[1,4]benzodiazepine-3-carboxylic acid, Hydroxyamide In the manner described for Example 59, the potassium salt was prepared from 1.20 g of 4-(4-methoxybenzenesulfonyl)-1-[4-(trifluoromethoxy)benzoyl)-8-chloro-2,3,4.5-tetrahydro-1H-[1,4]benzodiazepine-3-carboxylic acid from Reference Example 189, m.p. 184°–186° C. and reacted with oxalyl chloride-DMF and the acid chloride reacted with hydroxylamine to give 1.20 g of solid. Chromatography on thick layer silica gel plates with ethyl acetate-methanol (95:5) gave 0.58 g of solid m.p. 134° dec; Mass spectrum (ES) 601 (M+H).

EXAMPLE 62

4-(4-Methoxybenzenesulfonyl)-1-(2-methoxyetbyl)-2,3,4,5-tetrahydro-1H-[1,4]benzodiazepine-3-carboxylic acid, Hydroxyamide In the manner described for Example 1, 0.55 g of 4-(4-methoxybenzenesulfonyl)-1-(2-methoxyethyl)-2,3,4,5-tetrahydro-1H-[1,4]-benzodiazepine-3-carboxylic acid from Reference Example 187 was reacted with oxalyl chloride and the resulting acid chloride reacted with hydroxylamine to 0.40 g of solid. Chromatography on thick layer silica gel plates with ethyl acetate-methanol (7:3) gave 0.150 g of product as an off-white foam; Mass spectrum (ES) 434.3 (M-H) Anal. for $C_{20}H_{25}N_3O_6S$: Calc'd: C,55.2; H,5.8; N,9.7; Found: C,54.0; H,5.8; N,9.3.

EXAMPLE 63

4-(4-Methoxybenzenesulfonyl)-1-[2-(1-pyrazolyl)phenylcarbonyl]2,3,4,5-tetrahydro-1H-[1,4]benzodiazepine-3-carboxylic acid, Hydroxyamide As described for the general reaction of ethyl 2-fluorobenzoate with amines set forth in *Tetrahedron*, 53, 7557–7576 (1997), ethyl 2-fluorobenzoate was reacted with pyrazole by refluxing N, N-dimethylformamide to give ethyl 2-(1-pyrazolyl)benzoate, as a thick yellow oil. Anal. Calc'd: for $C_{12}H_{12}N_2O_2$: C, 66.7; H, 5.6; N 13.0: Found: C, 66.5: H, 5.4: N, 12.9; Mass spectrum (ES) 217.2 (M+H). A sample (7.02 g) of this compound and 8.42 ml of 5N NaOH in 40 ml of ethanol-tetrahydrofuran (2:1) was refluxed for 2 hrs and the solvent removed. The residue was made acidic (pH6) with 2N citric acid and the precipated solid was filtered to obtain 3.7g of product. The pH of the filtrate was adjusted to 4:5 and extracted with ethyl acetate The extract was concentrated to dryness to give 1.5 g of product. The two crops were combined to give 5.2 g of 2-(1-pyrazolyl) benzoic acid, mp 140–142° C. To the preceding compound (2.07 g) in 5 ml $CH_2Cl_2$ (chilled in an ice bath )was added 11.1 ml of a 2 Molar solution of oxalyl chloride in $CH_2Cl_2$ and 0.085 ml of N,N-dimethylformamide. The mixture was allowed to warm to room temperature and stirred for 4 hours. The solvent was removed and 25 ml of toluene added (twice) and removed under vacuum to give 2-(1-pyrazolyl) benzoyl chloride as a yellow solid.

A 2.3 g sample of the preceding compound was reacted with 1.5 g of the compound of Reference Example 179 in 15 ml of $CH_2Cl_2$ and 5.12 ml of triethylamine in the manner described for Reference Example 181 to give methyl 2-[(4-methoxybenzenesulfonyl)-{2-[2-(1-pyrazolyl)phenylcarbonyl]amino-5-methylbenzyl}amino]acrylate. This compound was cyclized with $NaHCO_3$ in methanol in the manner described in Reference Example 181 to give methyl 4-(4-methoxybenzenesulfonyl)-1-[2-(1-pyrazolyl)phenylcarbonyl]-7-methyl-2,3,4,5-tetrahydro-1H-[1,4]benzodiazepine-3-carboxylate, m.p. 240–242° C.

A 1.16 g sample of the preceding compound was hydrolysed with 2.69 ml of 1N NaOH in 10 ml of tetrahydrofuran in the manner described for Reference Example 104 to give 0.71 g of 4-(4-methoxybenzenesulfonyl)-1-[2-(1-pyrazolyl)phenylcarbonyl)-7-methyl-2,3,4,5-tetrahydro-1H[1,4]benzodiazepine-3-carboxylic acid, mp 149–151° C.

In the manner described in Example 59, 1.1 g of the preceding compound was converted to the potassium salt and reacted with oxalyl chloride and then hydroxylamine to give the above-identified product as white crystals, mp 194–196° C.

EXAMPLE 64

4-(4-Methoxybenzenesulfonyl)-1-[2-(4-morpholino)phenylcarbonyl}-8-chloro-2,3,4,5-tetrahydro-1H-[1,4]benzodiazepine-3-carboxylic acid, Hydroxyamide Ethyl 2-morpholinobenzoate prepared in the manner described in *Tetrahedron*, 53:7557, (1997) was refluxed with 10N NaOH in tetrahydrofuran-ethanol (8:2) for 1.5 hrs to give 2-morpholinobenzoic acid, mp 156–157° C. A 1.8 g sample of this compound in 5 ml of $CH_2Cl_2$ (chilled) was added a solution of 7.9 ml of oxalyl chloride in $CH_2Cl_2$ (2M) followed by the addition of 0.058 ml of N,N-dimethylformamide. The solution was stirred at room temperature for 6 hrs and the solvent removed. Toluene was added (2 times) and removed to give 2-(4-morpholino) benzoyl chloride as a yellow solid.

In the manner described in Reference Examples 181 and 189, the preceding 2-(4-morpholino)benzoyl chloride was reacted with methyl 2-[(2-amino-4-chlorobenzyl)-(4-methoxybenzenesulfonyl)amino]-3-hydroxypropionate and the product was stirred with $NaHCO_3$ in methanol to give methyl 4-(4-methoxybenzenesulfonyl)-1-[2-(4-morpholino) phenylcarbonyl]-8-chloro-2,3,4,5-tetrahydro-1H-[1,4] benzodiazepine-3-carboxylate, as a white solid having a mp 100–105° C.

To 0.90 g of this compound in 10 ml of tetrahydrofuran was added 1.95 ml of 1N NaOH and the solution was stirred at room temperature overnight. Acidification with 2N citric acid gave 0.82 g of solid, mp 136–143° C. This compound, 4-(4-methoxybenzenesulfonyl)-1-[2-(4-morpholino) phenylcarbonyl]-8-chloro-2,3,4,5-tetrahydro-1H-[1,4] benzodiazepine-3-carboxylic acid (0.78 g) was converted to the potassium salt and reacted first with oxalyl chloride and then with hydroxylamine as described in Example 63 to give 0.276 g of product as a light yellow solid, mp 132° C.

EXAMPLE 65

1-(4-Ethoxybenzoyl)-4-(4-methoxybenzenesulfonyl)-2,3,4,5-tetrahydro-1H-[1, 4]benzodiazepine-3-carboxylic acid, Hydroxyamide A mixture of 0.270 g of methyl 4-(4-methoxybenzenesulfonyl)-2,3,4,5-tetrahydro-1H-[1,4] benzodiazepine-3-carboxylate of Reference Example 12, 0.291 g of 4-ethoxybenzoyl chloride and 500 μl of triethylamine in 5 ml of $CH_2Cl_2$ was stirred at room temperature overnight. The mixture was diluted with $CH_2Cl_2$ and $H_2O$ and the $CH_2Cl_2$ layer was separated and concentrated to dryness. The residue was triturated with ethyl acetate to give 0.276 g of methyl 1-(4-ethoxybenzoyl)-4-(4-methoxybenzenesulfonyl)-2,3,4,5tetrahydro-1H-[1,4] benzodiazepine-3-carboxylate as white crystals, mp 187–190° C.

A 0.47 g sample of this compound was hydrolyzed with 1.2 ml of 1N NaOH in 4 ml of tetrahydrofuran. Dilution with $H_2O$ and acidification with 1N HCl gave 0.40 g of the acid as a white solid, mp 144–152° C. The preceding compound (0.35 g) was converted to the above-titled compound in the manner described in Example 1 to provide 0.195 g of solid, mp 136–142° C.

EXAMPLE 66

4-(4-Methoxybenzenesulfonyl)-1-[2-chloro-4-(3-methyl-1-pyrazolyl)phenylcarbonyl}-2,3,4,5-tetrahydro-1H-[1,4]benzodiazepine-3-carboxylic acid, Hydroxyamide As described in Example 65, methyl 4-(4-methoxybenzenesulfonyl)-2,3,4,5-tetrahydro-1H-[1,4] benzodiazepine-3-carboxylate was reacted with 4-(3-methyl-1-25 pyrazolyl)-2-chlorobenzoyl chloride to give methyl 4-(4-methoxybenzenesulfonyl)-1-[2-chloro-4-(3-methyl-1-pyrazolyl)phenylcarbonyl]-2,3,4,5-tetrahydro-1H-[1,4]benzodiazepine-3-carboxylate as a white solid. Anal. for $C_{29}H_{27}C_1N_4O_6S$: Calc'd: C, 58.3; H, 4.6; N, 9.4. Found: C,58.2; H, 4.9; N, 8.9.

This compound was hydrolysed with 1N NaOH in tetrahydrofuran as described in Reference Example 185 to give the benzodiazepine-3-carboxylic acid derivative as a white solid. This compound was reacted with oxalyl chloride and then reacted with hydroxylamine as described in Example 1 to give the product as white crystals, mp 189–191° C.

EXAMPLE 67

1-Benzyl-4-(4-methoxybenzenesulfonyl)-2,3,4,5-tetrahydro-1H-[1,4]benzodiazepine-3-carboxylic acid, Hydroxylamide A mixture of 1.7 g of the compound of Reference Example 45 and 25 ml of borane in tetrahydrofuran (1.0 Molar) was refluxed under nitrogen overnight. To the solution was added 5 ml of $CH_3OH$, $CH_2Cl_2$ (40 ml) and 30 ml of 2N HCl and the mixture stirred at room temperature for 1.5 hr. The organic layer was separated, washed with brine, dried with $Na_2SO_4$ and the solvent removed. The residue was crystallized from ethanol-hexane to give 1.15 g of methyl 1-benzyl-4-(4-methoxybenzenesulfonyl)-2,3,4,5-tetrahydro-1H-[1,4]benzodiazepine-3-carboxylate as white crystals, mp 120–122° C. A sample (1.0 g) of this compound was hydrolysed with 2.8 ml of 1N NaOH in 7 ml of tetrahydrofuran as described in Reference Example 104 to give 0.64 g of the 2,3,4,5-tetrahydro-1H-[1,4] benzodiazepine-3-carboxylic acid derivative as white crystals, mp 183–185° C.

A 0.55 g sample of this compound was converted to the acid chloride which was reacted with hydroxylamine as described in Example 1 to give the product as a light brown foam; Mass spectrum (ES) 468.1 (M+H).

Utilizing the procedure described in Example 65 above, the following compounds may be prepared.

EXAMPLE 68

4-(4-Methoxybenzenesulfonyl)-1-(4-(2-thienyl) phenyl-carbonyl)-2,3,4,5-tetrahydro-1H-[1,4] benzodiazepine-3-carboxylic acid, Hydroxyamide

EXAMPLE 69

4-(4-Methoxybenzenesulfonyl)-1-(4-(3-thienyl) phenyl-carbonyl)-2,3,4,5-tetrahydro-1H-[1,4] benzodiazepine-3-carboxylic acid, Hydroxyamide

EXAMPLE 70

4-(4-Methoxybenzenesulfonyl)-1-[2-(3-pyrazol) phenyl-carbonyl]-2,3,4,5-tetrahydro-1H-[1,4] benzodiazepine-3-carboxylic acid, Hydroxyamide

EXAMPLE 71

1-(2,4-Dimethoxybenzoyl)-4-(4-methoxybenzenesulfonyl)-2,3,4,5-tetrahydro-1H-[1, 4]benzodiazepine-3-carboxylic acid, Hydroxyamide To a cooled (0° C.) solution of 1.0 g (2.66 mmol) of 4-(4-methoxybenzenesulfonyl)-2,3,4,5-tetrahydro-1H-[1,4] benzodiazepine-3-carboxylate from Reference Example 12 and 1.85 ml (13.3 mmol) of triethylamine in 8 ml of $CH_2Cl_2$ was added 1.17 g, (6.65 mmol) of 2,4-dimethoxybenzoyl chloride. The mixture was stirred at room temperature overnight, diluted with $CH_2Cl_2$ and washed with 2N citric acid. The organic layer was washed with $H_2O$, 1N $Na_2CO_3$, brine and dried over $Na_2SO_4$. The solvent was removed and the residue was chromatographed on thick layer silica gel plates with ethyl acetate-hexane (1:1) as an eluent to give 1.0 g of methyl 1-(2,4-dimethoxybenzoyl)-4-(4-methoxybenzenesulfonyl)-2,3,4,5-tetrahydro-1H-[1,4]benzodiazepine-3-carboxylate as a white foam. Anal. for $C_{27}H_{28}H_2O_8S$: Calc'd: C,60.0; H,5.2; N,5.2; Found: C,60.0; H,5.2; N,5.1; Mass Spectrum (ES): 541.0 (M+H).

A 0.80 g (1.48 mmol) sample of the preceding compound and 1.92 ml (1.92 mmol) of 1N NaOH in 5 ml of tetrahydrofuran was stirred at room temperature for 1.5 hours. The solvent was removed and the residue diluted with water. The solution was acidified with 1N HCl, chilled and filtered to give 0.70 g of 1-(2,4-dimethoxy-benzoyl)-4-(4-methoxybenzenesulfonyl)-2,3,4,5-tetrahydro-1H-[1,4]benzodiazepine-3-carboxylic acid as a white solid. Anal. for $C_{26}H_{26}N_2O_8S$: Calc'd: C,59.3; H,5.0; N,5.3; Found: C,56.1; H,4.8; N,5.0; Mass Spectrum (ES): 527.0 (M+H).

A 0.80 g (1.52 mmol) sample of the preceding compound in 10 ml of $CH_2Cl_2$ (chilled to 0° C.) was added to 1.52 ml (3.04 mmol) of oxalyl cholride (2.0M solution in $CH_2Cl_2$). To the solution was added 118 μl (1.52 mmol) of N,N-dimethylformamide and the solution stirred at 0° C. for 1.5 hours (Mixture A). A mixture of 0.422 g (6.08 mmol) of hydroxylamine hydrochloride, 1.27 ml (9.14 mmol) of triethylamine, 5 ml of N,N-dimethylformamide and 0.5 ml of water was prepared in a separate flask, stirred for 20 minutes at room temperature and then cooled to 0° C. in an ice bath (Mixture B). The cooled solution of Mixture A was added to the cooled Mixture B and then stirred at room temperature overnight. The mixture was diluted with $CH_2Cl_2$ and 2N citric acid added. The organic layer was separated, washed with $H_2O$, brine and dried with $Na_2SO_4$. The solvent was removed and the residue crystalized from ethanol to give 0.40 g of product as white crystals, mp 189–191° C. Anal. for $C_{26}H_{27}N_3O_8S$: Calc'd: C,57.7; H,5.0; N,7.7; Found: C,57.6; H,4.9; N,7.7; Mass Spectrum (ES): 542.2 (M+H).

EXAMPLE 72

4-(4-Methoxybenzenesulfonyl)-1-[2-(4-methylpiperazin-1-yl)acetyl]-2,3,4,5-tetrahydro-1H-[1,4]benzodiazepine-3-carboxylic acid, Hydroxyamide To a mixture of 2.5 g (6.64 mmol) of methyl 4-(4-methoxybenzenesulfonyl)-2,3,4,5-tetrahydro-1H-[1,4]benzodiazepine-3-carboxylate (Reference Example 12) and 4.63 ml (33.2 mmol) of triethylamine in 40 ml of $CH_2Cl_2$ cooled to 0° C. was added to 1.65 g (14.63 mmol) of chloroacetyl chloride. The solution was stirred at room temperature for 2 days, chilled to 0° C. and 926 μl of triethylamine and 750 mg of chloroacetyl chloride were added thereto. The mixture was stirred at room temperature overnight, diluted with $CH_2Cl_2$ and $H_2O$. The insoluble solid was filtered off. The organic layer of the filtrate was separated , washed with brine, dried with $Na_2SO_4$ and filtered through diatomaceous earth. The solvent was removed and the residue triturated with ethyl acetate and a trace of ethanol. Chilling and filtering gave 0.75 g of methyl 1-(chloroacetyl)-4-(4-methoxybenzenesulfonyl)-2,3,4,5-tetrahydro-1H-[1,4]benzo-diazepine-3-carboxylate (Reference Example 91). Anal. for $C_2OH_{21}$ $ClN_2O_6S$: Calc'd: C,53.0; H,4.7; N,6.2; Found: C,51.6; H,4.6; N,5.7; Mass Spectrum (ES): 453.0 (M+H).

To a solution of 1.4 g (3.09 mmol) of the preceding compound in 12 ml of $CH_2Cl_2$ cooled to 0° C. was added 1.2 ml (6.79 mmol) of N,N-diisopropylethylamine followed by the addition of 753.2 μl (6.79 mmol) of 1-methylpiperazine. The mixture was stirred at room temperature overnight, diluted with $CH_2Cl_2$, and washed with 2N citric acid, $H_2O$, 1M $NaHCO_3$, brine and dried ($Na_2SO_4$). The citric acid wash was made basic with saturated $NaHCO_3$ and then extracted with $CH_2Cl_2$. The extract was dried over $Na_2SO_4$ and the solvent removed under vacuum to give 1.10 g of methyl 4-(4-methoxybenzenesulfonyl)-1-[2-(4-methylpiperazin-1-yl)acetyl]-2,3,4,5-tetrahydro-1H-[1,4]benzodiazepine-3-carboxylate as a white glass.

A mixture of 1.0 g (1.94 mmol) of the preceding compound and 2.3 ml (2.3 mmol) of 1N KOH in 5 ml of methanol was stirred at room temperature for 2 hours. The solvent was removed under vacuum. To the residue was added toluene (2 times) and the solvent removed under vacuum after each addition. The solid was dried at 65° C. under vacuum for 6 hours to give 1.1 g of potassium 4-(4-methoxybenzenesulfonyl)-1-[2-(4-methylpiperazin-1-yl)acetyl]-2,3,4,5-tetrahydro-1H-[1,4]benzodiazepine-3-carboxylate as a white solid.

To 1.85 ml (3.69 mmol) of a 2.0 molar solution of oxalyl chloride in $CH_2Cl_2$, cooled to 0C, was added slowly 286 μl (3.69 mmol) of N,N-dimethylformamide (precipitate formed). To this stirred mixture was 1.0 g (1.85 mmol) of the preceding compound in 5 ml of $CH_2Cl_2$. The mixture was stirred under nitrogen for two hours (Mixture A).

In a separate flask, a mixture of 0.514 g (7.4 mmol) of hydroxylamine hydrochloride, 1.55 ml (11.1 mmol) of triethylamine in tetrahydrofuran-water (4:1) was stirred at room temperature and then cooled to 0° C. and stirred for 5 minutes. To this mixture was added the cooled (0° C.) Mixture A and then the resulting solution stirred at room temperature overnight. The mixture was concentrated under vacuum and $CH_2Cl_2$ added. The organic layer was separated and concentrated to dryness to give 1.4 g of product. The product was chromatographed on thick layer silica gel plates with $CH_2Cl_2$—$CH_3OH$—$NH_4OH$(45:6:1) as a solvent to give 65 mg of brown solid:

Mass Spectrum (ES): 518.3 (M+H).

EXAMPLE 73

4-[4-(4-Chlorophenyloxy)benzenesulfonyl]-1-(methoxyacetyl)-2,3,4,5-tetrahydro-1H-[1,4]benzodiazepine-3-carboxylic acid, Hydroxyamide A. N-[4-(4-Chlorophenyloxybenzenesulfonyl)serine methyl ester (methyl-3-hydroxy-2-[4-(4-chlorophenoxy)benzenesulonylamino]propionate). To a mixture of 3.42 g (22 mmol) of serine, methyl ester, hydrochloride and 10.7 ml (77.0 mmol) of triethylamine in 60 ml of $CH_2Cl_2$, chilled to 0° C., was added 6.063 g (20 mmol) of 4-(4-chlorophenyloxy)benzenesulfonyl chloride. The mixture was stirred at room temperature overnight, diluted with $CH_2Cl_2$ and washed with 2N citric acid, $H_2O$, 1N $NaHCO_3$, brine and dried with $Na_2SO_4$. The solvent was removed to give an oil which was dried under vacuum at 68° C. to give a solid. Trituration with hexane-ethyl acetate gave 5.85 g of off-white crystals, mp 90–94° C. Anal. for $C_{16}H_{16}ClNO_6S$: Calc'd: C,49.8; H,4.2; N,3.6; Found: C,50.1; H,4.1; N,3.8; Mass Spectrum (ES): 385.9 (M+H).

B. Methyl 3-hydroxy-2-{[4-(4-chlorophenyloxy)benzene-sulfonyl]-(2-nitrobenzyl)amino}proprionate. To a cooled (0° C.) solution of 5.5 g (14.76 mmol) of compound from part A in 60 ml of dry N,N-dimethylformamide was added (portionwise), 0.682 g (17 mmol) of sodium hydride (60% in oil). After gas evolution ceased, 3.7 g (17 mmol) of 2-nitrobenzylbromide in 15 ml of N,N-dimethylformamide was added slowly. The mixture was stirred at room temperature overnight and diluted with 200 ml of ethyl acetate and 150 ml of water. The organic layer was separated and washed with $H_2O$, brine and dried with $Na_2SO_4$. The solvent was removed under vacuum and the residue chromatographed on a silica gel column with hexane-ethyl acetate (2:1) as an eluent to give 4.7 g of a brown oil. Anal. for $C_{23}H_{21}ClN_2O_8S$: Calc'd: C,53.0; H,4.1; N,5.4; Found: C,53.2; H,4.2; N,5.1; Mass Spectrum (ES): 521.2 (M+H).

C. Methyl 2-{(2-aminobenzyl)-[4-(4-chlorophenyloxy)benzene-sulfonyl]amino}-3-hydroxypropionate. A mixture of 3.0 g (5.77 mmol) of the compound from part B and 0.300 g of 10% wet palladium on carbon (50% in $H_2O$) in 300 ml of ethyl acetate-ethanol (1:1) was shaken in a Parr hydrogenator under 35 psi of hydrogen for 4 hours. The mixture was filtered through diatomaceous earth and the solvent removed under vacuum. The residue was dried at 65° C. under vacuum to give 2.63 g of an off-white solid. Anal. for $C_{23}H_{23}ClN_2O_6S$: Calc'd: C,56.3; H,4.7; N,5.7; Found: C,56.6; H,4.6; N,5.6; Mass Spectrum (ES): 491.1 (M+H).

D. Methyl 2-{[4-(4-chlorophenyloxy)benzenesulfonyl]-[2-(methoxyacetylamino)benzyl]amino}acrylate. To a mixture of 0.80 g (1.63 mmol) of the compound from Part C and 1.14 ml (8.15 mmol) of triethylaniine in 8 ml of $CH_2Cl_2$, cooled to 0° C., was added 328 µl (3.58 mmol) of methoxyacetyl chloride. The mixture was stirred at room temperature overnight, diluted with $CH_2Cl_2$ and washed with $H_2O$, 2N citric acid, brine and dried ($Na_2SO_4$). The solvent was removed under vacuum and the residue chromatographed on thick layer silica gel plates with hexane-ethylacetate (2: 1) as a solvent to give 0.48 g of a white foam. Anal. for $C_{26}H_{25}ClN_2O_7S$: Calc'd: C,57.3; H,4.6; N,5.1; Found: C,56.7; H,4.7; N,5.0; Mass Spectrum (ES): 545.2 (M+H).

E. Methyl 4-[4-(4-chlorophenyloxy)benzenesulfonyl]-1-(methoxyacetyl)-2,3,4,5-tetrahydro-1H-[1.4]benzodiazepine-3-carboxylate. A mixture of 0.45 g (0.827 mmol) of the compound from part D and 0.09 g of anhydrous $NaHCO_3$ in 5 ml of dry methanol was stirred at room temperature overnight. The solvent was removed, ethyl acetate added and the mixture washed with $H_2O$, brine and dried with $Na_2SO_4$. The solvent was removed to give 0.43 g of an off-white solid. Anal. for $C_{26}H_{25}ClN_2O_7S$: Calc'd: C,57.3; H,4.6; N,5.1; Found: C,57.6; H,4.6; N,5.0; Mass Spectrum (ES): 545.2 (M+H).

F. 4-[(4-Chlorophenyloxybenzenesulfonyl]-1-(methoxyacetyl)-2,3,4,5-tetrahydro-1H-[1,4]benzodiazepine-3-carboxylic acid. A mixture of 0.52 g (0.956 mmol) of the compound from Part F and 1.2 ml (1.2 mmol) of 1N KOH in 8 ml of methanol was stirred at room temperature for 2 hours. An additional 0.6 ml of 1N KOH was added and the mixture was stirred at room temperature overnight. The mixture was concentrated, diluted with $H_2O$ and extracted with ethyl acetate. The extract was washed with brine and dried over $Na_2SO_4$. The solvent was removed and the product dried at 65° C. under vacuum to give 0.49 g of off-white foam. Anal. for $C_{25}H_{23}ClN_2O_7S$: Calc'd: C,56.6; H,4.4; N,5.3; Found: C,56.6; H,4.3; N,5.0; Mass Spectrum (ES): 531.2 (M+H).

To a solution of 0.45 g (0.848 mmol) of the compound from Part F in 4 ml of $CH_2Cl_2$ cooled to 0° C. was added 850 µl (1.69 mmol) of oxalyl chloride (2.0 molar solution in $CH_2Cl_2$) and then 50.2 µl (0.848 mmol) of N,N-dimethylflormamide. This mixture was stirred under nitrogen for 2 hours (Solution A). In a separate flask a mixture of 2.12 g (5.0 mmol) of hydroxylamine hydrochloride, 1.07 ml (7.65 mmol) of triethyl amine, 4 ml of tetrahydroforan and 0.4 ml of $H_2O$ was stirred for 15 minutes and cooled to 0° C. To this mixture was added the cooled (0° C.) Solution A and the mixture was stirred at room temperature overnight. The mixture was concentrated under vacuum, diluted with ethyl acetate and washed with $H_2O$, 1N $NaHCO_3$ 2N citric acid, brine and dried over $Na_2SO_4$. The solvent was removed under vacuum and the residue chromatographed on thick layer silica gel plates with 2% methanol in ethyl acetate to give 0.20 g of the product of the Example as a brown solid. Anal. for $C_{25}H_{24}ClN_3O_7S$: Calc'd: C,55.0; H,4.4; N,7.7; Found: C,53.1; H,5.0; N,6.7; Mass Spectrum (ES): 546.3 (M+H).

EXAMPLE 74

4-[4-(4-Chlorophenyloxy)benzenesulfonyl]-1-(2-thienylcarbonyl)-2,3,4,5-tetrahydro-1H[1,4]benzodiazepine-3-carboxylic acid, Hydroxyamide The following reactions were carried out in the manner described for Example 73, Parts D, E, and F. A 1.4 g (2.85 mmol) sample of methyl 2-{(2-aminobenzyl)-[4-(4-chlorophenyloxy)benzenesulfonyl]amino}-3-hydroxypropionate (the compound of Part C of Example 73) was reacted with 1.25 g (8.55 mmol) of 2-thiophenecarbonyl chloride to give 1.7 g of methyl 2-{[4-(4-chlorophenyloxy)benzenesulfonyl]-[2-(2-thienylcarbonyl-amino)benzyl]amino}acrylate as a yellow oil. Mass Spectrum (ES): 583.1 (M+H).

The reaction of 1.5 g of the preceding compound with 0.251 g of $NaHCO_3$ in 8 ml methanol gave 1.6 g of methyl 4-[4-(4-chlorophenyloxy)benzenesulfonyl)-1-(2-thienylcarbonyl)-2,3,4,5-tetrahydro-1H-[1,4]benzodiazepine-3-carboxylate as a yellow oil. Mass Spectrum (ES): 583.1 (M+H).

The hydrolysis of 1.5 g of the preceding compound with 3.3 ml of 1N NaOH in 6 ml of tetrahydroforan gave 1.2 g of 4-[4-(4-chlorophenyloxy)benzenesulfonyl]-1-(2-thienylcarbonyl)-2,3,4,5-tetrahydro-1H-[1,4]benzodiazepine-3-carboxylic acid as an off-white foam. As described for Example 73, 1.0 g of the preceding benzodiazepine-3-carboxylic acid was reacted with oxalyl chloride and then with hydroxylamine to give the product of the Example as a solid (off-white foam). Mass Spectrum (ES): 584.2 (M+H).

EXAMPLE 75

4-[4-(4-Chlorophenyloxy)benzenesulfonyl]-1-(benzoyl)-2,3,4,5-tetrahydro-1H[1,4]benzodiazepine-3-carboxylic acid, Hydroxyamide The following reactions were carried out in the manner described for Example 73, Parts D, E, and F. A 1.0 g (2.04 mmol) sample compound C of Example 73 was reacted with 710 µl (6.10 mmol) of benzoyl chloride to give 1.25 g of methyl 2-{[4-(4-chlorophenyloxy)benzenesulfonyl]-[2-(benzoylamino)benzyl]amino}acrylate as a brown oil. Mass Spectrum (ES): 577.2 (M+H).

The reaction of 1.1 g (1.9 mmol) of the preceding compound with 0.208 g (2.48 mmol) of $NaHCO_3$ in 8 ml of methanol gave 1.1 g of methyl 4-[4-(4-chlorophenyloxy)benzenesulfonyl]-1-(benzoyl)-2,3,4,5-tetrahydro-1H-[1,4]

benzodiazepine-3-carboxylate as a brown oil. Mass Spectrum (ES): 577.1 (M+H).

A 1.0 g (1.73 mmol) sample of the preceding compound was hydrolysed with 2.3 ml (2.75 mmol) of 1N NaOH in 5 ml of tetrahydrofuran to give 0.50 g of 4-[4-(4-chlorophenyloxy)benzenesulfonyl]-1-(benzoyl)-2,3,4,5-tetrahydro-1H-[1,4]benzodiazepine-3-carboxylic acid as a white foam. As described for Example 73, 0.460 g (0.817 mmol) of the preceding benzodiazepine-3-carboxylic acid was reacted with oxalyl chloride and then with hydroxylamine to give 0.04 g of the product of the Example as a light brown solid. Mass Spectrum (ES): 578.2 (M+H).

EXAMPLE 76

4-[4-(4-Pyridinyloxy)benzenesulfonyl]-1-(methoxyacetyl)-2,3,4,5-tetrahydro-1H[1,4]benzodiazepine-3-carboxylic acid, Hydroxyamide A. To a cooled mixture of 6.84 g (44 mmol) of D, L-serine, methyl ester hydrochloride and 21.4 (144 mmol) of triethylamine in 90 ml of $CH_2Cl_2$ was added a solution of 10.78 g (40 mmol) of 4-(4-pyridinyloxy)benzenesulfonyl chloride in 50 ml of $CH_2Cl_2$. The mixture was stirred at room temperature overnight, diluted with 50 ml of $CH_2Cl_2$ and the solution washed with $H_2O$, 1N $NaHCO_3$, 2N citric acid, brine and dried (with $Na_2SO_4$). The solvent was removed under vacuum to give a solid. The aqueous 2N citric acid wash was made basic with saturated $NaHCO_3$ and then extracted with $CH_2Cl_2$. The solvent was removed to give a solid. The two crops of solid were combined, washed with $H_2O$ and then hexane. The solid was dried at 80° C. to give 10.95 g of methyl 3-hydroxy-2-[4-(4-pyridinyloxy)-benzenesulfonylamino]propionate as white crystals, mp. 137–139° C.

B. To a solution of 4.5 g (12,.78 mmol) of the product from Part A in 35 ml of dry N,N-dimethylformanide cooled to 0° C. was added (portionwise) 0.662 g (16.61 mmol) of $NaHCO_3$ (60% in oil). The mixture was stirred 15 minutes and 3.59 g (16.61 mmol) of 2-nitrobenzylbromide in 15 ml of N,N-dimethylformamide was added hereto. The mixture was stirred at room temperature overnight, diluted with ethyl acetate (200 ml) and $H_2O$ (100 ml). The organic layer was separated and washed with $H_2O$, brine and dried (with $Na_2SO_4$). The solvent was removed to give 5.9 g of solid. Column chromatography on silica gel with ethyl acetate-hexane (10:1) as an eluant gave 1.4 g of methyl 2-{(2-nitrobenzyl)-[4-(4-pyridinyloxy) benzenesulfonyl]amino}-3-hydroxypropionate as an off-white solid. Mass Spectrum (ES): 488.1 (M+H).

The compound from Part B was converted to the product of the Example in the manner described for Example 73 in Parts D, E, and F.

EXAMPLE 77

1-(Benzoyl)-4-(4-pentyloxybenzenesulfonyl)-2,3,4,5-tetrahydro-1H-[1,4]-benzodiazepine-3-carboxylic Acid, Hydroxyamide To a stirred solution of 1.24 g (4.82 mmol) of triphenylphosphine in 12 ml of toluene and 3 ml of N,N-dimethylformamide was added 524 μL (4.82 mmol) of 1-pentanol and 1.5 g (3.22 mmol) of methyl 1-(benzoyl)-4-(4-hydroxybenzenesulfonyl)-2,3,4,5-tetrahydro-1H-[1,4]benzodiazepine-3-carboxylate. To this stirred mixture was added 259 μl (4.82 mmol) of diethyl azodicarboxylate and the mixture was stirred overnight. The solvent was removed and the residue chromatographed on silica gel with ethyl acetate-hexane (1:3) as solvent. Concentration of the fractions containing product gave 1.59 g of a white solid; mp 170–172° C; Anal. Calcd for $C_{29}H_{32}N_2O_6$: C, 64.9; H, 6.0; N, 5.2. Found: C, 64.7; H, 6.0; H, 5.4.

A mixture of a 1.4 g (2.61 mmol) sample of the preceding compound and 3.4 ml (3.4 mmol) of 1N KOH in 7 ml of tetrahydrofuran was stirred at room temperature for 2 hrs and the solvent removed under vacuum. To the residue was added toluene and the solvent removed (repeated two times). The residue was dried at 85° C. under vacuum overnight to give 1.5 g of 1-(benzoyl)-4-(4-pentyloxybenzenesulfonyl)-2,3,4,5- tetrahydro-1H-[1,4]benzodiazepine-3-carboxylic acid as the potassium salt. To 10 ml of $CH_2Cl_2$ was added 4.8 ml (9.6 mmol) of oxalyl chloride in $CH_2Cl_2$ (2.0 molar) and the solution chilled to 0° C. To the chilled solution was added 740 μL (9.56 mmol) of N,N-dimethylformamide and 1.34 g (2.39 mmol) of the preceding potassuim salt in 5 ml of dry N,N-dimethylformamide. The mixture was stirred at room temperature for 1.5 hr, cooled to 0° C., and added to a chilled (0° C.) solution of 2.2 ml (35.9 mmol) of 50% aqueous hydroxylamine in 10 ml of tetrahydrofuran. The mixture was stirred at room temperature overnight and diluted with $CH_2Cl_2$. The $CH_2Cl_2$ layer was separated, washed with $H_2O$ and concentrated to dryness under vacuum. The residue was chromatographed on silica gel with ethyl acetate-hexane (1:1) as solvent. Fraction containing product was concentrated to dryness and the residue dissolved in ethyl acetate. The solution was washed with three times with $H_2O$ and once with brine and dried ($Na_2SO_4$). The solvent was removed and the residue dried at 85° C. under vacuum overnight to give 0.96 g of product as a white foam; Mass spectrum (ES) 538.0 (M+H).

EXAMPLE 78

1-Acetyl-4-(4-Hydroxybenzenesulfonyl)-2,3,4,5-tetrahydro-1H-[1,4]benzodiazepine-3-carboxylic acid, Hydroxyamide To a crude mixture of 1-acetyl-4-(4-hydroxybenzenesulfonyl)-2,3,4,5-tetrahydro-1H-[1,4] benzodiazepine-3-carboxylic acid (0.55 g) and N-hydroxybenzotriazole (0.414 g) in 5 ml of N,N-dimethylformamide was added 0.684 g of 1-[3-(dimethylamino)propyl]-3-ethylcarbodiimide hydrochloride. The mixture was stirred at room temperature for 1 hr and then 750 μL of hydroxylamine in water (50%) was added and the mixture stirred at room temperature overnight. The mixture was diluted with ethyl acetate and then washed with $H_2O$, 2N citric acid, brine and dried ($Na_2SO_4$). The solvent was removed under vacuum to give a solid. Chromatography on silica gel with 10% methanol in ethyl acetate as solvent gave a solid which was dried at 78° C under vacuum overnight to give an off-white foam; Mass spectrum (ES) 406.1 (M+H); Anal. Calcd. For $C_{18}H_{19}N_3O_6S$; C, 53.3; H, 4.7; N, 10.4. Found: C, 52.6; H, 5.2; N, 10.4.

The present invention may be embodied in other specific forms without departing from the spirit or essential attributes thereof and, accordingly, reference should be made to the appended claims, rather than to the foregoing specification, as indicating the scope of the invention.

What is claimed is:
1. A compound of Formula 1:

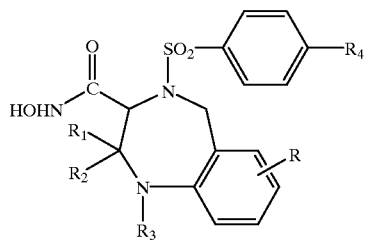

wherein

R is selected from hydrogen, $(C_1-C_3)$alkyl, —CN, —OR', —SR', —CF$_3$, —OCF$_3$, Cl, F, NH$_2$, NH$(C_1-C_3)$alkyl, —N(R')CO$(C_1-C_3)$alkyl, —N(R')(R'), NO$_2$, —CONH$_2$, —SO$_2$NH$_2$, —SO$_2$N(R')(R'), —N(R')COCH$_2$O—$(C_1-C_3)$alkyl, wherein R' is $(C_1-C_3)$ alkyl or hydrogen;

R$_4$ is hydroxy, $(C_1-C_6)$ alkyl—O—, $(C_1-C_6)$ alkyl—S—,

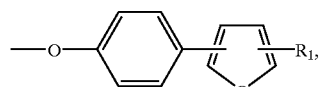

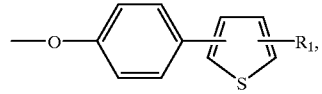

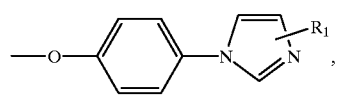

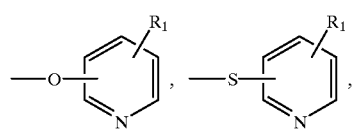

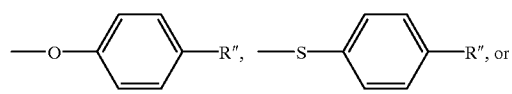

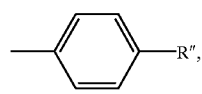

wherein R is hydrogen, halogen, cyano, methyl or —OCH$_3$;

R$_1$ and R$_2$ are each, independently, hydrogen or CH$_3$;

R$_3$ is $(C_1-C_8)$alkyl, NH$_2$CH$_2$CO—, $(C_1-C_6)$ alkylNHCH$_2$CO—, HO(CH$_2$)$_m$CO—, HCO—. Aryl (CH$_2$)$_n$CO—, Heteroaryl(CH$_2$)$_n$CO—, $(C_1-C_3)$alkyl—O—(CH$_2$)$_n$CO—, $(C_1-C_3)$alkylCO—, $(C_1-C_3)$alkylCO—NHCH$_2$CO—, $(C_3-C_7)$cycloalkylCO—, $(C_1-C_3)$alkylSO$_2$—, Aryl(CH$_2$)$_n$SO$_2$—, Heteroaryl (CH$_2$)$_n$SO$_2$—, $(C_1-C_3)$alkyl—O—(CH$_2$)$_m$—SO$_2$—, $(C_1-C_3)$alkyl—O—(CH$_2$)$_m$, $(C_1-C_3)$alkyl—O—$(C_1-C_3)$alkyl, HO—$(C_1-C_3)$alkyl—O—$(C_1-C_3)$alkyl, Aryl—O—CH$_2$CO—, Heteroaryl—O—CH$_2$CO—, ArylCH=CHCO—, HeteroarylCH=CHCO—, $(C_1-C_3)$alkylCH=CHCO—,

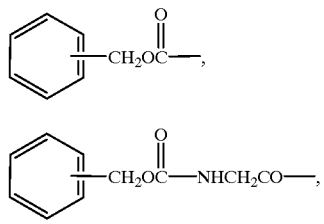

Aryl$(C_1-C_3)$alkyl, Heteroaryl$(C_1-C_3)$alkyl, ArylCH=CHCH$_2$—, HeteroarylCH=CHCH$_2$—, $(C_1-C_6)$alkylCH=CHCH$_2$—,

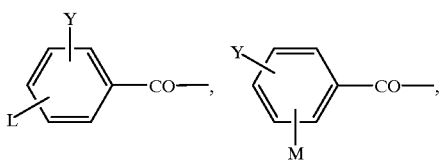

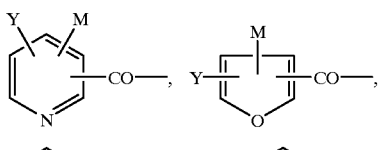

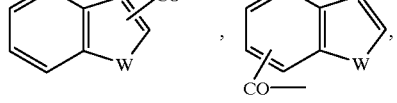

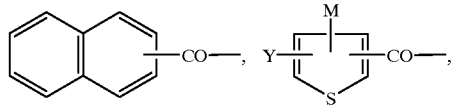

R'OCH$_2$ CH(OR')CO—, (R'OCH$_2$)$_2$C(R')CO—,

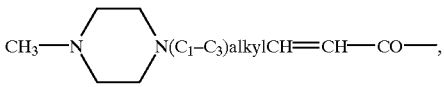

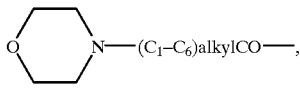

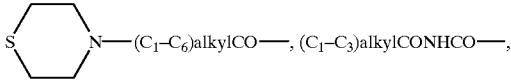

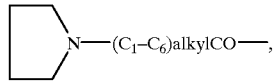

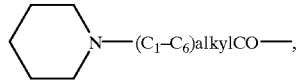

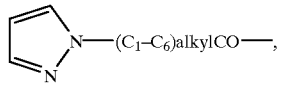

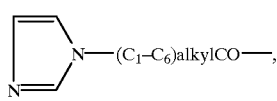

-continued

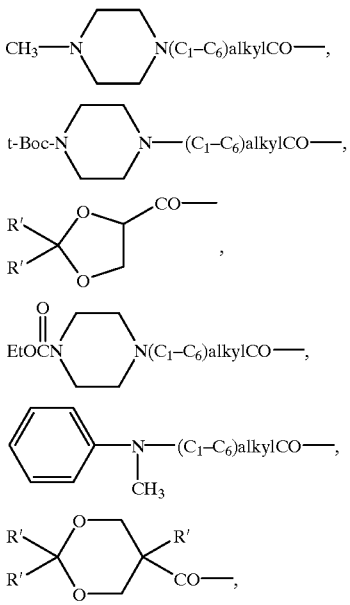

[(C$_1$–C$_6$)alkyl]$_2$—N—(C$_1$–C$_6$)alkyl CO—, or (C$_1$–C$_6$)alkyl—NH—(C$_1$–C$_6$)alkylCO—;
wherein
m=1 to 3; n 0 to 3;
Aryl is

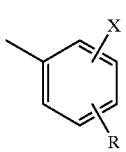

and
Heteroaryl is

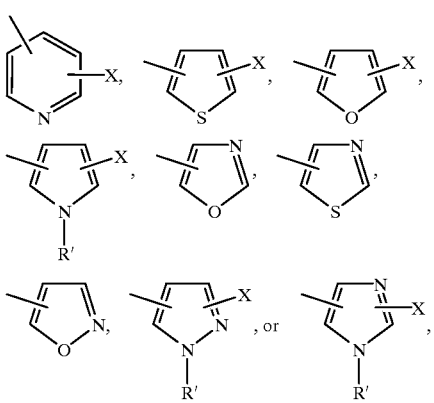

wherein X is hydrogen, halogen, (C$_1$–C$_3$)alkyl or —OCH$_3$, and R and R' are as defined above;
L is hydrogen, (C$_1$–C$_3$)alkyl, —CN, —OR', —SR', —CF$_3$, —OCF$_3$, Cl, F, NH$_2$, —NH—(C$_1$–C$_3$)alkyl, —N(R')CO(C$_1$–C$_3$)alkyl, N(R')(R'), —NO$_2$, —CONH$_2$, —SO$_2$NH$_2$ — SO$_2$N(R')(R'), —N(R')COCH$_2$O—(C$_1$–C$_3$)alkyl,

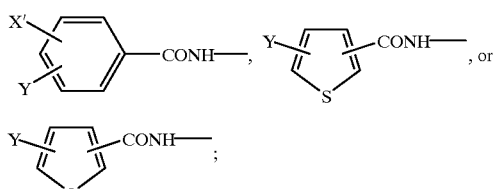

M is

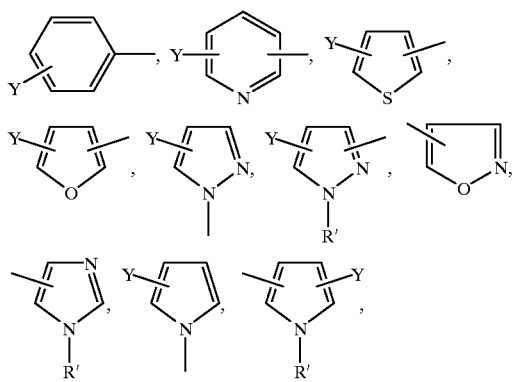

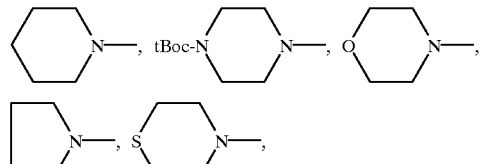

or N(R')(R') where R' is as defined above;
W is O, S, NH or N(C$_1$–C$_3$)alkyl;
Y is hydrogen, F, Cl, CF$_3$ or OCH$_3$; and X' is halogen, hydrogen, (C$_1$–C$_3$)alkyl, O—(C$_1$–C$_3$)alkyl, or —CH$_2$OH; and pharmaceutically acceptable salts thereof.

2. A compound according to claim 1, wherein

R is hydrogen, (C$_1$–C$_3$) alkyl, —CN, —OR', —SR', —CF$_3$, —OCF$_3$, Cl, F, NH$_2$, NH(C$_1$–C$_3$)alkyl, —N(R')CO(C$_1$–C$_3$)alkyl, —N(R')(R'), NO$_2$, —CONH$_2$, —SO$_2$NH$_2$, —SO$_2$N(R')(R'), or -N(R')COCH$_2$O—(C$_1$–C$_3$)alkyl, wherein R' is (C$_1$–C$_3$) alkyl or hydrogen;

R$_4$ is (C$_1$–C$_6$) alkyl—O—, (C$_1$–C6) alkyl—S—,

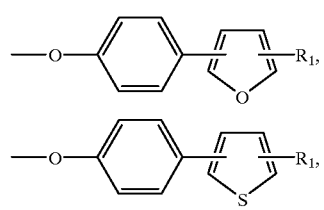

-continued

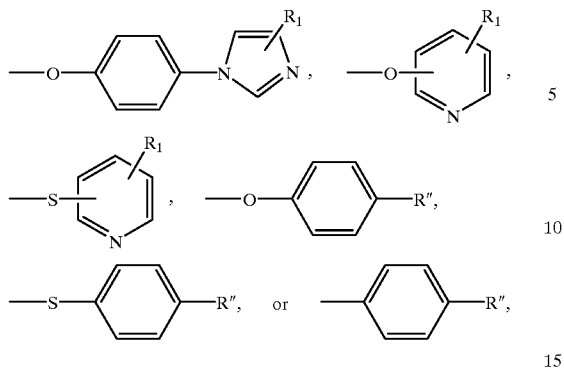

wherein R is hydrogen, halogen, cyano, methyl or —OCH₃;

R¹ and R² are each, independently, hydrogen or CH₃;

R₃ is (C₁–C₈)alkyl, NH₂CH₂CO—, (C₁–C₆)alkylNHCH₂CO—, HO(CH₂)ₘCO—, HCO—, Aryl(CH₂)ₙCO—, Heteroaryl(CH₂)ₙCO—, (C₁–C₃)alkyl—O—(CH₂)ₙCO—, (C₁–C₃)alkylCO—, (C₁–C₃)alkylCO—NHCH₂CO—, (C₃–C₇)cycloalkylCO—, Aryl—O—CH₂CO—, HeteroarylOCH₂CO—, ArylCH=CHCO—, HeteroarylCH=CHCO—, (C₁–C3)alkylCH=CHCO—,

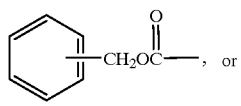, or

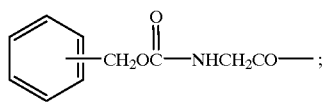;

wherein
m=1 to 3; n=0 to 3;
Aryl is

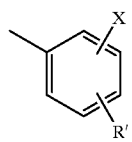

and
Heteroaryl is

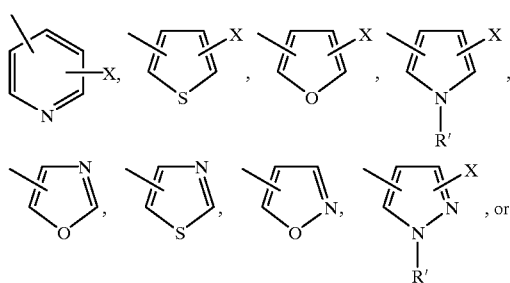

-continued

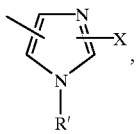, wherein X is hydrogen, halo-en, (C₁–C₃) alkyl or —OCH₃ wherein R and R' are as defined above; and pharmaceutically acceptable salts thereof.

3. A compound according to claim 1, wherein

R is hydrogen, (C₁–C₃) alkyl. —CN, —OR', —SR', —CF₃, —OCF₃, Cl, F, NH₂, NH(C₁–C₃)alkyl, —N(R')CO(C₁–C₃)alkyl, —N(R')(R'), NO₂, —CONH₂, —SO₂NH₂, —SO₂N(R')(R'), —N(R')COCH₂O—(C₁–C₃)alkyl, wherein R' is (C₁–C₃) alkyl or hydrogen;

R₄ is (C₁–C₆) alkyl—O—, (C₁–C₆) alkyl—S—,

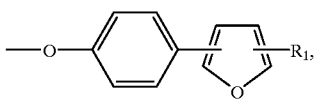

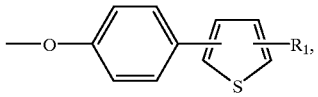

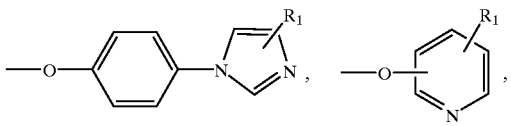

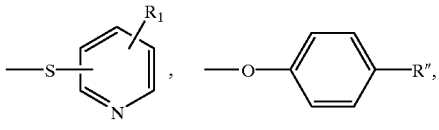

wherein R" is hydrogen, halogen, cyano, methyl or —OCH₃;

R₁ and R₂ are each, independently, hydrogen or CH₃;

R₃ is

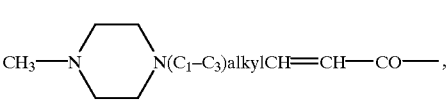

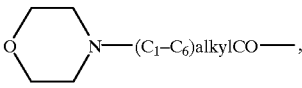

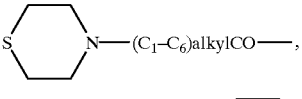

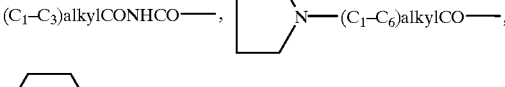

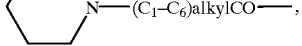

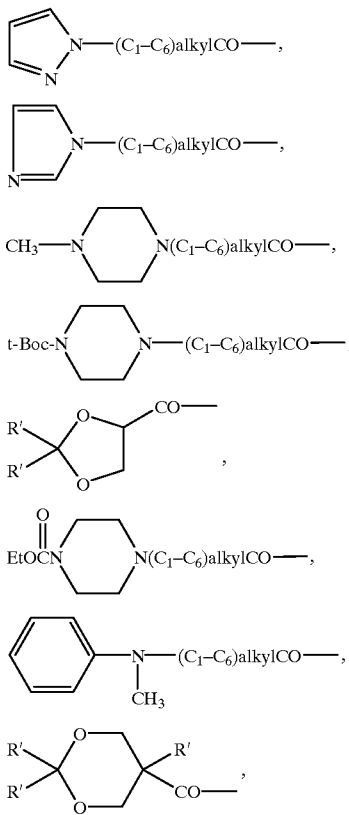

[(C₁-C₆)alkyl]₂—N—(C₁-C₆)alkyl CO—, or (C₁-C₆) alkyl—NH—(C₁-C₆)alkylCO—, where R' is as defined above;

and pharmaceutically acceptable salts thereof.

4. A compound according to claim 1, wherein

R is hydrogen, (C₁-C₃) alkyl, —CN, —OR', —SR', —CF₃, —OCF₃, Cl, F, NH₂, NH(C₁-C₃)alkyl, —N(R')CO(C₁-C₃)alkyl, —N(R')(R'), NO₂, —CONH₂, —SO₂NH₂, —SO₂N(R')(R'), —N(R')COCH₂O—(C₁-C₃)alkyl, wherein R' is (C₁-C₃) alkyl or hydrogen;

R₄ is (C₁-C₆) alkyl—O—, (C₁-C₆) alkyl—S—.

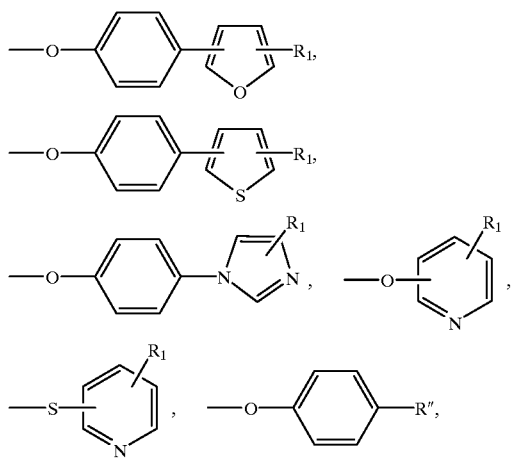

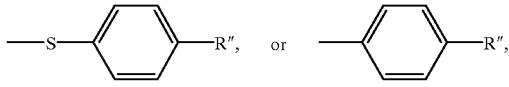

wherein R" is hydrogen, halogen, cyano, methyl or —OCH₃;

R₁ and R₂ are each, independently, hydrogen or CH₃;

R₃ is (C₁-C₃)alkylSO₂—, Aryl(CH₂)ₙSO₂—, Heteroaryl(CH₂)ₙSO₂—, or (C₁-C₃)alkyl—O—(CH₂)ₘ—SO₂, wherein m=1 to 3; n=0 to 3;

Aryl is

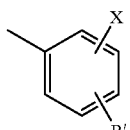

and

Heteroaryl is

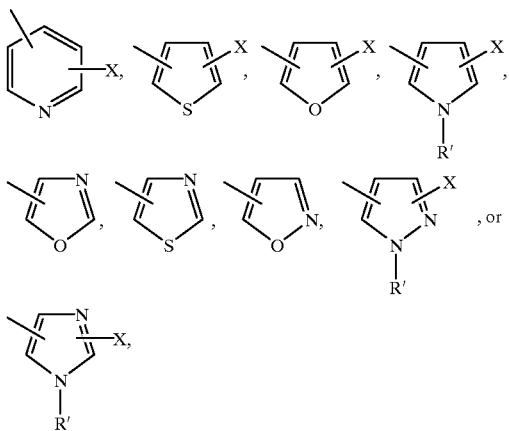

wherein X is hydrogen, halogen, (C₁-C₃) alkyl or —OCH₃ and R and R' are as defined above, and pharmaceutically acceptable salts thereof.

5. A compound according to claim 1, wherein

R is hydrogen, (C₁-C₃) alkyl, —CN, —OR', —SR', —CF₃, —OCF₃, Cl, F, NH₂, NH(C₁-C₃)alkyl, —N(R')CO(C₁-C₃)alkyl, —N(R')(R'), NO₂, —CONH₂, —SO₂NH₂, —SO₂N(R')(R'), or —N(R')COCH₂O—(C₁-C₃)alkyl, wherein R' is (C₁-C₃) alkyl or hydrogen;

R₄ is (C₁-C₆) alkyl—O—, (C₁-C₆) alkyl—S—,

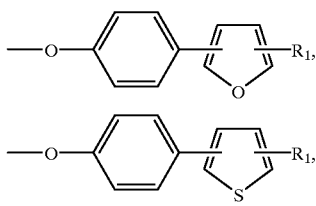

-continued

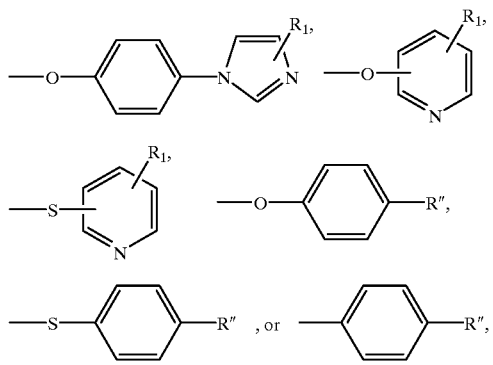

wherein R" is hydrogen, halogen, cyano, methyl or —OCH₃;

R₁ and R₂ are each, independently, hydrogen or CH₃;

R₃ is (C₁–C₈)alkyl, Aryl(C₁–C₃)alkyl, Heteroaryl(C₁–C₃)alkyl, ArylCH=CHCH₂, HeteroarylCH=CHCH₂—, or (C₁–C₆)alkylCH=CHCH₂—; wherein Aryl is

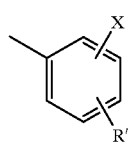

and

Heteroaryl is

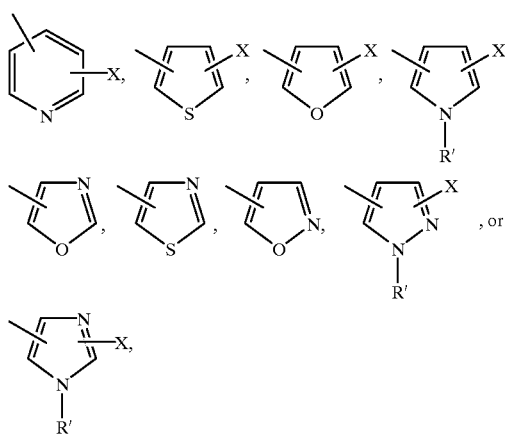

wherein X is hydrogen, halogen, (C₁–C₃) alkyl or —OCH₃ and R and R' are is as defined above;

and pharmaceutically acceptable salts thereof.

6. A compound according to claim 1, wherein

R is hydrogen, (C₁–C₃) alkyl, —CN, —OR', —SR', —CF₃, —OCF₃, Cl, F, NH₂, NH(C₁–C₃)alkyl, —N(R')CO(C₁–C₃)alkyl, —N(R')(R'), NO₂, —CONH₂, —SO₂NH₂, —SO₂N(R')(R'), or —N(R')COCH₂O-(C₁–C₃)alkyl, wherein R'is (C₁–C₃) alkyl or hydrogen;

R₄ is (C₁–C₆) alkyl—O—, (C₁–C₆) alkyl—S—,

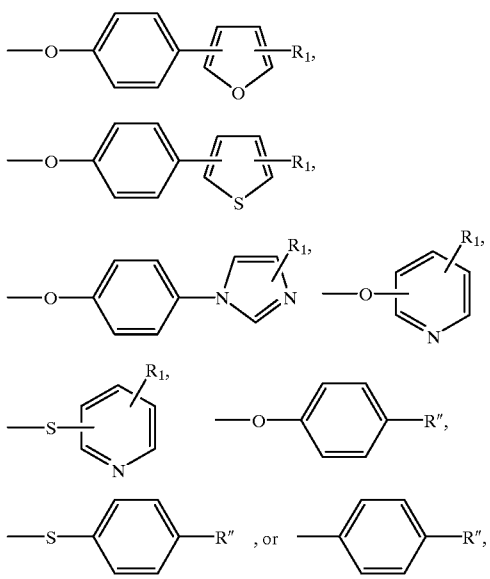

wherein R" is hydrogen, halogen, cyano, methyl or —OCH₃:

R₁ and R₂ are each, independently, hydrogen or CH₃;

R₃ is

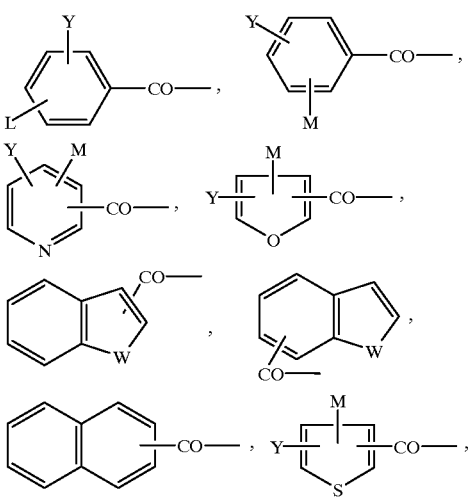

wherein m=1 to 3; n=0 to 3;

L is hydrogen, (C₁–C₃)alkyl, —CN, —OR', —SR', —CF₃, —OCF₃, Cl, F, NH₂, —NH—(C₁–C₃)alkyl, —N(R')CO(C₁–C₃)alkyl, N(R')(R'), —NO₂, —CONH₂, —SO₂NH₂, —SO₂N(R')(R'), —N(R') COCH₂O—(C₁–C₃)alkyl,

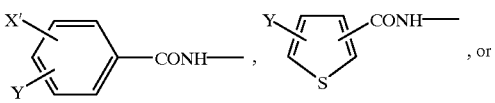

-continued

M is or N(R')(R') where R' is as defined above;

W is O, S, NH or N(C$_1$–C$_3$)alkyl;

Y is hydrogen, F, Cl, CF$_3$ or OCH$_3$; and X' is halogen, hydrogen, (C$_1$–C$_3$)alkyl, O—(C$_1$–C$_3$)alkyl, or —CH$_2$OH; and pharmaceutically acceptable salts thereof.

7. The compound according to claim 1 which is 4-(4-Methoxybenzenesulfonyl)-1-(3-trifluoromethylbenzoyl)-2,3,4,5-tetrahydro-1H-[1,4]benzodiazepine-3-carboxylic acid, hydroxyamide.

8. The compound according to claim 1 which is 4-(4-Methoxybenzenesulfonyl)-1-(4-methylphenylsulfonyl)-2,3,4,5-tetrahydro-1H-[1,4]benzodiazepine-3-carboxylic acid, hydroxyamide.

9. The compound according to claim 1 which is 1-(Methanesulfonyl)-4-(4-methoxybenzenesulfonyl)-2,3,4,5-tetrahydro-1H-[1,4]benzodiazepine-3-carboxylic acid, hydroxyamide.

10. The compound according to claim 1 which is 1,4-Bis-(4-methoxybenzenesulfonyl)-2,3,4,5-tetrahydro-1H-[1,4]benzodiazepine-3-carboxylic acid, hydroxyamide.

11. The compound according to claim 1 which is 1-Benzoyl-4-(4-methoxybenzenesulfonyl)-2,3,4,5-tetrahydro-1H-[1,4]benzodiazepine-3-carboxylic acid, hydroxyamide.

12. The compound according to claim 1 which is 1-Acetyl-4-(4-methoxybenzenesulfonyl)-2,3,4,5-tetrahydro-1H-[1,4]benzodiazepine-3-carboxylic acid, hydroxyamide.

13. The compound according to claim 1 which is 4-(4-Methoxybenzenesulfonyl)-1-(3-pyridinylcarbonyl)-2,3,4,5-tetrahydro-1H-[1,4]benzodiazepine-3-carboxylic acid, hydroxyamide.

14. The compound according to claim 1 which is 4-(4-Methoxybenzenesulfonyl)-1-(2-thienylcarbonyl)-2,3,4,5-tetrahydro-1H-[1,4]benzodiazepine-3-carboxylic acid, hydroxyamide.

15. The compound according to claim 1 which is 1-Methoxyacetyl-4-(4-methoxybenzenesulfonyl)-2,3,4,5-tetrahydro-1H-[1,4]benzodiazepine-3-carboxylic acid, hydroxyamide.

16. The compound according to claim 1 which is 4-(4-Methoxybenzenesulfonyl)-1-(propane-1-sulfonyl)-2,3,4,5-tetrahydro-1H-[1,4]benzodiazepine-3-carboxylic acid, hydroxyamide.

17. The compound according to claim 1 which is 4-(4-Methoxybenzenesulfonyl)-1-(2-methyl-5-fluorobenzoyl)-2,3,4,5-tetrahydro-1H-[1,4]benzodiazepine-3-carboxylic acid, hydroxyamide.

18. The compound according to claim 1 which is 4-(4-Methoxybenzenesulfonyl)-1-(4-pyridinylcarbonyl)-2,3,4,5-tetrahydro-1 H-[1,4]benzodiazepine-3-carboxylic acid, hydroxyamide.

19. The compound according to claim 1 which is 4-(4-Methoxybenzenesulfonyl)-1-(3-phenylpropionyl)-2,3,4,5-tetrahydro-1H-[1,4]benzodiazepine-3-carboxylic acid, hydroxyamide.

20. The compound according to claim 1 which is 1-([1,1'-Biphenyl]-2-carbonyl)-4-(4-methoxybenzene-sulfonyl)-2,3,4,5-tetrahydro-1H-[1,4]benzodiazepine-3-carboxylic acid, hydroxyamide.

21. The compound according to claim 1 which is 1-(4-Biphenylcarbonyl)-4-(4-methoxybenzenesulfonyl)-2,3,4,5-tetrahydro-1H-[1,4]benzodiazepine-3-carboxylic acid, hydroxyamide.

22. The compound according to claim 1 which is 1-(3-Fluorobenzoyl)-4-(4-methoxybenzenesulfonyl)-2,3,4,5-tetrahydro-1H-[1,4]benzodiazepine-3-carboxylic acid, hydroxyamide.

23. The compound according to claim 1 which is 4-(4-Methoxybenzenesulfonyl)-1-(2-methyl-3-fluorobenzoyl)-2,3,4,5-tetrahydro-1H-[1,4]benzodiazepine-3-carboxylic acid, hydroxyamide.

24. The compound according to claim 1 which is 4-(4-Methoxybenzenesulfonyl)-1-(2-methyl-3-trifluoromethylbenzoyl)-2,3,4,5-tetrahydro-1H-[1,4]benzodiazepine-3-carboxylic acid, hydroxyamide.

25. The compound according to claim 1 which is 1-(2-Chloro-6-trifluoromethylbenzoyl)-4-(4-methoxybenzenesulfonyl)-2,3,4,5-tetrahydro-1H-[1,4]benzodiazepine-3-carboxylic acid, hydroxyamide.

26. The compound according to claim 1 which is 1-(4-Fluoro-2-trifluoromethylbenzoyl)-4-(4-methoxybenzenesulfonyl)-2,3,4,5-tetrahydro-1H-[1,4]benzodiazepine-3-carboxylic acid, hydroxyamide.

27. The compound according to claim 1 which is 1-(2-Fluoro-6-trifluoromethylbenzoyl)-4-(4-methoxybenzenesulfonyl)-2,3,4,5-tetrahydro-1H-[1,4]benzodiazepine-3-carboxylic acid, hydroxyamide.

28. The compound according to claim 1 which is 4-(4-Methoxybenzenesulfonyl)-1-(2-methylbenzoyl)-2,3,4,5-tetrahydro-1H-[1,4]benzodiazepine-3-carboxylic acid, hydroxyamide.

29. The compound according to claim 1 which is 4-(4-Methoxybenzenesulfonyl)-1-(2-methyl-6-chlorobenzoyl)-2, 3,4,5-tetrahydro-1H-[1,4]benzodiazepine-3-carboxylic acid, hydroxyamide.

30. The compound according to claim 1 which is 1-(2,4-Dimethylbenzoyl)4-(4-methoxybenzenesulfonyl)-2,3,4,5-tetrahydro-1H-[1,4]benzodiazepine-3-carboxylic acid, hydroxyamide.

31. The compound according to claim 1 which is 1-(2,5-Dimethylbenzoyl)-4-(4-methoxybenzenesulfonyl)-2,3,4,5-tetrahydro-1H-[1,4]benzodiazepine-3-carboxylic acid, hydroxyamide.

32. The compound according to claim 1 which is 1-(2-Chloro-4-fluorobenzoyl)-4-(4-methoxybenzenesulfonyl)-2,3,4,5-tetrahydro-1H-[1,4]benzodiazepine-3-carboxylic acid, hydroxyamide.

33. The compound according to claim 1 which is 1-(2-Chlorobenzoyl)4-(4-methoxybenzenesulfonyl)-2,3,4,5-tetrahydro-1H-[1,4]benzodiazepine-3-carboxylic acid, hydroxyamide.

34. The compound according to claim 1 which is 1-(2-Fluorobenzoyl)-4-(4-methoxybenzenesulfonyl)-2,3,4,5-tetrahydro-1H-[1,4]benzodiazepine-3-carboxylic acid, hydroxyamide.

35. The compound according to claim 1 which is 1-(2-Chloro-6-fluorobenzoyl)-4-(4-methoxybenzenesulfonyl)-2,3,4,5-tetrahydro-1H-[1,4]benzodiazepine-3-carboxylic acid, hydroxyamide.

36. The compound according to claim 1 which is 1-(2,3-Difluorobenzoyl)-4-(4-methoxybenzenesulfonyl)-2,3,4,5-tetrahydro-1H-[1,4]benzodiazepine-3-carboxylic acid, hydroxyamide.

37. The compound according to claim 1 which is 1-(2,4-Dichlorobenzoyl)-4-(4-methoxybenzenesulfonyl)-2,3,4,5-tetrahydro-1H-[1,4]benzodiazepine-3-carboxylic acid, hydroxyamide.

38. The compound according to claim 1 which is 1-(2,3-Dichlorobenzoyl)-4-(4-methoxybenzenesulfonyl)-2,3,4,5-tetrahydro-1H-[1,4]benzodiazepine-3-carboxylic acid, hydroxyamide.

39. The compound according to claim 1 which is 1-(2,5-Dichlorobenzoyl)-4-(4-methoxybenzenesulfonyl)-2,3,4,5-tetrahydro-1H-[1,4]benzodiazepine-3-carboxylic acid, hydroxyamide.

40. The compound according to claim 1 which is 1-(2-Methoxybenzoyl)-4-(4-methoxybenzenesulfonyl)-2,3,4,5-tetrahydro-1H-[1,4]benzodiazepine-3-carboxylic acid, hydroxyamide.

41. The compound according to claim 1 which is 1-(4-Chloro-2-methoxybenzoyl)-4-(4-methoxybenzenesulfonyl)-2,3,4,5-tetrahydro-1H-[1,4]benzodiazepine-3-carboxylic acid, hydroxyamide.

42. The compound according to claim 1 which is 4-(4-Methoxybenzenesulfonyl)-1-(2-methoxybenzenesulfonyl)-2,3,4,5-tetrahydro-1H-[1,4]benzodiazepine-3-carboxylic acid, hydroxyamide.

43. The compound according to claim 1 which is 4-(4-Methoxybenzenesulfonyl)-1-(3-methyl-2-thienylcarbonyl)-2,3,4,5-tetrahydro-1H-[1,4]benzodiazepine-3-carboxylic acid, hydroxyamide.

44. The compound according to claim 1 which is 4-(4-Methoxybenzenesulfonyl)-1-(4-methyl-2-thienylcarbonyl)-2,3,4,5-tetrahydro-1H-[1,4]benzodiazepine-3-carboxylic acid, hydroxyamide.

45. The compound according to claim 1 which is 1-(3-Chloro-2-thienylcarbonyl)-4-(4-methoxybenzenesulfonyl)-2,3,4,5-tetrahydro-1H-[1,4]benzodiazepine-3-carboxylic acid, hydroxyamide.

46. The compound according to claim 1 which is 1-(2-Furanylcarbonyl)-4-(4-methoxybenzenesulfonyl)-2,3,4,5-tetrahydro-1H-[1,4]benzodiazepine-3-carboxylic acid, hydroxyamide.

47. The compound according to claim 1 which is 4-(4-Methoxybenzenesulfonyl)-1-(3-methyl-2-furanylcarbonyl)-2,3,4,5-tetrahydro-1H-[1,4]benzodiazepine-3-carboxylic acid, hydroxyamide.

48. The compound according to claim 1 which is 4-(4-Methoxybenzenesulfonyl)-1-(4-methyl-2-furanylcarbonyl)-2,3,4,5-tetrahydro-1H-[1,4]benzodiazepine-3-carboxylic acid, hydroxyamide.

49. The compound according to claim 1 which is 1-(5-Chloro-2-furanylcarbonyl)-4-(4-methoxybenzenesulfonyl)-2,3,4.5-tetrahydro-1H-[1,4]benzodiazepine-3-carboxylic acid, hydroxyamide.

50. The compound according to claim 1 which is 1-(5-Chloro-2-thienylcarbonyl)-4-(4-methoxybenzenesulfonyl)-2,3,4,5-tetrahydro-I H-[1,4]benzodiazepine-3-carboxylic acid, hydroxyamide.

51. The compound according to claim 1 which is 1-Propionyl-4-(4-methoxybenzenesulfonyl)-2,3,4,5-tetrahydro-1H-[1,4]benzodiazepine-3-carboxylic acid, hydroxyamide.

52. The compound according to claim 1 which is 1-Hexanoyl-4-(4-methoxybenzenesulfonyl)-2,3,4,5-tetrahydro-1H-[1,4]benzodiazepine-3-carboxylic acid, hydroxyamide.

53. The compound according to claim 1 which is 1-(3-Methoxypropionyl)-4-(4-methoxybenzenesulfonyl)-2,3,4,5-tetrahydro-1H-[1,4]benzodiazepine-3-carboxylic acid, hydroxyamide.

54. The compound according to claim 1 which is 4-(4-Methoxybenzenesulfonyl)-1-(3-thienylcarbonyl)-2,3,4,5-tetrahydro-1H-[1,4]benzodiazepine-3-carboxylic acid, hydroxyamide.

55. The compound according to claim 1 which is 1-(3-Furanylcarbonyl)4-(4-methoxybenzenesulfonyl)-2,3,4,5-tetrahydro-1H-[1,4]benzodiazepine-3-carboxylic acid, hydroxyamide.

56. The compound according to claim 1 which is 1-(trans-Crotonyl)-4-(4-methoxybenzenesulfonyl)-2,3,4,5-tetrahydro-1H-[1,4]benzodiazepine-3-carboxylic acid, hydroxyamide.

57. The compound according to claim 1 which is 1-(Methacryloyl)-4-(4-methoxybenzenesulfonyl)-2,3,4,5-tetrahydro-1H-[1,4]benzodiazepine-3-carboxylic acid, hydroxyamide.

58. The compound according to claim 1 which is 1-(Acetylaminoacetyl)-4-(4-methoxybenzenesulfonyl)-2,3,4,5-tetrahydro-1H-[1,4]benzodiazepine-3 -carboxylic acid, hydroxyamide.

59. The compound according to claim 1 which is 1-(Aminoacetyl)-4-(4-methoxybenzenesulfonyl)-2.3,4,5-tetrahydro-1H-[1,4]benzodiazepine-3-carboxylic acid, hydroxyamide.

60. The compound according to claim 1 which is 1-(N,N-Dimethylaminoacetyl)-4-(4-methoxybenzenesulfonyl)-2,3,4,5-tetrahydro-1H-[1,4]benzodiazepine-3-carboxylic acid, hydroxyamide.

61. The compound according to claim 1 which is 1-(Cyclopropylcarbonyl)-4-(4-methoxybenzenesulfonyl)-2,3,4,5-tetrahydro-1H-[1,4]benzodiazepine-3-carboxylic acid, hydroxyamide.

62. The compound according to claim 1 which is 4-(4-Methoxybenzenesulfonyl)-1-(4-(2-thienyl)phenylcarbonyl)-2,3,4,5-tetrahydro-1H-[1,4]benzodiazepine-3-carboxylic acid, hydroxyamide.

63. The compound according to claim 1 which is 4-(4-Methoxybenzenesulfonyl)-1-(4-(3-thienyl)phenylcarbonyl)-

2,3,4,5-tetrahydro-1H-[1,4]benzodiazepine-3-carboxylic acid, hydroxyamide.

64. The compound according to claim 1 which is 4-(4-Methoxybenzenesulfonyl)-1-[2-(1-pyrazolyl)phenylcarbonyl]-2,3,4,5-tetrahydro-1H-[1,4]benzodiazepine-3-carboxylic acid, hydroxyamide.

65. The compound according to claim 1 which is 4-(4-Methoxybenzenesulfonyl)-1-[2-(3-pyrazolyl)phenylcarbonyl]-2,3,4,5-tetrahydro-1H-[1,4]benzodiazepine-3-carboxylic acid, hydroxyamide.

66. The compound according to claim 1 which is 1-(Cycloyhexylcarbonyl)-4-(4-methoxybenzenesulfonyl)-2,3,4,5-tetrahydro-1H-[1,4]-benzodiazepine-3-carboxylic acid, hydroxyamide.

67. The compound according to claim 1 which is 1-Methoxyacetyl-4-(4-methoxybenzenesulfonyl)-7-methyl-2,3,4,5-tetrahydro-1H-[1,4]-benzodiazepine-3-carboxylic acid, hydroxyamide.

68. The compound according to claim 1 which is 1-Benzoyl-4-(4-methoxybenzenesulfonyl)-7-methyl-2,3,4,5-tetrahydro-1H-[1,4]-benzodiazepine-3-carboxylic acid, hydroxyamide.

69. The compound according to claim 1 which is 4-(4-Methoxybenzenesulfonyl)-1-[(4-trifluoromethoxy)benzoyl]-8-chloro-2,3,4.5-tetrahydro-1H-[1,4]benzodiazepine-3-carboxylic acid, hydroxyamide.

70. The compounds according to claim 1, which is 4-(4-methoxybenzenesulfonyl)-1-[2-chloro-4-(3-methyl-1-pyrazolyl)phenylcarbonyl]-2,3,4,5-tetrahydro-1H[1,4]-benzodiazepine-3-carboxylic acid, hydroxyamide.

71. The compound according to claim 1 which is 4-(4-Methoxybenzenesulfonyl)-1-[2-(1-pyrazolyl)phenylcarbonyl]-7-methyl-2,3,4,5-tetrahydro-1H-[1,4]benzodiazepene-3-carboxylic acid, hydroxyamide.

72. The compound according to claim 1 which is 4-(4-Methoxybenzenesulfonyl)-1-[2-(4-morpholino)phenylcarbonyl]-8-chloro-2,3,4,5-tetrahydro-1H-[1,4]benzodiazepine-3-carboxylic acid, hydroxyamide.

73. The compound according to claim 1 which is 1-(4-Ethoxybenzoyl)-4-(4-methoxybenzenesulfonyl)-2.3,4,5-tetrahydro-1 H-[1,4]benzodiazepine-3-carboxylic acid, hydroxyamide.

74. The compound according to claim 1 which is 1-(Cyclobutylcarbonyl)-4-(4-methoxybenzenesulfonyl)-2,3,4,5-tetrahydro-1H-[1,4]benzodiazepine-3-carboxylic acid, hydroxyamide.

75. The compound according to claim 1 which is 4-(4-Methoxybenzenesulfonyl)-1-(phenoxyacetyl)-2,3,4,5-tetrahydro-1H-[1,4]benzodiazepine-3-carboxylic acid, hydroxyamide.

76. The compound according to claim 1 which is 4-(4-Methoxybenzenesulfonyl)-1-(2-methoxyethyl)-2,3,4,5-tetrahydro-1H-[1,4]benzodiazepine-3-carboxylic acid, hydroxyamide.

77. The compound according to claim 1 which is 1-Benzyl-4-(4-methoxybenzenesulfonyl)-2,3,4,5-tetrahydro-1H-[1,4]benzodiazepine-3-carboxylic acid, hydroxyamide.

78. The compound according to claim 1 which is 1-(2,4-Dimethoxybenzoyl)-4-(4-methoxybenzenesulfonyl)-2,3,4,5-tetrahydro-1H-[1,4]benzodiazepine-3-carboxylic acid, hydroxyamide.

79. The compound according to claim 1 which is 4-(4-Methoxybenzenesulfonyl)-1-[2-(4-methylpiperazin-1-yl)acetyl]-2,3,4,5-tetrahydro-1H-[1,4]benzodiazepine-3-carboxylic acid, hydroxyamide.

80. The compound according to claim 1 which is 4-[4-(4-Chlorophenyloxy)benzenesulfonyl]-1-(methoxyacetal)-2,3,4,5-tetrahydro-1H-[1,4]benzodiazepine-3-carboxylic acid, hydroxyamide.

81. The compound according to claim 1 which is 4-[4-(4-Chlorophenyloxy)benzenesulfonyl]-1-(2-thienylcarbonyl)-2,3,4,5-tetrahydro-1H-[1,4]benzodiazepine-3-carboxylic acid, hydroxyamide.

82. The compound according to claim 1 which is 4-[4-(4-Chlorophenyloxy)benzenesulfonyl]-1-(benzoyl-2,3,4,5-tetrahydro-1H-[1,4]benzodiazepine-3-carboxylic acid, hydroxyamide.

83. The compound according to claim 1 which is 4-[4-(4-Pyridinyloxy)benzenesulfonyl]-1-(methoxyacetyl)-2,3,4,5-tetrahydro-1H-[1,4]benzodiazepine-3-carboxylic acid, hydroxyamide.

84. A pharmaceutical composition comprising a compound of Formula I wherein

R is selected from hydrogen. $(C_1-C_3)$ alkyl, —CN, —OR', —SR', —CF$_3$ —OCF$_3$, Cl, F, NH$_2$, NH($C_1-C_3$) alkyl, —N(R')CO($C_1-C_3$)alkyl, —N(R')(R'), NO$_2$, —CONH$_2$, —SO$_2$NH$_2$, —SO$_2$N(R')(R'), —N(R')COCH$_2$O—($C_1-C_3$)alkyl, wherein R' is ($C_1-C_3$) alkyl or hydrogen;

R$_4$ is hydroxy ($C_1$ - $C_6$) alkyl—O—, ($C_1-C_6$) alkyl—S—, wherein R is hydrogen, halogen, cyano, methyl or —OCH$_3$;

R$_1$ and R$_2$ are each, independently, hydrogen or CH$_3$;

R$_3$ is $(C_1-C_8)$alkyl. NH$_2$CH$_2$CO—, $(C_1-C_6)$ alkylNHCH$_2$CO—, HO(CH$_2$)$_m$CO—, HCO—, Aryl(CH$_2$)$_n$CO—, Heteroaryl(CH$_2$)$_n$CO—, $(C_1-C_3)$alkyl—

O—(CH$_2$)$_n$CO—. (C$_1$–C$_3$)alkylCO—, (C$_1$–C$_3$)alkylCO—NHCH$_2$CO—, (C$_3$–C$_7$)cycloalkylCO—, (C$_1$–C$_3$)alkylSO$_2$—, Aryl(CH$_2$)$_n$SO$_2$—, Heteroaryl(CH$_2$)$_n$SO$_2$—. (C$_1$–C$_3$)alkyl—O—(CH$_2$)$_m$—SO$_2$—, (C$_1$–C$_3$)alkyl—O—(CH$_2$)$_m$, (C$_1$–C$_3$)alkyl—O—(C$_1$–C$_3$)alkyl, HO—(C$_1$–C$_3$)alkyl—O—(C$_1$–C$_3$)alkyl, Aryl—O—CH$_2$CO—, Heteroaryl—O—CH$_2$CO—, ArylCH=CHCO—, HeteroarylCH=CHCO—, (C$_1$–C$_3$)alkylCH=CHCO—;

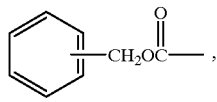

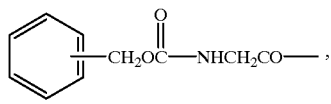

Aryl(C$_1$–C$_3$)alkyl, Heteroaryl(C$_1$–C$_3$)alkyl, ArylCH=CHCH$_2$—, HeteroarylCH=CHCH$_2$—, (C$_1$–C$_6$)alkylCH=CHCH$_2$—,

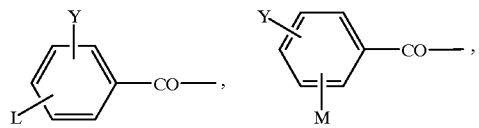

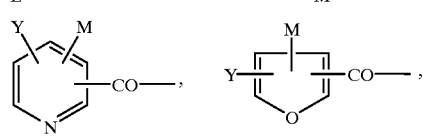

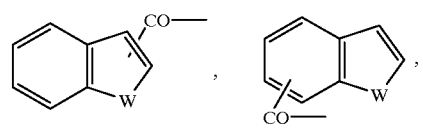

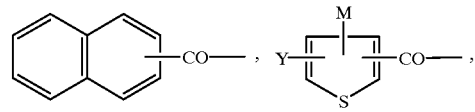

R'OCH$_2$ CH(OR')CO—, (R'OCH$_2$)$_2$C(R')CO—,

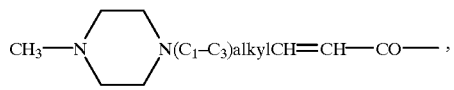

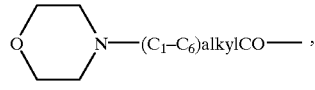

(C$_1$–C$_3$)alkylCONHCO—,

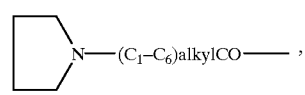

-continued

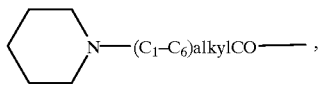

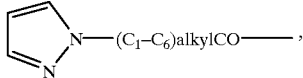

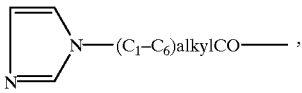

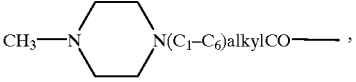

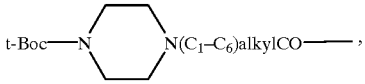

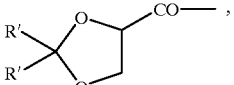

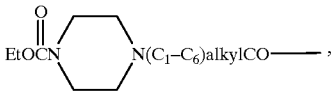

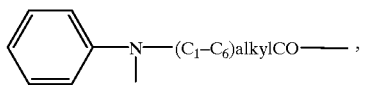

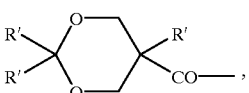

[(C$_1$–C$_6$)alkyl]$_2$—N—(C$_1$–C$_6$)alkyl CO—, or (C$_1$–C$_6$)alkyl—NH—(C$_1$–C$_6$)alkylCO—;

wherein m=1 to 3; n=0 to 3;

Aryl is

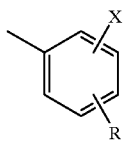

Heteroaryl is

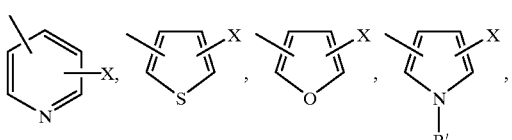

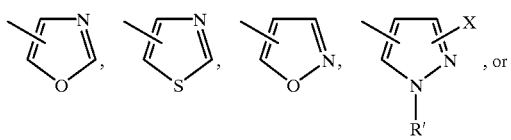

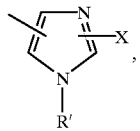

wherein X is hydrogen, halogen, $(C_1-C_3)$ alkyl or —$OCH_3$, and R and R' are as defined above;

L is hydrogen, $(C_1-C_3)$alkyl, —CN, —OR', —SR', —$CF_3$, —$OCF_3$, Cl, F, $NH_2$, —NH—$(C_1-C_3)$alkyl, —N(R')CO$(C_1-C_3)$alkyl, N(R')(R'), —$NO_2$—, —$CONH_2$, —$SO_2NH_2$, —$SO_2N(R')(R')$, —N(R') $COCH_2O$—$(C_1-C_3)$alkyl,

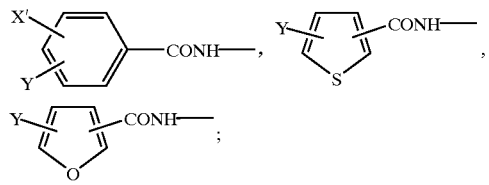

M is

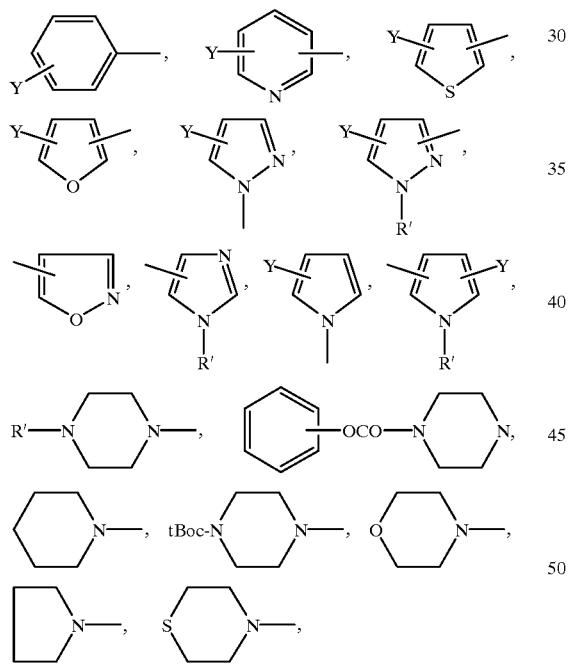

or N(R')(R') where R' is as defined above;

W is O, S, NH or N$(C_1-C_3)$alkyl;

Y is hydrogen, F, Cl, $CF_3$ or $OCH_3$; and X' is halogen, hydrogen, $(C_1-C_3)$alkyl, O-$(C_1-C_3)$alkyl, or —$CH_2OH$; and pharmaceutically acceptable salts thereof.

85. A method of treating disease conditions mediated by matrix metalloproteinase in a mammal in need thereof, which comprises administering to said mammal an effective amount of a compound of Formula 1

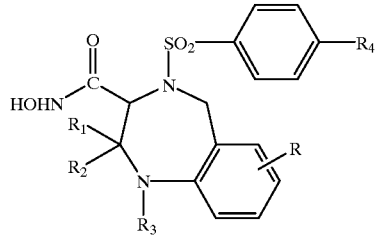

wherein

R is selected from hydrogen, $(C_1-C_3)$ alkyl, —CN, —OR', —SR', —$CF_3$, —$OCF_3$, Cl, F, $NH_2$, NH$(C_1-C_3)$alkyl, —N(R')CO$(C_1-C_3)$alkyl, —N(R') (R'), $NO_2$, —$CONH_2$, —$SO_2NH_2$, —$SO_2N(R')(R')$, —N(R')COCH$_2$O—$(C_1-C_3)$alkyl, wherein R' is $(C_1-C_3)$ alkyl or hydrogen;

$R_4$ is hydroxy, $(C_1-C_6)$ alkyl—O—, $(C_1-C_6)$ alkyl—S—,

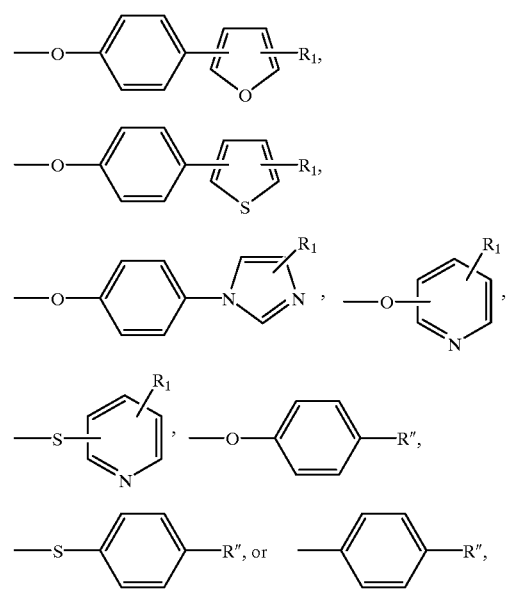

wherein R is hydrogen, halogen, cyano, methyl or —$OCH_3$;

$R^1$ and $R_2$ are each, independently, hydrogen or $CH_3$;

$R_3$ is $(C_1-C_8)$alkyl, $NH_2CH_2CO$—, $(C_1-C_6)$ alkylNHCH$_2$CO—, HO(CH$_2$)$_m$CO—, HCO—, Aryl (CH$_2$)$_n$CO—, Heteroaryl(CH$_2$)$_n$CO—, $(C_1-C_3)$alkyl—O—(CH$_2$)$_n$CO—, $(C_1-C_3)$alkylCO—, $(C_1-C_3)$ alkylCO—NHCH$_2$CO—, $(C_3-C_7)$cycloalkylCO—, $(C_1-C_3)$alkylSO$_2$—, Aryl(CH$_2$)$_n$SO$_2$—, Heteroaryl (CH$_2$)$_n$SO$_2$—, $(C_1-C_3)$alkyl—O—(CH$_2$)$_m$—SO$_2$—, $(C_1-C_3)$alkyl—O—(CH$_2$)$_m$, $(C_1-C_3)$alkyl—O—$(C_1-C_3)$alkyl—O—$(C_1-C_3)$alkyl, HO—$(C_1-C_3)$ alkyl—O—$(C_1-C_3)$alkyl, Aryl—O—CH$_2$CO—, Heteroaryl—O—CH$_2$CO—, ArylCH=CHCO—, HeteroarylCH=CHCO—, $(C_1-C_3)$ alkylCH=CHCO—;

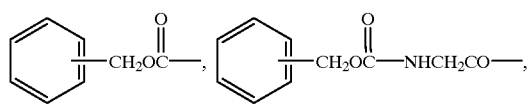

Aryl($C_1$–$C_3$)alkyl, Heteroaryl($C_1$–$C_3$)alkyl, ArylCH=CHCH$_2$—, HeteroarylCH=CHCH$_2$—, ($C_1$–$C_6$)alkylCH=CHCH$_2$—,

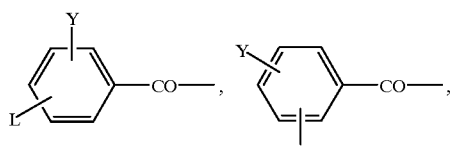

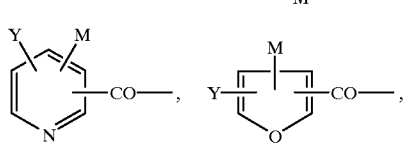

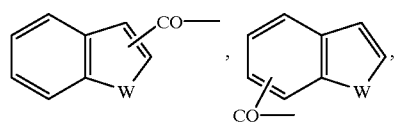

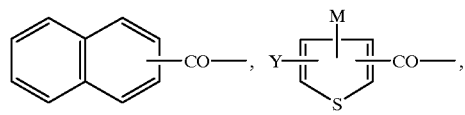

R'OCH$_2$ CH(OR')CO—, (R'OCH$_2$)$_2$C(R')CO—,

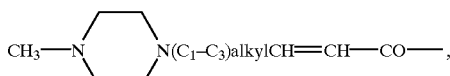

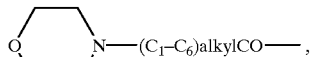

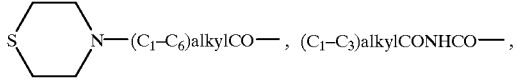

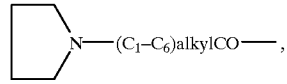

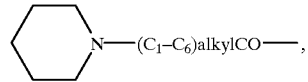

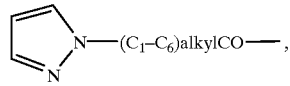

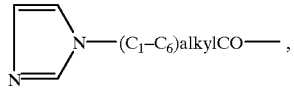

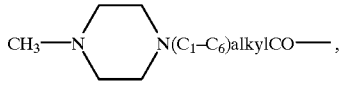

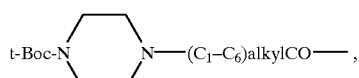

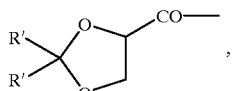

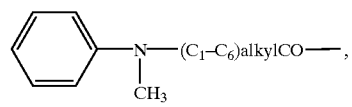

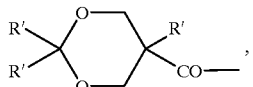

[($C_1$–$C_6$)alkyl]$_2$—N—($C_1$–$C_6$)alkyl CO—, or ($C_1$–$C_6$)alkyl—NH—($C_1$–$C_6$)alkylCO—;

wherein m=1 to 3; n=0 to 3;

Aryl is

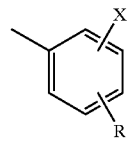

and

Heteroaryl is

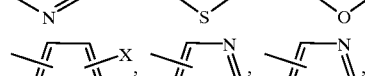

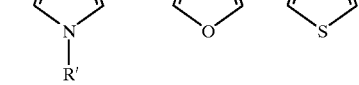

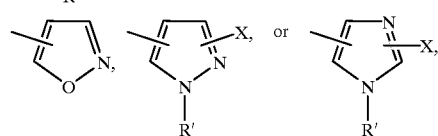

wherein X is hydrogen, halogen, ($C_1$–$C_3$) alkyl or —OCH$_3$, and R and R' are as defined above;

L is hydrogen, ($C_1$–$C_3$)alkyl, —CN, —OR', —SR', —CF$_3$, —OCF$_3$, Cl, F, NH$_2$, —NH—($C_1$–$C_3$)alkyl, —N(R')CO($C_1$–$C_3$)alkyl, N(R')(R'), —NO$_2$, —CONH$_2$, —SO$_2$NH$_2$, —SO$_2$N(R')(R'), —N(R')COCH$_2$—($C_1$–$C_3$)alkyl.

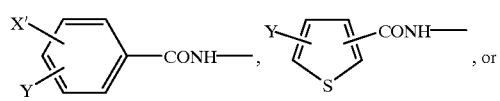
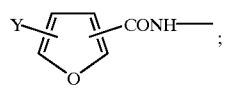
M is
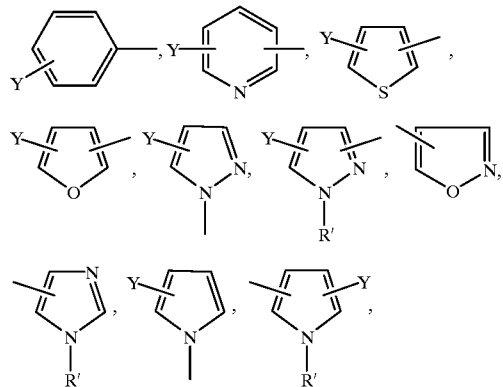
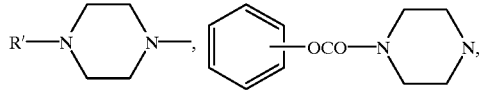
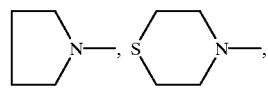
or (R')(R') where R' is as defined above;
W is O, S. NH or N(C$_1$–C$_3$)alkyl;
Y is hydrogen, F, Cl, CF$_3$ or OCH$_3$; and X' is halogen, hydrogen, (C$_1$–C$_3$)alkyl O—(C$_1$–C$_3$)alkyl, or —CH$_2$OH; and pharmaceutically acceptable salts thereof.
* * * * *